(12) United States Patent
Haddach et al.

(10) Patent No.: US 8,367,681 B2
(45) Date of Patent: Feb. 5, 2013

(54) PYRAZOLOPYRIMIDINES AND RELATED HETEROCYCLES AS KINASE INHIBITORS

(75) Inventors: Mustapha Haddach, San Diego, CA (US); Joe Tran, San Marcos, CA (US)

(73) Assignee: Cylene Pharmaceuticals, Inc., San Diego, CA (US)

( * ) Notice: Subject to any disclaimer, the term of this patent is extended or adjusted under 35 U.S.C. 154(b) by 137 days.

(21) Appl. No.: 12/784,271

(22) Filed: May 20, 2010

(65) Prior Publication Data

US 2010/0331314 A1 Dec. 30, 2010

Related U.S. Application Data

(60) Provisional application No. 61/180,090, filed on May 20, 2009, provisional application No. 61/218,318, filed on Jun. 18, 2009.

(51) Int. Cl.
*A01N 43/90* (2006.01)
*A61K 31/519* (2006.01)
*C07D 487/00* (2006.01)

(52) U.S. Cl. .................................... 514/259.3; 544/281
(58) Field of Classification Search .................. None
See application file for complete search history.

(56) References Cited

U.S. PATENT DOCUMENTS

2007/0082902 A1 4/2007 Paruch et al.

FOREIGN PATENT DOCUMENTS

WO  WO 2008/058126 A2  5/2008

OTHER PUBLICATIONS

Xia et al., "Synthesis and Evaluation of Novel Inhibitors of Pim-1 and Pim-2 Protein Kinases," J. Med. Chem. 52:74-86 (2008).
Young, "International Search Report," 2 pages, from International Appl. No. PCT/US10/35657, United States Patent and Trademark Office, Alexandria, Virginia, USA (mailed Aug. 13, 2010).
Young, "Written Opinion of the International Searching Authority," 4 pages, from International Appl. No. PCT/US10/35657, United States Patent and Trademark Office, Alexandria, Virginia, USA (mailed Aug. 13, 2010).

*Primary Examiner* — Jeffrey Murray
(74) *Attorney, Agent, or Firm* — Cooley LLP

(57) ABSTRACT

The invention provides compounds of general formula (I) that inhibit selected kinases (Pim and/or CK2 kinases) and compositions containing such compounds. These compounds and compositions are useful for treating proliferative disorders such as cancer, as well as other kinase-associated conditions including inflammation, pain, and certain infections and immunological disorders.

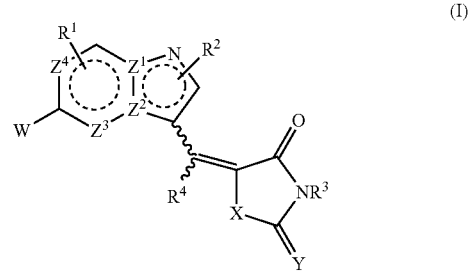

13 Claims, No Drawings

US 8,367,681 B2

SEQUENCE LISTING

<160> NUMBER OF SEQ ID NOS: 6

<210> SEQ ID NO 1
<211> LENGTH: 391
<212> TYPE: PRT
<213> ORGANISM: Homo sapiens

<400> SEQUENCE: 1

Met Ser Gly Pro Val Pro Ser Arg Ala Arg Val Tyr Thr Asp Val Asn
1               5                   10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
        35                  40                  45

Lys Tyr Ser Glu Val Phe Glu Ala Ile Asn Ile Thr Asn Asn Glu Lys
    50                  55                  60

Val Val Val Lys Ile Leu Lys Pro Val Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
        115                 120                 125

Thr Asp Tyr Asp Ile Arg Phe Tyr Met Tyr Glu Ile Leu Lys Ala Leu
    130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
        195                 200                 205

Tyr Asp Tyr Ser Leu Asp Met Trp Ser Leu Gly Cys Met Leu Ala Ser
    210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
            260                 265                 270

Leu Gly Arg His Ser Arg Lys Arg Trp Glu Arg Phe Val His Ser Glu
        275                 280                 285

Asn Gln His Leu Val Ser Pro Glu Ala Leu Asp Phe Leu Asp Lys Leu
    290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Met Met
            340                 345                 350

Ser Gly Ile Ser Ser Val Pro Thr Pro Ser Pro Leu Gly Pro Leu Ala
        355                 360                 365

Gly Ser Pro Val Ile Ala Ala Asn Pro Leu Gly Met Pro Val Pro
370             375             380

Ala Ala Ala Gly Ala Gln Gln
385             390

<210> SEQ ID NO 2
<211> LENGTH: 391
<212> TYPE: PRT
<213> ORGANISM: Homo sapiens

<400> SEQUENCE: 2

Met Ser Gly Pro Val Pro Ser Arg Ala Arg Val Tyr Thr Asp Val Asn
1               5                   10                  15

Thr His Arg Pro Arg Glu Tyr Trp Asp Tyr Glu Ser His Val Val Glu
                20                  25                  30

Trp Gly Asn Gln Asp Asp Tyr Gln Leu Val Arg Lys Leu Gly Arg Gly
            35                  40                  45

Lys Tyr Ser Glu Val Phe Glu Ala Ile Asn Ile Thr Asn Asn Glu Lys
50                  55                  60

Val Val Val Lys Ile Leu Lys Pro Val Lys Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
        115                 120                 125

Thr Asp Tyr Asp Ile Arg Phe Tyr Met Tyr Glu Ile Leu Lys Ala Leu
130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
        195                 200                 205

Tyr Asp Tyr Ser Leu Asp Met Trp Ser Leu Gly Cys Met Leu Ala Ser
210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
            260                 265                 270

Leu Gly Arg His Ser Arg Lys Arg Trp Glu Arg Phe Val His Ser Glu
        275                 280                 285

Asn Gln His Leu Val Ser Pro Glu Ala Leu Asp Phe Leu Asp Lys Leu
290                 295                 300

```
Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Met Met
            340                 345                 350

Ser Gly Ile Ser Ser Val Pro Thr Pro Ser Pro Leu Gly Pro Leu Ala
                355                 360                 365

Gly Ser Pro Val Ile Ala Ala Asn Pro Leu Gly Met Pro Val Pro
            370                 375                 380

Ala Ala Ala Gly Ala Gln Gln
385                 390
```

<210> SEQ ID NO 3
<211> LENGTH: 255
<212> TYPE: PRT
<213> ORGANISM: Homo sapiens

<400> SEQUENCE: 3

```
Met Tyr Glu Ile Leu Lys Ala Leu Asp Tyr Cys His Ser Met Gly Ile
1               5                   10                  15

Met His Arg Asp Val Lys Pro His Asn Val Met Ile Asp His Glu His
                20                  25                  30

Arg Lys Leu Arg Leu Ile Asp Trp Gly Leu Ala Glu Phe Tyr His Pro
            35                  40                  45

Gly Gln Glu Tyr Asn Val Arg Val Ala Ser Arg Tyr Phe Lys Gly Pro
        50                  55                  60

Glu Leu Leu Val Asp Tyr Gln Met Tyr Asp Tyr Ser Leu Asp Met Trp
65                  70                  75                  80

Ser Leu Gly Cys Met Leu Ala Ser Met Ile Phe Arg Lys Glu Pro Phe
                85                  90                  95

Phe His Gly His His Asp Asn Tyr Asp Gln Leu Val Arg Ile Ala Lys Val
                100                 105                 110

Leu Gly Thr Glu Asp Leu Tyr Asp Tyr Ile Asp Lys Tyr Asn Ile Glu
            115                 120                 125

Leu Asp Pro Arg Phe Asn Asp Ile Leu Gly Arg His Ser Arg Lys Arg
130                 135                 140

Trp Glu Arg Phe Val His Ser Glu Asn Gln His Leu Val Ser Pro Glu
145                 150                 155                 160

Ala Leu Asp Phe Leu Asp Lys Leu Leu Arg Tyr Asp His Gln Ser Arg
                165                 170                 175

Leu Thr Ala Arg Glu Ala Met Glu His Pro Tyr Phe Tyr Thr Val Val
            180                 185                 190

Lys Asp Gln Ala Arg Met Gly Ser Ser Ser Met Pro Gly Gly Ser Thr
        195                 200                 205

Pro Val Ser Ser Ala Asn Met Met Ser Gly Ile Ser Ser Val Pro Thr
210                 215                 220

Pro Ser Pro Leu Gly Pro Leu Ala Gly Ser Pro Val Ile Ala Ala Ala
225                 230                 235                 240

Asn Pro Leu Gly Met Pro Val Pro Ala Ala Ala Gly Ala Gln Gln
                245                 250                 255
```

<210> SEQ ID NO 4
<211> LENGTH: 10
<212> TYPE: PRT
<213> ORGANISM: Unknown
<220> FEATURE:

```
<223> OTHER INFORMATION: Substrate peptide

<400> SEQUENCE: 4

Arg Arg Arg Asp Asp Asp Ser Asp Asp Asp
1               5                   10

<210> SEQ ID NO 5
<211> LENGTH: 9
<212> TYPE: PRT
<213> ORGANISM: Unknown
<220> FEATURE:
<223> OTHER INFORMATION: Substrate peptide

<400> SEQUENCE: 5

Lys Lys Arg Asn Arg Thr Leu Thr Lys
1               5

<210> SEQ ID NO 6
<211> LENGTH: 10
<212> TYPE: PRT
<213> ORGANISM: Unknown
<220> FEATURE:
<223> OTHER INFORMATION: Substrate peptide

<400> SEQUENCE: 6

Arg Ser Arg Ser Ser Tyr Pro Ala Gly Thr
1               5                   10
```

PYRAZOLOPYRIMIDINES AND RELATED HETEROCYCLES AS KINASE INHIBITORS

RELATED APPLICATIONS

This application claims benefit of priority from U.S. Provisional Application Ser. No. 61/180,090, filed May 20, 2009, and U.S. Provisional Application Ser. No. 61/218,318, filed Jun. 18, 2009. The contents of each of these applications is incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: CYLE_051_02US_SeqList_ST25.txt, date recorded: Aug. 31, 2010, file size 10 -kilobytes).

FIELD OF THE INVENTION

The invention relates in part to molecules having certain biological activities that include, but are not limited to, inhibiting cell proliferation, and modulating certain protein kinase activities. Molecules of the invention can modulate casein kinase activity (e.g., CK2 activity) and/or Pim kinase activity (e.g., PIM-1 activity), and are useful to treat cancers and inflammatory conditions as well as certain infectious disorders. The invention also relates in part to methods for using such compounds, and pharmaceutical compositions containing these compounds.

BACKGROUND

Protein kinase CK2 (formerly called Casein kinase II, referred to herein as "CK2") is a ubiquitous and highly conserved protein serine/threonine kinase. The holoenzyme is typically found in tetrameric complexes consisting of two catalytic (alpha and/or alpha') subunits and two regulatory (beta) subunits. CK2 has a number of physiological targets and participates in a complex series of cellular functions including the maintenance of cell viability. The level of CK2 in normal cells is tightly regulated, and it has long been considered to play a role in cell growth and proliferation Inhibitors of CK2 that are useful for treating certain types of cancers are described in PCT/US2007/077464, PCT/US2008/074820, PCT/US2009/35609.

Both the prevalence and the importance of CK2 suggest it is an ancient enzyme on the evolutionary scale, as does an evolutionary analysis of its sequence; its longevity may explain why it has become important in so many biochemical processes, and why CK2 from hosts have even been co-opted by infectious pathogens (e.g., viruses, protozoa) as an integral part of their survival and life cycle biochemical systems. These same characteristics explain why inhibitors of CK2 are believed to be useful in a variety of medical treatments as discussed herein. Because it is central to many biological processes, as summarized by Guerra & Issinger, Curr. Med. Chem., 2008, 15:1870-1886, inhibitors of CK2, including the compounds described herein, should be useful in the treatment of a variety of diseases and disorders.

Cancerous cells show an elevation of CK2, and recent evidence suggests that CK2 exerts potent suppression of apoptosis in cells by protecting regulatory proteins from caspase-mediated degradation. The anti-apoptotic function of CK2 may contribute to its ability to participate in transformation and tumorigenesis. In particular, CK2 has been shown to be associated with acute and chronic myelogenous leukemia, lymphoma and multiple myeloma. In addition, enhanced CK2 activity has been observed in solid tumors of the colon, rectum and breast, squamous cell carcinomas of the lung and of the head and neck (SCCHN), adenocarcinomas of the lung, colon, rectum, kidney, breast, and prostate Inhibition of CK2 by a small molecule is reported to induce apoptosis of pancreatic cancer cells, and hepatocellular carcinoma cells (HegG2, Hep3, HeLa cancer cell lines); and CK2 inhibitors dramatically sensitized RMS (Rhabdomyosarcoma) tumors toward apoptosis induced by TRAIL. Thus an inhibitor of CK2 alone, or in combination with TRAIL or a ligand for the TRAIL receptor, would be useful to treat RMS, the most common soft-tissue sarcoma in children. In addition, elevated CK2 has been found to be highly correlated with aggressiveness of neoplasias, and treatment with a CK2 inhibitor of the invention should thus reduce tendency of benign lesions to advance into malignant ones, or for malignant ones to metastasize.

Unlike other kinases and signaling pathways, where mutations are often associated with structural changes that cause loss of regulatory control, increased CK2 activity level appears to be generally caused by upregulation or overexpression of the active protein rather than by changes that affect activation levels. Guerra and Issinger postulate this may be due to regulation by aggregation, since activity levels do not correlate well with mRNA levels. Excessive activity of CK2 has been shown in many cancers, including SCCHN tumors, lung tumors, breast tumors, and others. Id.

Elevated CK2 activity in colorectal carcinomas was shown to correlate with increased malignancy. Aberrant expression and activity of CK2 have been reported to promote increase nuclear levels of NF-kappaB in breast cancer cells. CK2 activity is markedly increased in patients with AML and CML during blast crisis, indicating that an inhibitor of CK2 should be particularly effective in these conditions. Multiple myeloma cell survival has been shown to rely on high activity of CK2, and inhibitors of CK2 were cytotoxic to MM cells. Similarly, a CK2 inhibitor inhibited growth of murine p190 lymphoma cells. Its interaction with Bcr/Abl has been reported to play an important role in proliferation of Bcr/Abl expressing cells, indicating inhibitors of CK2 may be useful in treatment of Bcr/Abl-positive leukemias. Inhibitors of CK2 have been shown to inhibit progression of skin papillomas, prostate and breast cancer xenografts in mice, and to prolong survival of transgenic mice that express prostate-promoters. Id.

The role of CK2 in various non-cancer disease processes has been recently reviewed. See Guerra & Issinger, Curr. Med. Chem., 2008, 15:1870-1886. Increasing evidence indicates that CK2 is involved in critical diseases of the central nervous system, including, for example, Alzheimer's disease, Parkinson's disease, and rare neurodegenerative disorders such as Guam-Parkinson dementia, chromosome 18 deletion syndrome, progressive supranuclear palsy, Kuf's disease, or Pick's disease. It is suggested that selective CK2-mediated phosphorylation of tau proteins may be involved in progressive neurodegeneration of Alzheimer's. In addition, recent studies suggest that CK2 plays a role in memory impairment and brain ischemia, the latter effect apparently being mediated by CK2's regulatory effect on the PI3K survival pathways.

CK2 has also been shown to be involved in the modulation of inflammatory disorders, for example, acute or chronic inflammatory pain, glomerulonephritis, and autoimmune diseases, including, e.g., multiple sclerosis (MS), systemic lupus erythematosus, rheumatoid arthritis, and juvenile arthritis. It positively regulates the function of the serotonin 5-HT3 receptor channel, activates heme oxygenase type 2, and enhances the activity of neuronal nitric oxide synthase. A selective CK2 inhibitor was reported to strongly reduce pain response of mice when administered to spinal cord tissue prior to pain testing. It phosphorylates secretory type IIA phospholipase A2 from synovial fluid of RA patients, and modulates secretion of DEK (a nuclear DNA-binding protein), which is a proinflammatory molecule found in synovial fluid of patients with juvenile arthritis. Thus inhibition of CK2 is expected to control progression of inflammatory pathologies such as those described here, and the inhibitors disclosed herein have been shown to effectively treat pain in animal models.

Protein kinase CK2 has also been shown to play a role in disorders of the vascular system, such as, e.g., atherosclerosis, laminar shear stress, and hypoxia. CK2 has also been shown to play a role in disorders of skeletal muscle and bone tissue, such as cardiomyocyte hypertrophy, impaired insulin signaling and bone tissue mineralization. In one study, inhibitors of CK2 were effective at slowing angiogenesis induced by growth factor in cultured cells. Moreover, in a retinopathy model, a CK2 inhibitor combined with octreotide (a somatostatin analog) reduced neovascular tufts; thus the CK2 inhibitors described herein would be effective in combination with a somatostatin analog to treat retinopathy.

CK2 has also been shown to phosphorylate GSK, troponin and myosin light chain; thus it is important in skeletal muscle and bone tissue physiology, and is linked to diseases affecting muscle tissue.

Evidence suggests that CK2 is also involved in the development and life cycle regulation of protozoal parasites, such as, for example, *Theileria parva, Trypanosoma cruzi, Leishmania donovani, Herpetomonas muscarum muscarum, Plasmodium falciparum, Trypanosoma brucei, Toxoplasma gondii* and *Schistosoma mansoni*. Numerous studies have confirmed the role of CK2 in regulation of cellular motility of protozoan parasites, essential to invasion of host cells. Activation of CK2 or excessive activity of CK2 has been shown to occur in hosts infected with *Leishmania donovani, Herpetomonas muscarum muscarum, Plasmodium falciparum, Trypanosoma brucei, Toxoplasma gondii* and *Schistosoma mansoni*. Indeed, inhibition of CK2 has been shown to block infection by *T. cruzi*.

CK2 has also been shown to interact with and/or phosphorylate viral proteins associated with human immunodeficiency virus type 1 (HIV-1), human papilloma virus, and herpes simplex virus, in addition to other virus types (e.g. human cytomegalovirus, hepatitis C and B viruses, Borna disease virus, adenovirus, coxsackievirus, coronavirus, influenza, and varicella zoster virus). CK2 phosphorylates and activates HIV-1 reverse transcriptase and proteases in vitro and in vivo, and promotes pathogenicity of simian-human immunodeficiency virus (SHIV), a model for HIV Inhibitors of CK2 are thus able to reduce reduce pathogenic effects of a model of HIV infection. CK2 also phosphorylates numerous proteins in herpes simplex virus and numerous other viruses, and some evidence suggests viruses have adopted CK2 as a phosphorylating enzyme for their essential life cycle proteins Inhibition of CK2 is thus expected to deter infection and progression of viral infections, which rely upon the host's CK2 for their own life cycles.

CK2 is unusual in the diversity of biological processes that it affects, and it differs from most kinases in other ways as well: it is constitutively active, it can use ATP or GTP, and it is elevated in most tumors and rapidly proliferating tissues. It also has unusual structural features that may distinguish it from most kinases, too, enabling its inhibitors to be highly specific for CK2 while many kinase inhibitors affect multiple kinases, increasing the likelihood of off-target effects, or variability between individual subjects. For all of these reasons, CK2 is a particularly interesting target for drug development, and the invention provides highly effective inhibitors of CK2 that are useful in treating a variety of different diseases and disorders mediated by or associated with excessive, aberrant or undesired levels of CK2 activity.

The PIM protein kinases which include the closely related PIM-1, -2, and -3, have been implicated in diverse biological processes such as cell survival, proliferation, and differentiation. PIM-1 is involved in a number of signaling pathways that are highly relevant to tumorigenesis [reviewed in Bachmann & Moroy, *Internat. J. Biochem. Cell Biol.*, 37, 726-730 (2005)]. Many of these are involved in cell cycle progression and apoptosis. It has been shown that PIM-1 acts as an anti-apoptotic factor via inactivation of the pro-apoptotic factor BAD (Bcl2 associated death promoter, an apoptosis initiator). This finding suggested a direct role of PIM-1 in preventing cell death, since the inactivation of BAD can enhance Bcl-2 activity and can thereby promote cell survival [Aho et al., *FEBS Letters*, 571, 43-49 (2004)]. PIM-1 has also been recognized as a positive regulator of cell cycle progression. PIM-1 binds and phosphorylates Cdc25A, which leads to an increase in its phosphatase activity and promotion of G1/S transition [reviewed in Losman et al., *JBC*, 278, 4800-4805 (1999)]. In addition, the cyclin kinase inhibitor p21$^{Waf}$ which inhibits G1/S progression, was found to be inactivated by PIM-1 [Wang et al., *Biochim. Biophys. Acta.* 1593, 45-55 (2002)]. Furthermore, by means of phosphorylation, PIM-1 inactivates C-TAK1 and activates Cdc25C which results in acceleration of G2/M transition [Bachman et al., *JBC*, 279, 48319-48 (2004)].

PIM-1 appears to be an essential player in hematopoietic proliferation. Kinase active PIM-1 is required for the gp130-mediated STATS proliferation signal [Hirano et al., *Oncogene* 19, 2548-2556, (2000)]. PIM-1 is overexpressed or even mutated in a number of tumors and different types of tumor cell lines and leads to genomic instability. Fedorov, et al., concluded that a Phase III compound in development for treating leukemia, LY333'531, is a selective PIM-1 inhibitor. O. Fedorov, et al., *PNAS* 104(51), 20523-28 (December 2007). Evidence has been published to show that PIM-1 is involved in human tumors including prostate cancer, oral cancer, and Burkitt lymphoma (Gaidano & Dalla Faver, 1993). All these findings point to an important role of PIM-1 in the initiation and progression of human cancers, including various tumors and hematopoietic cancers, thus small molecule inhibitors of PIM-1 activity are a promising therapeutic strategy.

Additionally, PIM-2 and PIM-3 have overlapping functions with PIM-1 and inhibition of more than one isoform may provide additional therapeutic benefits. However, it is sometimes preferable for inhibitors of PIM to have little or no in vivo impact through their inhibition of various other kinases, since such effects are likely to cause side effects or unpredictable results. See, e.g., O. Fedorov, et al., *PNAS* 104(51), 20523-28 (December 2007), discussing the effects that non-specific kinase inhibitors can produce. Accordingly, in some embodiments, the invention provides compounds that are selective inhibitors of at least one of PIM-1, PIM-2, and PIM-3, or some combination of these, while having substantially less activity on certain other human kinases, as described further herein, although the compounds of Formula I are typically active on CK2 as well as one or more Pim proteins. In some embodiments, the compounds exhibit IC-50's less than 1 micromolar on both PIM and CK2 kinases.

The implication of a role for PIM-3 in cancer was first suggested by transcriptional profiling experiments showing that PIM3 gene transcription was upregulated in EWS/ETS-induced malignant transformation of NIH 3T3 cells. These results were extended to show that PIM-3 is selectively expressed in human and mouse hepatocellular and pancreatic carcinomas but not in normal liver or pancreatic tissues. In addition, PIM-3 mRNA and protein are constitutively expressed in multiple human pancreatic and hepatocellular cancer cell lines.

The link between PIM-3 overexpression and a functional role in promoting tumorigenesis came from RNAi studies in human pancreatic and hepatocellular cancer cell lines over-expressing PIM-3. In these studies the ablation of endogenous PIM-3 protein promoted apoptosis of these cells. The molecular mechanism by which PIM-3 suppresses apoptosis is in part carried out through the modulation of phosphorylation of the pro-apoptotic protein BAD. Similar to both PIM-1 & 2 which phosphorylate BAD protein, the knockdown of PIM-3 protein by siRNA results in a decrease in BAD phosphorylation at Ser112. Thus, similar to PIM-1 and 2, PIM-3 acts a suppressor of apoptosis in cancers of endodermal origin, e.g., pancreatic and liver cancers. Moreover, as conventional therapies in pancreatic cancer have a poor clinical outcome, PIM-3 could represent a new important molecular target towards successful control of this incurable disease.

At the 2008 AACR Annual Meeting, SuperGen announced that it has identified a lead PIM kinase inhibitor, SGI-1776, that causes tumor regression in acute myelogenous leukemia (AML) xenograft models (Abstract No. 4974). In an oral presentation entitled, "A potent small molecule PIM kinase inhibitor with activity in cell lines from hematological and solid malignancies," Dr. Steven Warner detailed how scientists used SuperGen's CLIMB™ technology to build a model that allowed for the creation of small molecule PIM kinase inhibitors. SGI-1776 was identified as a potent and selective inhibitor of the PIM kinases, inducing apoptosis and cell cycle arrest, thereby causing a reduction in phospho-BAD levels and enhancement of mTOR inhibition in vitro. Most notably, SGI-1776 induced significant tumor regression in MV-4-11 (AML) and MOLM-13 (AML) xenograft models. This demonstrates that inhibitors of PIM kinases can be used to treat leukemias.

Fedorov, et al., in *PNAS vol.* 104(51), 20523-28, showed that a selective inhibitor of PIM-1 kinase (Ly5333'531) suppressed cell growth and induced cell death in leukemic cells from AML patients. PIM-3 has been shown to be expressed in pancreatic cancer cells, while it is not expressed in normal pancreas cells, demonstrating that it should be a good target for pancreatic cancer. Li, et al., *Cancer Res.* 66(13), 6741-47 (2006) Inhibitors of PIM kinases that are described as useful for treating certain types of cancers are described in PCT/US2008/012829.

Because these two protein kinases have important functions in biochemical pathways associated with cancer and inflammation, and are also important in pathogenicity of many microorganisms, inhibitors of their activity have many medicinal applications. The present invention provides novel compounds that inhibit CK2 or PIM or both, as well as compositions and methods of use utilizing these compounds.

DISCLOSURE OF THE INVENTION

The present invention in part provides chemical compounds having certain biological activities that include, but are not limited to, inhibiting cell proliferation, inhibiting angiogenesis, and modulating protein kinase activities. These molecules modulate casein kinase 2 (CK2) activity and/or Pim kinase activity, and thus affect biological functions that include but are not limited to, inhibiting gamma phosphate transfer from ATP to a protein or peptide substrate, inhibiting angiogenesis, inhibiting cell proliferation and inducing cell apoptosis, for example. The present invention also in part provides methods for preparing novel chemical compounds, and analogs thereof, and methods of using these compounds. Also provided are compositions comprising the above-described molecules in combination with other materials, including other therapeutic agents, and methods for using such compositions.

The compounds of the invention have the general formula (I):

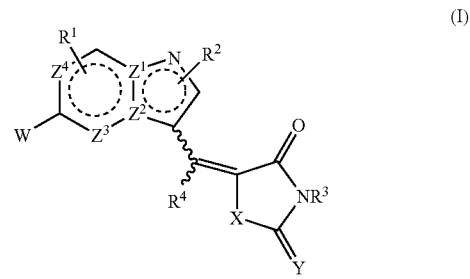

wherein the bicyclic ring system containing $Z^1$-$Z^4$ is aromatic;
one of $Z^1$ and $Z^2$ is C, the other of $Z^1$ and $Z^2$ is N;
$Z^3$ and $Z^4$ are independently $CR^5$ or N,
where $R^5$ can be H or $R^1$;
$R^1$ is H, halo, CN, optionally substituted C1-C4 alkyl, optionally substituted C2-C4 alkenyl, optionally substituted C2-C4 alkynyl, optionally substituted aryl or heteroaryl, optionally substituted C1-C4 alkoxy, or —$NR^7R^8$, where $R^7$ and $R^8$ are independently selected from H, optionally substituted C1-C10 alkyl, optionally substituted aryl, optionally substituted arylalkyl, optionally substituted heteroaryl, and optionally substituted heteroarylalkyl,
or $R^7$ and $R^8$ taken together with the N of —$NR^7R^8$ can form an optionally substituted 5-8 membered ring that optionally contains an additional heteroatom selected from N, O and S as a ring member;
$R^2$ is H, halo, CN, or an optionally substituted group selected from C1-C4 alkyl, C2-C4 alkenyl, and C2-C4 alkynyl;
$R^3$ and $R^4$ are independently selected from H and optionally substituted C1-C10 alkyl;
X is $NR^6$, O, or S, where $R^6$ is H or an optionally substituted group selected from C1-C4 alkyl, C2-C4 alkenyl, and C2-C4 alkynyl;
Y is O or S or $NR^{10}$;
$R^{10}$ is selected from H, CN, optionally substituted C1-C4 alkyl, optionally substituted C2-C4 alkenyl, optionally substituted C2-C4 alkynyl, optionally substituted C1-C4 alkoxy, or —$NR^7R^8$, where $R^7$ and $R^8$ are independently selected from H, optionally substituted C1-C10 alkyl, optionally substituted aryl, optionally substituted arylalkyl, optionally substituted heteroaryl, and optionally substituted heteroarylalkyl,
or $R^7$ and $R^8$ taken together with the N of —$NR^7R^8$ can form an optionally substituted 5-8 membered ring that optionally contains an additional heteroatom selected from N, O and S as a ring member;

W is optionally substituted aryl, optionally substituted heteroaryl, or —$NR^7R^8$, —$OR^7$, $S(O)_nR^7$, optionally substituted heterocyclyl, optionally substituted C3-C8 cycloalkyl, or $CR^7R^8R^9$, wherein n is 0, 1 or 2, and $R^7$ and $R^8$ and $R^9$ are independently selected from H, optionally substituted C1-C10 alkyl, optionally substituted aryl, optionally substituted arylalkyl, optionally substituted heteroaryl, and optionally substituted heteroarylalkyl;

and wherein $R^7$ and $R^8$ in $NR^7R^8$ can be taken together along with N to form a 5-8 membered ring that can be optionally substituted, and can contain an additional heteroatom selected from N, O and S as a ring member.

The invention also includes the pharmaceutically acceptable salts of compounds of formula (I).

In certain embodiments, the invention provides compounds of Formula Ia or Formula Ib:

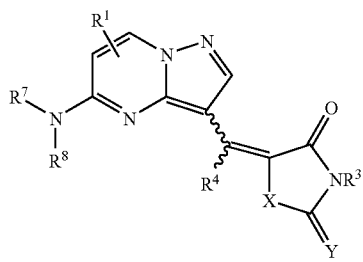

Ia

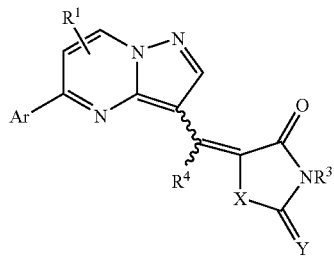

Ib where $R^1$, $R^3$, $R^4$, $R^7$, $R^8$ X and Y are as defined for Formula I, and Ar is optionally substituted aryl; as well as the pharmaceutically acceptable salts of these compounds.

The invention also provides pharmaceutical compositions containing such compounds plus one or more pharmaceutically acceptable carriers or excipients, and methods of using these compounds and compositions for the treatment of specified conditions as further described herein.

Also provided herein are pharmaceutical compositions comprising a compound of Formula I as described herein and at least one pharmaceutically acceptable carrier or excipient, or two or more pharmaceutically acceptable carriers and/or excipients. It is understood that the compounds of Formula I can include compounds of Formula Ia and Formula Ib. Pharmaceutical compositions comprising at least one of these compounds can be utilized in methods of treatment such as those described herein.

The compounds of Formula I bind to certain kinase proteins, which are believed to be the basis for their pharmaceutical activity. In certain embodiments, the protein is a CK2 protein, such as a CK2 protein comprising the amino acid sequence of SEQ ID NO:1, 2 or 3 or a substantially identical variant thereof, for example.

SEQ ID NO:1 (NP_001886; Casein Kinase II Alpha 1 Subunit Isoform a [*Homo sapiens*])

```
    MSGPVPSRAR VYTDVNTHRP REYWDYESHV VEWGNQDDYQ LVRKLGRGKY SEVFEAINIT
    NNEKVVVKIL KPVKKKKIKR EIKILENLRG GPNIITLADI VKDPVSRTPA LVFEHVNNTD
121 FKQLYQTLTD YDIRFYMYEI LKALDYCHSM GIMHRDVKPH NVMIDHEHRK LRLIDWGLAE
181 FYHPGQEYNV RVASRYFKGP ELLVDYQMYD YSLDMWSLGC MLASMIFRKE PFFHGHDNYD
241 QLVRIAKVLG TEDLYDYIDK YNIELDPRFN DILGRHSRKR WERFVHSENQ HLVSPEALDF
301 LDKLLRYDHQ SRLTAREAME HPYFYTVVKD QARMGSSSMP GGSTPVSSAN MMSGISSVPT
361 PSPLGPLAGS PVIAAANPLG MPVPAAAGAQ Q
```

SEQ ID NO:2 (NP_808227; Casein Kinase II Alpha 1 Subunit Isoform a [*Homo sapiens*])

```
    MSGPVPSRAR VYTDVNTHRP REYWDYESHV VEWGNQDDYQ LVRKLGRGKY SEVFEAINIT
    NNEKVVVKIL KPVKKKKIKR EIKILENLRG GPNIITLADI VKDPVSRTPA LVFEHVNNTD
121 FKQLYQTLTD YDIRFYMYEI LKALDYCHSM GIMHRDVKPH NVMIDHEHRK LRLIDWGLAE
181 FYHPGQEYNV RVASRYFKGP ELLVDYQMYD YSLDMWSLGC MLASMIFRKE PFFHGHDNYD
241 QLVRIAKVLG TEDLYDYIDK YNIELDPRFN DILGRHSRKR WERFVHSENQ HLVSPEALDF
301 LDKLLRYDHQ SRLTAREAME HPYFYTVVKD QARMGSSSMP GGSTPVSSAN MMSGISSVPT
361 PSPLGPLAGS PVIAAANPLG MPVPAAAGAQ Q
```

SEQ ID NO:3 (NP_808228; Casein Kinase II Alpha 1 Subunit Isoform b [*Homo sapiens*])

```
    MYEILKALDY CHSMGIMHRD VKPHNVMIDH EHRKLRLIDW GLAEFYHPGQ EYNVRVASRY

FKGPELLVDY QMYDYSLDMW SLGCMLASMI FRKEPFFHGH DNYDQLVRIA KVLGTEDLYD

121 YIDKYNIELD PRFNDILGRH SRKRWERFVH SENQHLVSPE ALDFLDKLLR YDHQSRLTAR

181 EAMEHPYFYT VVKDQARMGS SSMPGGSTPV SSANMMSGIS SVPTPSPLGP LAGSPVIAAA

241 NPLGMPVPAA AGAQQ
```

Substantially identical variants of these include proteins having at least 90% sequence homology with one of these, preferably at least 90% sequence identity; and having at least 50% of the level of in vitro kinase activity of the specified sequence under typical assay conditions.

The invention includes methods to modulate the activity of CK2 protein, either in vitro or ex vivo. Suitable methods comprise contacting a system comprising the protein with a compound described herein in an amount effective for modulating the activity of the protein. In certain embodiments the activity of the protein is inhibited, and sometimes the protein is a CK2 protein comprising the amino acid sequence of SEQ ID NO:1, 2 or 3 or a substantially identical variant thereof, for example. In certain embodiments the CK2 is in a cell or tissue; in other embodiments, it can be in a cell-free system.

Also provided are methods for modulating the activity of a Pim protein, which comprise contacting a system comprising the protein with a compound described herein in an amount effective for modulating the activity of the protein. In certain embodiments, the system is a cell, and in other embodiments the system is a cell-free system. In certain embodiments, the activity of the Pim protein is inhibited.

Provided also are methods for inhibiting cell proliferation, which comprise contacting cells with a compound described herein in an amount effective to inhibit proliferation of the cells. The cells sometimes are in a cell line, such as a cancer cell line (e.g., breast cancer, prostate cancer, pancreatic cancer, lung cancer, hemopoietic cancer, colorectal cancer, skin cancer, ovary cancer cell line), for example. In some embodiments, the cancer cell line is a breast cancer, prostate cancer or pancreatic cancer cell line. The cells sometimes are in a tissue, can be in a subject, at times are in a tumor, and sometimes are in a tumor in a subject. In certain embodiments, the method further comprises inducing cell apoptosis. Cells sometimes are from a subject having macular degeneration.

Also provided are methods for treating a condition related to aberrant cell proliferation, which comprise administering a compound described herein to a subject in need thereof in an amount effective to treat the cell proliferative condition. In certain embodiments the cell proliferative condition is a tumor-associated cancer. The cancer sometimes is cancer of the breast, prostate, pancreas, lung, colorectum, skin, or ovary. In some embodiments, the cell proliferative condition is a non-tumor cancer, such as a hematopoietic cancer, for example, including leukemias and lymphomas. The cell proliferative condition is macular degeneration in some embodiments.

The invention also includes methods for treating cancer or an inflammatory disorder in a subject in need of such treatment, comprising: administering to the subject a therapeutically effective amount of a therapeutic agent useful for treating such disorder; and administering to the subject a molecule that inhibits CK2 and/or Pim in an amount that is effective to enhance a desired effect of the therapeutic agent. In certain embodiments, the molecule that inhibits CK2 and/or Pim is a compound of Formula I, including compounds of Formula Ia and Ib, or a pharmaceutically acceptable salt thereof. In certain embodiments, the desired effect of the therapeutic agent that is enhanced by the molecule that inhibits CK2 and/or Pim is an increase in apoptosis in at least one type of cell.

In some embodiments, the therapeutic agent and the molecule that inhibits CK2 and/or Pim are administered at substantially the same time. The therapeutic agent and molecule that inhibits CK2 and/or Pim sometimes are used concurrently by the subject. The therapeutic agent and the molecule that inhibits CK2 and/or Pim can be combined into one pharmaceutical composition in certain embodiments; in other embodiments that are administered as separate compositions.

Also provided are compositions of matter comprising a compound described herein and an isolated protein. The protein sometimes is a CK2 protein, such as a CK2 protein comprising the amino acid sequence of SEQ ID NO:1, 2 or 3 or a substantially identical variant thereof, for example. In some embodiments, the protein is a Pim protein. Certain compositions comprise a compound described herein in combination with a cell. The cell may be from a cell line, such as a cancer cell line. In the latter embodiments, the cancer cell line is sometimes a breast cancer, prostate cancer, pancreatic cancer, lung cancer, hematopoietic cancer, colorectal cancer, skin cancer, of ovary cancer cell line.

These and other embodiments of the invention are described in the description that follows.

MODES OF CARRYING OUT THE INVENTION

Compounds of Formula I exert biological activities that include, but are not limited to, inhibiting cell proliferation, reducing angiogenesis, preventing or reducing inflammatory responses and pain, and modulating certain immune responses. Compounds of this Formula can modulate CK2 activity, Pim activity or both, as demonstrated by the data herein. Such compounds therefore can be utilized in multiple applications by a person of ordinary skill in the art. For example, compounds described herein can be used, for example, for (i) modulation of protein kinase activity (e.g., CK2 activity), (ii) modulation of Pim activity (e.g., PIM-1 activity), (iii) modulation of cell proliferation, (iv) modulation of apoptosis, and (v) treatments of cell proliferation related disorders (e.g., administration alone or co-administration with another molecule).

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed, including both E and Z isomers of double bonds that are not in rings. The compounds of the invention may also exist in more than one tautomeric form; the depiction herein of one tautomer is for convenience only, and is also understood to encompass other tautomers of the form shown.

As an example, only, the compounds of Formula I have a Carbon-Carbon double bond to which group $R^4$ is attached. The Formula is depicted to indicate it can represent either the E isomer or the Z isomer, or both. Other structures may appear to depict a specific isomer, but that is merely for convenience, and is not intended to limit the invention to the depicted olefin isomer.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the backbone of the ring or chain being described.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often optionally substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, $NRCSNR_2$, NRC(=NR)$NR_2$, NRCOOR, NRCOR, CN, C≡CR, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, NR'C(=NR')$NR'_2$, NR'COOR', NR'COR', CN, C≡CR', COOR', $CONR'_2$, OOCR', COR', and $NO_2$, wherein each R' is independently H, C1-C8 alkyl, C2-C8 heteroalkyl, C1-C8 acyl, C3-C8 heterocyclyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl, C3-C8 cycloalkyl, C3-C8 heterocyclyl, or C5-C10 heteroaryl, each of which can be substituted by the substituents that are appropriate for the particular group. Where a substituent group contains two R or R' groups on the same or adjacent atoms (e.g., —$NR_2$, or —NR—C(O)R), the two R or R' groups can optionally be taken together with the atoms in the substituent group to which they are attached to form a ring having 5-8 ring members, which can be substituted as allowed for the R or R' itself, and can contain an additional heteroatom (N, O or S) as a ring member.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Acetylene" substituents are 2-10C alkynyl groups that are optionally substituted, and are of the formula —C≡C—$R^a$, wherein $R^a$ is H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and each $R^a$ group is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, NR'C(=NR')$NR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O; and wherein two R' can be linked to form a 3-7 membered ring optionally containing up to three heteroatoms selected from N, O and S. In some embodiments, $R^a$ of —C≡C—$R^a$ is H or Me.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCSNR$_2$, NRC(=NR)NR$_2$, NRCOOR, NRCOR, CN, C≡CR, COOR, CONR$_2$, OOCR, COR, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups. Where a substituent group contains two R or R' groups on the same or adjacent atoms (e.g., —NR2, or —NR—C(O)R), the two R or R' groups can optionally be taken together with the atoms in the substituent group to which the are attached to form a ring having 5-8 ring members, which can be substituted as allowed for the R or R' itself, and can contain an additional heteroatom (N, O or S) as a ring member.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Halo", as used herein includes fluoro, chloro, bromo and iodo. Fluoro and chloro are often preferred.

"Amino" as used herein refers to $NH_2$, but where an amino is described as "substituted" or "optionally substituted", the term includes NR'R'' wherein each R' and R'' is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R'' are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R'' is an aromatic group, it is optionally substituted with the substituents described as typical for heteroaryl groups.

As used herein, the term "carbocycle" or "carbocyclic" refers to a cyclic ring containing only carbon atoms in the ring, whereas the term "heterocycle" or "heterocyclic" refers to a ring comprising a heteroatom. The carbocyclic and heterocyclic structures encompass compounds having monocyclic, bicyclic or multiple ring systems.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S.

Illustrative examples of heterocycles include but are not limited to tetrahydrofuran, 1,3-dioxolane, 2,3-dihydrofuran, pyran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4 b]pyridine, piperazine, pyrazine, morpholine, thiomorpholine, imidazole, imidazolidine 2,4-dione, 1,3-dihydrobenzimidazol-2-one, indole, thiazole, benzothiazole, thiadiazole, thiophene, tetrahydrothiophene 1,1-dioxide, diazepine, triazole, guanidine, diazabicyclo[2.2.1]heptane, 2,5-diazabicyclo[2.2.1]heptane, 2,3,4,4a,9,9a-hexahydro-1H-β-carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

The invention provides compounds of Formula I:

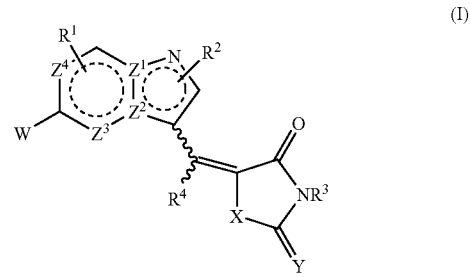

(I)

wherein the bicyclic ring system containing $Z^1$-$Z^4$ is aromatic;
one of $Z^1$ and $Z^2$ is C, the other of $Z^1$ and $Z^2$ is N;
$Z^3$ and $Z^4$ are independently $CR^5$ or N,
where $R^5$ can be H or $R^1$;
$R^1$ is H, halo, CN, optionally substituted C1-C4 alkyl, optionally substituted C2-C4 alkenyl, optionally substituted C2-C4 alkynyl, optionally substituted aryl or heteroaryl, optionally substituted C1-C4 alkoxy, or —$NR^7R^8$, where $R^7$ and $R^8$ are independently selected from H, optionally substituted C1-C10 alkyl, optionally substituted aryl, optionally substituted arylalkyl, optionally substituted heteroaryl, and optionally substituted heteroarylalkyl,
or $R^7$ and $R^8$ taken together with the N of —$NR^7R^8$ can form an optionally substituted 5-8 membered ring that optionally contains an additional heteroatom selected from N, O and S as a ring member;
$R^2$ is H, halo, CN, or an optionally substituted group selected from C1-C4 alkyl, C2-C4 alkenyl, and C2-C4 alkynyl;
$R^3$ and $R^4$ are independently selected from H and optionally substituted C1-C10 alkyl;
X is $NR^6$, O, or S, where $R^6$ is H or an optionally substituted group selected from C1-C4 alkyl, C2-C4 alkenyl, and C2-C4 alkynyl;
Y is O or S or $NR^{10}$;
$R^{10}$ is selected from H, CN, optionally substituted C1-C4 alkyl, optionally substituted C2-C4 alkenyl, optionally substituted C2-C4 alkynyl, optionally substituted C1-C4 alkoxy, or —$NR^7R^8$, where $R^7$ and $R^8$ are independently selected from H, optionally substituted C1-C10 alkyl, optionally substituted aryl, optionally substituted arylalkyl, optionally substituted heteroaryl, and optionally substituted heteroarylalkyl,
or $R^7$ and $R^8$ taken together with the N of —$NR^7R^8$ can form an optionally substituted 5-8 membered ring that optionally contains an additional heteroatom selected from N, O and S as a ring member;

W is optionally substituted aryl, optionally substituted heteroaryl, or —NR$^7$R$^8$, —OR$^7$, S(O)$_n$R$^7$, optionally substituted heterocyclyl, optionally substituted C3-C8 cycloalkyl, or CR$^7$R$^8$R$^9$,
wherein n is 0, 1 or 2, and
R$^7$ and R$^8$ and R$^9$ are independently selected from H, optionally substituted C1-C10 alkyl, optionally substituted aryl, optionally substituted arylalkyl, optionally substituted heteroaryl, and optionally substituted heteroarylalkyl;
and wherein R$^7$ and R$^8$ in NR$^7$R$^8$ can be taken together along with N to form a 5-8 membered ring that can be optionally substituted, and can contain an additional heteroatom selected from N, O and S as a ring member;
and pharmaceutically acceptable salts of these compounds.

The compounds of the invention are characterized by a bicyclic aromatic heterocyclic ring system containing two or more nitrogen atoms: one N atom is shown, and one of Z$^1$ and Z$^2$ is also N. In certain embodiments of interest, Z$^1$ is N and Z$^2$ is C; in other embodiments, Z$^1$ is C and Z$^2$ is N.

Optionally, Z$^3$ and/or Z$^4$ can also be N. In certain embodiments, they are both C; in other embodiments Z$^3$ is N and Z$^4$ is C; and in other embodiments Z$^4$ is N and Z$^3$ is C; while in other embodiments, Z$^3$ and Z$^4$ are both N. Where Z$^3$ or Z$^4$ is C, it can be CH or CR$^1$; in preferred embodiments of such compounds, Z$^3$ and/or Z$^4$ is CH.

In addition, the compounds of Formula I contain another heterocyclic group linked to the bicyclic group, and the additional heterocyclic group contains an amide linkage within the ring, plus an additional carbonyl or thiocarbonyl (C=O or C=S). The additional heterocyclic group is linked to the bicyclic group through an exocyclic methylene group (an sp$^2$ carbon) that is connected to the five-membered ring of the bicyclic group.

This additional heterocyclic group contains X, which can be NR$^6$, O or S. In certain embodiments, it is NR$^6$, and R$^6$ is often H or a small alkyl group, such as Me. Preferably, NR$^6$ is NH. In other embodiments, X is O. In certain embodiments, X is S.

This additional heterocyclic group is substituted with =Y; in some embodiments, Y is O and in some embodiments Y is S. In other embodiments, Y is NR$^{10}$, where R$^{10}$ is as defined for Formula I, and in some embodiments R$^{10}$ is selected from H and C1-C4 alkyl.

The additional heterocyclic group also contains NR$^3$, and R$^3$ in this group can be H or a small alkyl such as Me. In some embodiments, it is a substituted alkyl group such as formyl, acetyl, propionyl, benzoyl, and the like. Preferably, R$^3$ is H.

The sp$^2$ carbon connecting the two heterocyclic groups is CR$^4$, where R$^4$ can be H or a small alkyl; in preferred embodiments, it is H.

The five-membered ring of the bicyclic group is substituted by R$^2$. This can be H, halo or a small alkyl, such as Me, Et, CF$_3$, —CH$_2$OMe, vinyl, or acetylene. In preferred embodiments, R$^2$ is H.

The six-membered ring of the bicyclic group is substituted by R$^1$. This can be a variety of groups, including H, halo or an optionally substituted alkyl, aryl, amine or alkoxy group. In some embodiments, it is H, halo, or a small alkyl, such as Me, Et, CF$_3$, —CH$_2$OMe, vinyl, or acetylene. In many embodiments, R$^1$ is selected from H, optionally substituted C1-4 alkyl or C2-4 alkenyl, optionally substituted phenyl or phenylmethyl, CN, and halo. In certain embodiments, R$^1$ is H, halo, Me, OMe, NHMe, NMe$_2$, CF$_3$, or CN. In certain embodiments, R$^1$ is selected from H, F, Me, OMe, and CF$_3$, and in preferred embodiments, R$^1$ is H.

The six-membered ring of the bicyclic group is also substituted by a group W. This can represent a range of different features while retaining the desired protein kinase modulatory activities. In certain embodiments, W is an optionally substituted aryl or heteroaryl group, often selected from phenyl, pyridyl, pyrimidinyl, and pyrazinyl. In particular, it can be an optionally substituted phenyl group. In specific embodiments, W is phenyl substituted with up to two substituents; in certain embodiments, the phenyl group is substituted by at least one group other than H, such as F, Cl, Me, CF$_3$, CN, OMe, COOH, or COOMe, at the ortho or meta position relative to the point at which the phenyl is connected to the bicyclic group.

W can be an aromatic ring, preferably a phenyl ring or a 5-6 membered heteroaryl ring containing up to 3 heteroatoms selected from N, O and S as ring members, and these aromatic rings can be optionally substituted. Preferred aromatic rings for W include phenyl and thiophenyl (thienyl), which are optionally substituted. Specific embodiments of the substituted phenyl that can be W include halophenyl, such as 2-fluorophenyl or 3-fluorophenyl, 3-carboxyphenyl, and 3-(COOMe)-phenyl. Suitable thienyl rings include amides of 5-carboxythiophen-2-yl; where the amide is of the formula NHR", where R" is H or an optionally substituted C1-C8 alkyl group such as ethoxyethyl or hydroxyethyl or hydroxypropyl, or a C3-C8 cycloalkyl or cycloalkylalkyl group, such as cyclopropylmethyl.

In other embodiments, W can be a group of the formula —NR$^7$R$^8$, where R$^7$ and R$^8$ are as described above. Typically, R$^7$ and R$^8$ are not both H. In certain of these embodiments, R$^7$ is H, Me, or an acyl group such as formyl, acetyl, methoxyacetyl, benzoyl, or trifluoroacetyl; such acylated compounds may be active as kinase inhibitors, or they can serve as prodrugs for compounds wherein R$^7$ is H. In these embodiments, R$^8$ can be an optionally substituted alkyl group, or an aryl or heteroaryl group, such as phenyl, pyridinyl, pyrimidinyl, pyrazinyl, and the like, which can be optionally substituted. Suitable optionally substituted alkyl groups include C1-C6 alkyls, e.g., methyl, ethyl, butyl, propyl, isopropyl, t-butyl, fluoroethyl, methoxyethyo, isobutyl, and the like. In certain embodiments, the aryl or heteroaryl group is substituted by at least one non-H substituent group. R$^8$ can also be such an aryl or heteroaryl group that is connected to NR$^7$ through a C1-C4 alkylene chain; e.g., it can be imidazolylmethyl, phenylethyl, and the like. In specific embodiments, the aryl is phenyl, and is substituted by at least one non-H substituent, often at the position that is meta or para to the point where the phenyl is connected to the N of NR$^7$R$^8$.

The substituent(s) on this aryl or heteroaryl group can be halo, C1-C4 alkyl, or C1-C4 alkoxy groups, or aryl or heteroaryl groups such as imidazole, phenyl, pyridyl, pyrazolyl, triazolyl, and the like; or they can be C5-C8 heterocyclic groups such as morpholine, piperidine, piperazine, and the like. In some embodiments, the aryl ring (e.g., phenyl) represented by R$^8$ is substituted with a group of the formula R'$_2$N—(CH$_2$)$_p$-L-, where p is 0-3, L is a bond, O, S, or NR" (R" is H or C1-C4 alkyl), and each R' is independently H or C1-C6 alkyl that is optionally substituted, and wherein the two R' groups can optionally cyclize to form a ring, which can include an additional heteroatom (N, O or S) as a ring member. Representative examples of this version of R$^8$ include dimethylamino; 4-methylpiperazinyl; 4-morpholinyl; 4-morpholinomethyl; 4-Me-piperazinoethyl; dimethylaminomethyl; diethylaminomethyl; dimethylaminoethoxy, and the like.

Alternatively, R⁸ can be an arylalkyl or heteroarylalkyl group, such as an optionally substituted benzyl group.

Alternatively, W can be NR⁷R⁸, where R⁷ and R⁸ taken together with N form a ring, which in some embodiments is a 5-8 membered ring that can optionally contain N, O or S as an additional ring member and can be substituted. Exemplary rings include piperidine, piperazine, homopiperazine, morpholine, thiomorpholine, pyrrolidine, pyrrolidinone, and the like.

In compounds of formula I, X and Y each represent a heteroatom, and they can be the same or they can be different. In some embodiments, Y is O, while X is S or NH or NMe or O; in other embodiments, Y is S, while X is S, or NH, or NMe or O. Where X is NR⁶, R⁶ can be H, methyl, ethyl, methoxyethyl, and the like; in preferred embodiments, R⁶ is H or it is Me.

The compounds of the invention include compounds of Formula I that contain the features specifically described below, or any combination of these features.

In certain embodiments of the compounds of Formula I, $Z^1$ is N and $Z^2$ is C.

In certain embodiments of the compounds described above, $Z^3$ is N

In certain embodiments of the compounds described above, $Z^4$ is $CR^5$

In certain embodiments of the compounds described above, X is NR⁶ or S

In certain embodiments of the compounds described above, R² is H or Me

In certain embodiments of the compounds described above, R³ and R⁴ are both H.

In certain embodiments of the compounds described above, R¹ is H, Me, halo, OMe, or CF₃, or an optionally substituted benzyl or phenyl group. In some embodiments, it is selected from H, Me, halo, OMe, and CF₃; and in some preferred embodiments, R¹ is H.

In certain embodiments of the compounds described above, Y is O.

In certain embodiments of the compounds described above, Y is S.

In certain embodiments of the compounds described above, W is —NH-A, wherein A is optionally substituted phenyl. In alternative embodiments of the above compounds, W is optionally substituted aryl or optionally substituted heteroaryl. In specific embodiments of this type, W can be optionally substituted phenyl.

In one aspect, the invention provides compounds of Formula Ia or Formula Ib:

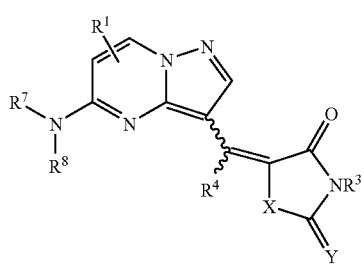

Ia

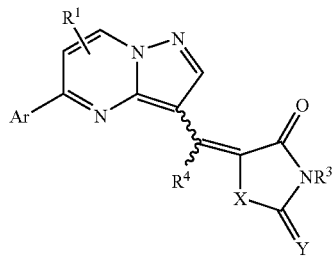

Ib wherein R¹, R³, R⁴, R⁷, R⁸, X, and Y are as defined above for Formula I, and Ar is optionally substituted aryl. In certain embodiments of Formula Ib, Ar is optionally substituted phenyl. In these embodiments, R³ and R⁴ are in some instances, selected from H and Me, and preferably both R³ and R⁴ are H. In these embodiments, R¹ can be H, Me, CF₃, CN, NH₂, NHMe, NMe₂, OMe, or halo, and is preferably H, F or Cl.

The compounds of the invention include compounds of Formula Ia or Ib that contain the features specifically described below, or any combination of these features.

In certain embodiments of these compounds, X is NR⁶ or S.

In certain embodiments of these compounds, R³ and R⁴ are both H.

In certain embodiments of these compounds, R¹ is H, Me, halo, OMe, or CF₃, or an optionally substituted benzyl or phenyl group. In some of these embodiments, R¹ is selected from H, F, Me, OMe, and CF₃, and in preferred embodiments, R¹ is H In certain embodiments of these compounds, Y is O.

In certain embodiments of these compounds, Y is S.

In certain embodiments of these compounds, NR⁷R⁸ is NHR⁸, where R⁸ is optionally substituted phenyl.

In Formula Ia, R⁷ can be H or it can be a substituted C1-C10 alkyl. Where it represents an optionally substituted alkyl, it is often Me or a C1-C6 acyl group such as formyl, acetyl, or trifluoroacetyl.

In Formula Ia, R⁸ can be an optionally substituted aryl or heteroaryl or arylalkyl or heteroarylalkyl group. In some embodiments, R⁸ is an optionally substituted phenyl pyridyl, pyrimidinyl, or pyrazinyl group. In such embodiments, R⁸ can be H.

In compounds of Formula Ib, Ar can be optionally substituted aryl group selected from phenyl, pyridyl, pyrimidinyl, pyrazinyl, thienyl (thiophene ring), furanyl, pyrazolyl, pyrrolidinyl, and the like. Preferred aromatic rings for Ar include phenyl and thiophenyl (thienyl), which are optionally substituted. Specific embodiments of the substituted phenyl that can be Ar include halophenyl, such as 2-fluorophenyl or 3-fluorophenyl, 3-carboxyphenyl, and 3-(COOMe)-phenyl. Suitable thienyl rings include amides of 5-carboxythiophen-2-yl; where the amide is of the formula NHR", where R" is H or an optionally substituted C1-C8 alkyl group such as ethoxyethyl or hydroxyethyl or hydroxypropyl, or a C3-C8 cycloalkyl or cycloalkylalkyl group, such as cyclopropylmethyl.

In compounds of Formula I, including Ia and Ib, the substituent R¹ can be at any available position on the 6-membered ring where substitution is consistent with maintaining aromaticity of the bicyclic core. In some embodiments, R¹ is at position 6 of the bicyclic ring, and in some embodiments it is at position 7 of the bicyclic ring when using the numbering convention defined herein.

The compounds of the invention often have ionizable groups so as to be capable of preparation as salts. In that case, wherever reference is made to the compound, it is understood in the art that a pharmaceutically acceptable salt may also be used. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art. In some cases, the compounds may contain both an acidic and a basic functional group, in which case they may have two ionized groups and yet have no net charge.

In another aspect, the invention provides a pharmaceutical composition comprising any of the above-described compounds, admixed with a pharmaceutically acceptable excipient.

In another aspect, the invention provides a method to treat cancer, a vascular disorder, inflammation, or a pathogenic infection, comprising administering to a subject in need of such treatment, an effective amount of any of the above-described compounds.

The compounds of the invention are useful as medicaments, and are useful for the manufacture of medicaments, including medicaments to treat conditions disclosed herein, such as cancers, inflammatory conditions, infections, pain, and immunological disorders.

The terms "treat" and "treating" as used herein refer to ameliorating, alleviating, lessening, and removing symptoms of a disease or condition. A candidate molecule or compound described herein may be in a therapeutically effective amount in a formulation or medicament, which is an amount that can lead to a biological effect, such as apoptosis of certain cells (e.g., cancer cells), reduction of proliferation of certain cells, or lead to ameliorating, alleviating, lessening, or removing symptoms of a disease or condition, for example. The terms also can refer to reducing or stopping a cell proliferation rate (e.g., slowing or halting tumor growth) or reducing the number of proliferating cancer cells (e.g., removing part or all of a tumor).

These terms also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganisms include but are not limited to virus, bacterium and fungus.

The compounds of Formula I are active as inhibitors of CK2, and are thus useful to treat infections by certain pathogens, including protozoans and viruses. The invention thus provides methods for treating protozoal disorders such as protozoan parasitosis, including infection by parasitic protozoa responsible for neurological disorders such as schizophrenia, paranoia, and encephalitis in immunocompromised patients, as well as Chagas' disease. It also provides methods to treat various viral diseases, including human immunodeficiency virus type 1 (HIV-1), human papilloma viruses (HPVs), herpes simplex virus (HSV), Epstein-Barr virus (EBV), human cytomegalovirus, hepatitis C and B viruses, influenza virus, Borna disease virus, adenovirus, coxsackievirus, coronavirus and varicella zoster virus. The methods for treating these disorders comprise administering to a subject in need thereof an effective amount of a compound of Formula (I).

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

The invention in part provides pharmaceutical compositions comprising at least one compound within the scope of the invention as described herein, and methods of using compounds described herein.

In addition, the invention in part provides methods for identifying a candidate molecule that interacts with a CK2 and/or Pim, which comprises contacting a composition containing a CK2 or Pim protein and a molecule described herein with a candidate molecule and determining whether the amount of the molecule described herein that interacts with the protein is modulated, whereby a candidate molecule that modulates the amount of the molecule described herein that interacts with the protein is identified as a candidate molecule that interacts with the protein.

Also provided by the invention are methods for modulating certain protein kinase activities. Protein kinases catalyze the transfer of a gamma phosphate from adenosine triphosphate to a serine or threonine amino acid (serine/threonine protein kinase), tyrosine amino acid (tyrosine protein kinase), tyrosine, serine or threonine (dual specificity protein kinase) or histidine amino acid (histidine protein kinase) in a peptide or protein substrate. Thus, included herein are methods which comprise contacting a system comprising a protein kinase protein with a compound described herein in an amount effective for modulating (e.g., inhibiting) the activity of the protein kinase. In some embodiments, the activity of the protein kinase is the catalytic activity of the protein (e.g., catalyzing the transfer of a gamma phosphate from adenosine triphosphate to a peptide or protein substrate). In certain embodiments, provided are methods for identifying a candidate molecule that interacts with a protein kinase, which comprise: contacting a composition containing a protein kinase and a compound described herein with a candidate molecule under conditions in which the compound and the protein kinase interact, and determining whether the amount of the compound that interacts with the protein kinase is modulated relative to a control interaction between the compound and the protein kinase without the candidate molecule, whereby a candidate molecule that modulates the amount of the compound interacting with the protein kinase relative to the control interaction is identified as a candidate molecule that interacts with the protein kinase. Systems in such embodiments can be a cell-free system or a system comprising cells (e.g., in vitro). The protein kinase, the compound or the molecule in some embodiments is in association with a solid phase. In certain embodiments, the interaction between the compound and the protein kinase is detected via a detectable label, where in some embodiments the protein kinase comprises a detectable label and in certain embodiments the compound comprises a detectable label. The interaction between the compound and the protein kinase sometimes is detected without a detectable label.

Provided also are compositions of matter comprising a protein kinase and a compound described herein. In some embodiments, the protein kinase in the composition is a serine-threonine protein kinase. In some embodiments, the protein kinase in the composition is, or contains a subunit (e.g., catalytic subunit, SH2 domain, SH3 domain) of, CK2 or a Pim subfamily protein kinase (e.g., PIM1, PIM2, PIM3). In certain embodiments the composition is cell free and sometimes the protein kinase is a recombinant protein.

The protein kinase can be from any source, such as cells from a mammal, ape or human, for example. Examples of serine-threonine protein kinases that can be inhibited, or may potentially be inhibited, by compounds disclosed herein include without limitation human versions of CK2, CK2α2, and Pim subfamily kinases (e.g., PIM1, PIM2, PIM3). A serine-threonine protein kinase sometimes is a member of a sub-family containing one or more of the following amino acids at positions corresponding to those listed in human CK2: leucine at position 45, methionine at position 163 and isoleucine at position 174. Examples of such protein kinases include without limitation human versions of CK2, STK10, HIPK2, HIPK3, DAPK3, DYK2 and PIM-1. Nucleotide and amino acid sequences for protein kinases and reagents are publicly available (e.g., World Wide Web URLs ncbi.nlm.nih.gov/sites/entrez/ and Invitrogen.com). For example, various nucleotide sequences can be accessed using the following accession numbers: NM_002648.2 and NP_002639.1 for PIM1; NM_006875.2 and NP_006866.2 for PIM2; XM_938171.2 and XP_943264.2 for PIM3.

The invention also in part provides methods for treating a condition related to aberrant cell proliferation. For example, provided are methods of treating a cell proliferative condition in a subject, which comprises administering a compound described herein to a subject in need thereof in an amount effective to treat the cell proliferative condition. The subject may be a research animal (e.g., rodent, dog, cat, monkey), optionally containing a tumor such as a xenograft tumor (e.g., human tumor), for example, or may be a human. A cell proliferative condition sometimes is a tumor or non-tumor cancer, including but not limited to, cancers of the colorectum, breast, lung, liver, pancreas, lymph node, colon, prostate, brain, head and neck, skin, liver, kidney, blood and heart (e.g., leukemia, lymphoma, carcinoma).

Compounds and compositions of the invention may be used alone or in combination with anticancer or other agents, such as a palliative agents, that are typically administered to a patient being treated for cancer, as further described herein.

Also provided are methods for treating a condition related to inflammation or pain. For example, methods are provided for treating pain in a subject, which comprise administering a compound described herein to a subject in need thereof in an amount effective to treat the pain. Provided also are methods of treating inflammation in a subject, which comprise administering a compound described herein to a subject in need thereof in an amount effective to treat the inflammation. The subject may be a research animal (e.g., rodent, dog, cat, monkey), for example, or may be a human. Conditions associated with inflammation and pain include without limitation acid reflux, heartburn, acne, allergies and allergen sensitivities, Alzheimer's disease, asthma, atherosclerosis, bronchitis, carditis, celiac disease, chronic pain, Crohn's disease, cirrhosis, colitis, dementia, dermatitis, diabetes, dry eyes, edema, emphysema, eczema, fibromyalgia, gastroenteritis, gingivitis, heart disease, hepatitis, high blood pressure, insulin resistance, interstitial cystitis, joint pain/arthritis/rheumatoid arthritis, metabolic syndrome (syndrome X), myositis, nephritis, obesity, osteopenia, glomerulonephritis (GN), juvenile cystic kidney disease, and type I nephronophthisis (NPHP), osteoporosis, Parkinson's disease, Guam-Parkinson dementia, supranuclear palsy, Kuf's disease, and Pick's disease, as well as memory impairment, brain ischemia, and schizophrenia, periodontal disease, polyarteritis, polychondritis, psoriasis, scleroderma, sinusitis, Sjögren's syndrome, spastic colon, systemic candidiasis, tendonitis, urinary track infections, vaginitis, inflammatory cancer (e.g., inflammatory breast cancer) and the like.

Methods for determining and monitoring effects of compounds herein on pain or inflammation are known. For example, formalin-stimulated pain behaviors in research animals can be monitored after administration of a compound described herein to assess treatment of pain (e.g., Li et al., *Pain* 115(1-2): 182-90 (2005)). Also, modulation of pro-inflammatory molecules (e.g., IL-8, GRO-alpha, MCP-1, TNFalpha and iNOS) can be monitored after administration of a compound described herein to assess treatment of inflammation (e.g., Parhar et al., *Int J Colorectal Dis.* 22(6): 601-9 (2006)), for example. Thus, also provided are methods for determining whether a compound herein reduces inflammation or pain, which comprise contacting a system with a compound described herein in an amount effective for modulating (e.g., inhibiting) the activity of a pain signal or inflammation signal.

Provided also are methods for identifying a compound that reduces inflammation or pain, which comprise: contacting a system with a compound of Formula I; and detecting a pain signal or inflammation signal, whereby a compound that modulates the pain signal relative to a control molecule is identified as a compound that reduces inflammation of pain. Non-limiting examples of pain signals are formalin-stimulated pain behaviors and examples of inflammation signals include without limitation a level of a pro-inflammatory molecule. The invention thus in part pertains to methods for modulating angiogenesis in a subject, and methods for treating a condition associated with aberrant angiogenesis in a subject. proliferative diabetic retinopathy.

CK2 has also been shown to play a role in the pathogenesis of atherosclerosis, and may prevent atherogenesis by maintaining laminar shear stress flow. CK2 plays a role in vascularization, and has been shown to mediate the hypoxia-induced activation of histone deacetylases (HDACs). CK2 is also involved in diseases relating to skeletal muscle and bone tissue, including, e.g., cardiomyocyte hypertrophy, heart failure, impaired insulin signaling and insulin resistance, hypophosphatemia and inadequate bone matrix mineralization.

Thus in one aspect, the invention provides methods to treat each of these conditions, comprising administering to a subject in need of such treatment an effect amount of a CK2 inhibitor, such as a compound of Formula I as described herein.

The invention also in part pertains to methods for modulating an immune response in a subject, and methods for treating a condition associated with an aberrant immune response in a subject. Thus, provided are methods for determining whether a compound herein modulates an immune response, which comprise contacting a system with a compound described herein in an amount effective for modulating (e.g., inhibiting) an immune response or a signal associated with an immune response. Signals associated with immunomodulatory activity include, e.g., stimulation of T-cell proliferation, suppression or induction of cytokines, including, e.g., interleukins, interferon-γ and TNF. Methods of assessing immunomodulatory activity are known in the art.

Also provided are methods for treating a condition associated with an aberrant immune response in a subject, which comprise administering a compound described herein to a subject in need thereof in an amount effective to treat the condition. Conditions characterized by an aberrant immune response include without limitation, organ transplant rejection, asthma, autoimmune disorders, including rheumatoid arthritis, multiple sclerosis, myasthenia gravis, systemic lupus erythematosus, scleroderma, polymyositis, mixed connective tissue disease (MCTD), Crohn's disease, and ulcerative colitis. In certain embodiments, an immune response may be modulated by administering a compound herein in combination with a molecule that modulates (e.g., inhibits) the biological activity of an mTOR pathway member or member of a related pathway (e.g., mTOR, PI3 kinase, AKT). In certain embodiments the molecule that modulates the biological activity of an mTOR pathway member or member of a related pathway is rapamycin. In certain embodiments, provided herein is a composition comprising a compound described herein in combination with a molecule that modulates the biological activity of an mTOR pathway member or member of a related pathway, such as rapamycin, for example.

In certain embodiments of the present invention, the compound is a compound of Formula Ia, and in certain embodiments it is a compound of Formula Ib.

Formulations and Routes of Administration

Any suitable formulation of a compound described above can be prepared for administration by methods known in the art. Selection of useful excipients or carriers can be achieved without undue experimentation, based on the desired route of administration and the physical properties of the compound to be administered.

Any suitable route of administration may be used, as determined by a treating physician, including, but not limited to, oral, parenteral, intravenous, intramuscular, transdermal, topical and subcutaneous routes. Depending on the subject to be treated, the mode of administration, and the type of treatment desired—e.g., prevention, prophylaxis, therapy; the compounds are formulated in ways consonant with these parameters. Preparation of suitable formulations for each route of administration are known in the art. A summary of such formulation methods and techniques is found in *Remington's Pharmaceutical Sciences*, latest edition, Mack Publishing Co., Easton, Pa. The formulation of each substance or of the combination of two substances will frequently include a diluent as well as, in some cases, adjuvants, buffers, preservatives and the like. The substances to be administered can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised, and can be applied to compounds of the invention. See, for example, U.S. Pat. No. 5,624,677, the methods of which are incorporated herein by reference.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the appropriate dosage of a compound described above often is 0.01-15 mg/kg, and sometimes 0.1-10 mg/kg. In some embodiments, a suitable dosage of the compound of the invention for an adult patient will be between 1 and 500 mg per dose, frequently between 10 and 300 mg, and the dosage may be administered 1-4 times per day. Dosage levels are dependent on the nature of the condition, drug efficacy, the condition of the patient, the judgment of the practitioner, and the frequency and mode of administration; however, optimization of such parameters is within the ordinary level of skill in the art.

Therapeutic Combinations

Compounds of the invention may be used alone or in combination with another therapeutic agent. The invention provides methods to treat conditions such as cancer, inflammation and immune disorders by administering to a subject in need of such treatment a therapeutically effective amount of a therapeutic agent useful for treating said disorder and administering to the same subject a therapeutically effective amount of a modulator of the present invention. A CK2 and/or Pim modulator is an agent that inhibits or enhances a biological activity of a CK2 protein, a Pim protein or both, and is generically referred to hereafter as a "modulator." Compounds of Formula I are exemplary 'modulators.' The therapeutic agent and the modulator may be administered together, either as separate pharmaceutical compositions or admixed in a single pharmaceutical composition. The therapeutic agent and the modulator may also be administered separately, including at different times and with different frequencies. The modulator may be administered by any known route, such as orally, intravenously, intramuscularly, nasally, and the like; and the therapeutic agent may also be administered by any conventional route. In many embodiments, at least one and optionally both of the modulator and the therapeutic agent may be administered orally. Preferably, the modulator is an inhibitor, and it may inhibit either one of CK2 and Pim, or both of them to provide the treatment effects described herein.

In certain embodiments, a "modulator" as described above may be used in combination with a therapeutic agent that can act by binding to regions of DNA that can form certain quadruplex structures. In such embodiments, the therapeutic agents have anticancer activity on their own, but their activity is enhanced when they are used in combination with a modulator. This synergistic effect allows the therapeutic agent to be administered in a lower dosage while achieving equivalent or higher levels of at least one desired effect.

A modulator may be separately active for treating a cancer. For combination therapies described above, when used in combination with a therapeutic agent, the dosage of a modulator will frequently be two-fold to ten-fold lower than the dosage required when the modulator is used alone to treat the same condition or subject. Determination of a suitable amount of the modulator for use in combination with a therapeutic agent is readily determined by methods known in the art.

Compounds and compositions of the invention may be used in combination with anticancer or other agents, such as palliative agents, that are typically administered to a patient being treated for cancer. Such "anticancer agents" include, e.g., classic chemotherapeutic agents, as well as molecular targeted therapeutic agents, biologic therapy agents, and radiotherapeutic agents.

When a compound or composition of the invention is used in combination with an anticancer agent to another agent, the present invention provides, for example, simultaneous, staggered, or alternating treatment. Thus, the compound of the invention may be administered at the same time as an anticancer agent, in the same pharmaceutical composition; the compound of the invention may be administered at the same time as the anticancer agent, in separate pharmaceutical compositions; the compound of the invention may be administered before the anticancer agent, or the anticancer agent may be administered before the compound of the invention, for example, with a time difference of seconds, minutes, hours, days, or weeks.

In examples of a staggered treatment, a course of therapy with the compound of the invention may be administered, followed by a course of therapy with the anticancer agent, or the reverse order of treatment may be used, and more than one series of treatments with each component may also be used. In certain examples of the present invention, one component, for example, the compound of the invention or the anticancer agent, is administered to a mammal while the other component, or its derivative products, remains in the bloodstream of the mammal. For example, a compound for formulae (I)-(IV) may be administered while the anticancer agent or its derivative products remains in the bloodstream, or the anticancer agent may be administered while the compound of formulae (I)-(IV) or its derivatives remains in the bloodstream. In other examples, the second component is administered after all, or most of the first component, or its derivatives, have left the bloodstream of the mammal.

The compound of the invention and the anticancer agent may be administered in the same dosage form, e.g., both administered as intravenous solutions, or they may be administered in different dosage forms, e.g., one compound may be administered topically and the other orally. A person of ordinary skill in the art would be able to discern which combinations of agents would be useful based on the particular characteristics of the drugs and the cancer involved.

Anticancer agents useful in combination with the compounds of the present invention may include agents selected from any of the classes known to those of ordinary skill in the art, including, but not limited to, antimicrotubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; nonreceptor tyrosine kinase angiogenesis inhibitors; immunotherapeutic agents; pro-apoptotic agents; and cell cycle signaling inhibitors; other agents.

Anti-microtubule or anti-mitotic agents are phase specific agents that are typically active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that are believed to operate at the G2/M phases of the cell cycle. It is believed that the diterpenoids stabilize the p-tubulin subunit of the microtubules, by binding with this protein. Disassembly of the protein appears then to be inhibited with mitosis being arrested and cell death following.

Examples of diterpenoids include, but are not limited to, taxanes such as paclitaxel, docetaxel, larotaxel, ortataxel, and tesetaxel. Paclitaxel is a natural diterpene product isolated from the Pacific yew tree *Taxus brevifolia* and is commercially available as an injectable solution TAXOL®. Docetaxel is a semisynthetic derivative of paclitaxel q. v., prepared using a natural precursor, 10-deacetyl-baccatin III, extracted from the needle of the European Yew tree. Docetaxel is commercially available as an injectable solution as TAXOTERE®.

Vinca alkaloids are phase specific anti-neoplastic agents derived from the periwinkle plant. Vinca alkaloids that are believed to act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, vindesine, and vinorelbine. Vinblastine, vincaleukoblastine sulfate, is commercially available as VELBAN® as an injectable solution. Vincristine, vincaleukoblastine 22-oxo-sulfate, is commercially available as ONCOVIN® as an injectable solution. Vinorelbine, is commercially available as an injectable solution of vinorelbine tartrate (NAVELBINE®), and is a semisynthetic vinca alkaloid derivative.

Platinum coordination complexes are non-phase specific anti-cancer agents, which are interactive with DNA. The platinum complexes are believed to enter tumor cells, undergo, aquation and form intra- and interstrand crosslinks with DNA causing adverse biological effects to the tumor. Platinum-based coordination complexes include, but are not limited to cisplatin, carboplatin, nedaplatin, oxaliplatin, satraplatin, and (SP-4-3)-(cis)-amminedichloro-[2-methylpyridine] platinum(II). Cisplatin, cis-diamminedichloroplatinum, is commercially available as PLATINOL® as an injectable solution. Carboplatin, platinum, diammine [1,1-cyclobutane-dicarboxylate(2-)-0,0'], is commercially available as PARAPLATIN® as an injectable solution.

Alkylating agents are generally non-phase specific agents and typically are strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, alkyl sulfonates such as busulfan; ethyleneimine and methylmelamine derivatives such as altretamine and thiotepa; nitrogen mustards such as chlorambucil, cyclophosphamide, estramustine, ifosfamide, mechlorethamine, melphalan, and uramustine; nitrosoureas such as carmustine, lomustine, and streptozocin; triazenes and imidazotetrazines such as dacarbazine, procarbazine, temozolamide, and temozolomide. Cyclophosphamide, 2-[bis(2-chloroethyl)-amino] tetrahydro-2H-1,3,2-oxazaphosphorine 2-oxide monohydrate, is commercially available as an injectable solution or tablets as CYTOXAN®. Melphalan, 4-[bis(2-chloroethyl) amino]-L-phenylalanine, is commercially available as an injectable solution or tablets as ALKERAN®. Chlorambucil, 4-[bis(2-chloroethyl)amino]-benzenebutanoic acid, is commercially available as LEUKERAN® tablets. Busulfan, 1,4-butanediol dimethanesulfonate, is commercially available as MYLERAN® TABLETS. Carmustine, 1,3-[bis(2-chloroethyl)-1-nitrosourea, is commercially available as single vials of lyophilized material as BiCNU®, 5-(3,3-dimethyl-1-triazeno)-imidazole-4-carboxamide, is commercially available as single vials of material as DTIC-Dome®.

Anti-tumor antibiotics are non-phase specific agents which are believed to bind or intercalate with DNA. This may result in stable DNA complexes or strand breakage, which disrupts ordinary function of the nucleic acids, leading to cell death. Examples of anti-tumor antibiotic agents include, but are not limited to, anthracyclines such as daunorubicin (including liposomal daunorubicin), doxorubicin (including liposomal doxorubicin), epirubicin, idarubicin, and valrubicin; *strepto-*

*myces*-related agents such as bleomycin, actinomycin, mithramycin, mitomycin, porfiromycin; and mitoxantrone. Dactinomycin, also know as Actinomycin D, is commercially available in injectable form as COSMEGEN®. Daunorubicin, (8S-cis-)-8-acetyl-10-[(3-amino-2,3,6-trideoxy-α-L-lyxohexopyranosyl)oxy]-7,8,9,10-tetrahydro-6,8,11-trihydroxy-1-methoxy-5,12-naphthacenedione hydrochloride, is commercially available as a liposomal injectable form as DAUNOXOME® or as an injectable as CERUBIDINE®. Doxorubicin, (8S,10S)-10-[(3-amino-2,3,6-trideoxy-α-L-lyxohexopyranosyl)oxy]-8-glycoloyl, 7,8,9,10-tetrahydro-6, 8, 11-trihydroxy-1-methoxy-5,12-naphthacenedione hydrochloride, is commercially available in an injectable form as RUBEX® or ADRIAMYCIN RDF®. Bleomycin, a mixture of cytotoxic glycopeptide antibiotics isolated from a strain of *Streptomyces verticil/us*, is commercially available as BLENOXANE®.

Topoisomerase II inhibitors include, but are not limited to, epipodophyllotoxins, which are phase specific anti-neoplastic agents derived from the mandrake plant. Epipodophyllotoxins typically affect cells in the S and G2 phases of the cell cycle by forming a ternary complex with topoisomerase II and DNA causing DNA strand breaks. The strand breaks accumulate and cell death follows. Examples of epipodophyllotoxins include, but are not limited to, etoposide, teniposide, and amsacrine. Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Teniposide, 4'-demethyl-epipodophyllotoxin 9[4,6-0-(R)-thenylidene-β-D-glucopyranoside], is commercially available as an injectable solution as VUMON® and is commonly known as VM-26.

Antimetabolite neoplastic agents are phase specific antineoplastic agents that typically act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Anti-metabolites, include purine analogs, such as fludarabine, cladribine, chlorodeoxyadenosine, clofarabine, mercaptopurine, pentostatin, erythrohydroxynonyladenine, fludarabine phosphate and thioguanine; pyrimidine analogs such as fluorouracil, gemcitabine, capecitabine, cytarabine, azacitidine, edatrexate, floxuridine, and troxacitabine; antifolates, such as methotrexate, pemetrexed, raltitrexed, and trimetrexate. Cytarabine, 4-amino-1-p-D-arabinofuranosyl-2(1 H)-pyrimidinone, is commercially available as CYTOSAR-U® and is commonly known as Ara-C. Mercaptopurine, 1,7-dihydro-6H-purine-6-thione monohydrate, is commercially available as PURINETHOL®. Thioguanine, 2-amino-1, 7-dihydro-6H-purine-6-thione, is commercially available as TABLOID®. Gemcitabine, 2'-deoxy-2',2'-difluorocytidine monohydrochloride (p-isomer), is commercially available as GEMZAR®.

Topoisomerase I inhibitors including, camptothecin and camptothecin derivatives. Examples of topoisomerase I inhibitors include, but are not limited to camptothecin, topotecan, irinotecan, rubitecan, belotecan and the various optical forms (i.e., (R), (S) or (R,S)) of 7-(4-methylpiperazino-methylene)-10,11-ethylenedioxy-camptothecin, as described in U.S. Pat. Nos. 6,063,923; 5,342,947; 5,559,235; 5,491,237 and pending U.S. patent application Ser. No. 08/977,217 filed Nov. 24, 1997. Irinotecan HCl, (4S)-4,11-diethyl-4-hydroxy-9-[(4-piperidinopiperidino)-carbonyloxy]-1 H-pyrano[3',4', 6,7]indolizino[1,2-b]quinoline-3,14-(4H,12H)-dione hydrochloride, is commercially available as the injectable solution CAMPT0SAR®. Irinotecan is a derivative of camptothecin which binds, along with its active metabolite 8N-38, to the topoisomerase I-DNA complex. Topotecan HCl, (S)-10-[(dimethylamino)methyl]-4-ethyl-4,9-dihydroxy-1H-pyrano [3',4',6,7]indolizinol[1,2-b]quinoline-3,14-(4H,12H)-dione monohydrochloride, is commercially available as the injectable solution HYCAMTIN®.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, androgens such as fluoxymesterone and testolactone; antiandrogens such as bicalutamide, cyproterone, flutamide, and nilutamide; aromatase inhibitors such as aminoglutethimide, anastrozole, exemestane, formestane, vorazole, and letrozole; corticosteroids such as dexamethasone, prednisone and prednisolone; estrogens such as diethylstilbestrol; antiestrogens such as fulvestrant, raloxifene, tamoxifen, toremifine, droloxifene, and iodoxyfene, as well as selective estrogen receptor modulators (SERMS) such those described in U.S. Pat. Nos. 5,681,835, 5,877,219, and 6,207,716; 5α-reductases such as finasteride and dutasteride; gonadotropin-releasing hormone (GnRH) and analogues thereof which stimulate the release of leutinizing hormone (LH) and/or follicle stimulating hormone (FSH), for example LHRH agonists and antagonists such as buserelin, goserelin, leuprolide, and triptorelin; progestins such as medroxyprogesterone acetate and megestrol acetate; and thyroid hormones such as levothyroxine and liothyronine.

Signal transduction pathway inhibitors are those inhibitors, which block or inhibit a chemical process which evokes an intracellular change, such as cell proliferation or differentiation. Signal tranduction inhibitors useful in the present invention include, e.g., inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases. Receptor tyrosine kinases are transmembrane proteins having an extracellular ligand binding domain, a transmembrane domain, and a tyrosine kinase domain. Receptor tyrosine kinases are involved in the regulation of cell growth and are sometimes termed growth factor receptors.

Inappropriate or uncontrolled activation of many of these kinases, for example by over-expression or mutation, has been shown to result in uncontrolled cell growth. Accordingly, the aberrant activity of such kinases has been linked to malignant tissue growth. Consequently, inhibitors of such kinases could provide cancer treatment methods.

Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene.

Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., *Exp*.

Opin. Ther. Patents (2000) 10(6):803-818; Shawver et al., Drug Discov. Today (1997), 2(2):50-63; and Lofts, F. J. et al., "Growth factor receptors as targets", New Molecular Targets for Cancer Chemotherapy, ed. Workman, Paul and Kerr, David, CRC press 1994, London. Specific examples of receptor tyrosine kinase inhibitors include, but are not limited to, sunitinib, erlotinib, gefitinib, and imatinib.

Tyrosine kinases which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., J. Hematotherapy & Stem Cell Res. (1999) 8(5): 465-80; and Bolen, J. B., Brugge, J. S., Annual Review of Immunology. (1997) 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E., J. Pharmacol. Toxicol. Methods. (1995), 34(3): 125-32. Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., J. Biochemistry. (1999) 126 (5): 799-803; Brodt, P, Samani, A, & Navab, R, Biochem. Pharmacol. (2000) 60:1101-1107; Massague, J., Weis-Garcia, F., Cancer Surv. (1996) 27:41-64; Philip, P. A, and Harris, A L, Cancer Treat. Res. (1995) 78: 3-27; Lackey, K. et al. Bioorg. Med. Chem. Letters, (2000) 10(3): 223-226; U.S. Pat. No. 6,268,391; and Martinez-Lacaci, I., et al., Int. J. Cancer (2000), 88(1): 44-52 Inhibitors of Phosphotidyl inositol-3 Kinase family members including blockers of PI3-kinase, ATM, DNA-PK, and Ku are also useful in the present invention. Such kinases are discussed in Abraham, R T. Current Opin. Immunol. (1996), 8(3): 412-8; Canman, C. E., Lim, D. S., Oncogene (1998) 17(25): 3301-8; Jackson, S. P., Int. J. Biochem. Cell Biol. (1997) 29(7):935-8; and Zhong, H. et al., Cancer Res. (2000) 60(6):1541-5. Also useful in the present invention are Myo-inositol signaling inhibitors such as phospholipase C blockers and Myoinositol analogues. Such signal inhibitors are described in Powis, G., and Kozikowski A, (1994) New Molecular Targets for Cancer Chemotherapy, ed., Paul Workman and David Kerr, CRC Press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R, Gervasoni, S I, Matar, P., J. Biomed. Sci. (2000) 7(4): 292-8; Ashby, M. N., Curr. Opin. Lipidol. (1998) 9(2): 99-102; and Oliff, A., Biochim. Biophys. Acta, (1999) 1423 (3):C19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al., Cancer Treat. Rev., (2000) 26(4): 269-286); Herceptin® erbB2 antibody (see Stern, D F, Breast Cancer Res. (2000) 2(3):176-183); and 2CB VEGFR2 specific antibody (see Brekken, R. A. et al., Cancer Res. (2000) 60(18): 5117-24).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alphav beta3) that will inhibit angiogenesis; endostatin and angiostatin (non-RTK) may also prove useful in combination with the disclosed erb family inhibitors. (See Bruns, C J et al., Cancer Res. (2000), 60(11): 2926-2935; Schreiber A B, Winkler M E, & Derynck R., Science (1986) 232(4755):1250-53; Yen L. et al., Oncogene (2000) 19(31): 3460-9).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T, et al., Cancer Res. (2000) 60(13): 3569-76; and Chen Y, et al., Cancer Res. (1998) 58(9):1965-71.

Agents used in pro-apoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family. Therefore, strategies designed to downregulate the expression of bcl-2 in tumors have demonstrated clinical benefit and are now in Phase II/III trials, namely Genta's G3139 bcl-2 antisense oligonucleotide. Such pro-apoptotic strategies using the antisense oligonucleotide strategy for bcl-2 are discussed in Waters J S, et al., J. Clin. Oncol. (2000) 18(9): 1812-23; and Kitada S, et al. Antisense Res. Dev. (1994) 4(2): 71-9.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania G R & Chang Y-T., *Exp. Opin. Ther. Patents* (2000) 10(2):215-30.

Other molecular targeted agents include FKBP binding agents, such as the immunosuppressive macrolide antibiotic, rapamycin; gene therapy agents, antisense therapy agents, and gene expression modulators such as the retinoids and rexinoids, e.g. adapalene, bexarotene, trans-retinoic acid, 9-cisretinoic acid, and N-(4 hydroxyphenyl)retinamide; phenotype-directed therapy agents, including: monoclonal antibodies such as alemtuzumab, bevacizumab, cetuximab, ibritumomab tiuxetan, rituximab, and trastuzumab; immunotoxins such as gemtuzumab ozogamicin, radioimmunoconjugates such as 131-tositumomab; and cancer vaccines.

Miscellaneous agents include altretamine, arsenic trioxide, gallium nitrate, hydroxyurea, levamisole, mitotane, octreotide, procarbazine, suramin, thalidomide, photodynamic compounds such as methoxsalen and sodium porfimer, and proteasome inhibitors such as bortezomib.

Biologic therapy agents include: interferons such as interferon-u2a and interferon-u2b, and interleukins such as aldesleukin, denileukin diftitox, and oprelvekin.

In addition to these anticancer agents intended to act against cancer cells, combination therapies including the use of protective or adjunctive agents, including: cytoprotective agents such as armifostine, dexrazonxane, and mesna, phosphonates such as pamidronate and zoledronic acid, and stimulating factors such as epoetin, darbepoetin, filgrastim, PEG-filgrastim, and sargramostim, are also envisioned.

Compounds of the invention can be made using known starting materials and methods, in view of the following reaction schemes and examples. Where it is helpful to refer to specific positions on compounds such as those in Example 1, the following numbering convention will be used:

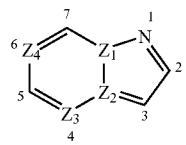

Certain 7-substituted pyrazolo[1,5-a]pyrimidine ring systems can be made by the following synthetic methods, in combination with the reactions in the examples below that enable a person of ordinary skill to introduce the appropriate 3-position groups on the bicyclic ring system.

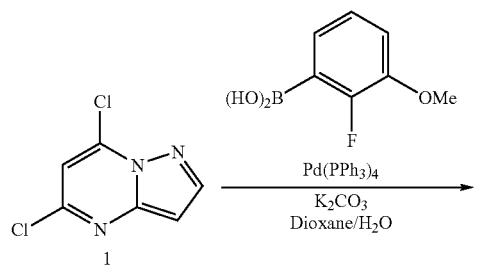

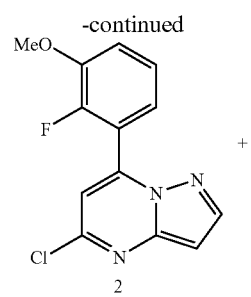

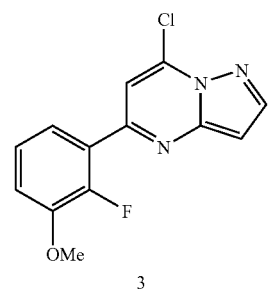

The above reaction is known (WO2005/63755) and can be carried out, for example, by adding 2-fluoro-3-methoxyphenyl boronic acid and 5,7-dichloropyrazolo[1,5-a]pyrimidine 1 to a mixture of 1,4-dioxane/water along with potassium carbonate and tetrakis(triphenylphosphine) palladium (0) followed by heating. Compounds 2 and 3 may be isolated from the residue and separated by column chromatography.

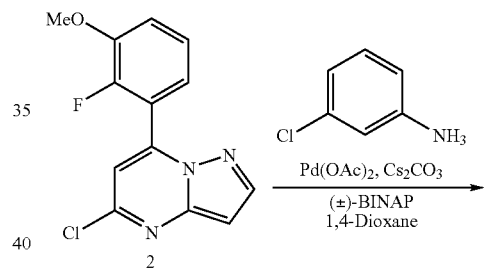

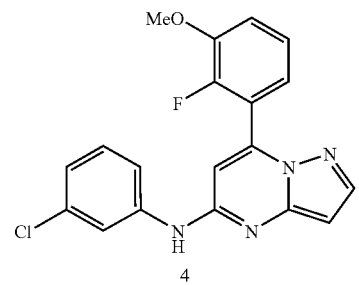

Compound 4 could be synthesized by heating 5-chloro-7-(2-fluoro-3-methoxyphenyl)pyrazolo[1,5-a]pyrimidine 2 in 1,4 dioxane with cesium carbonate, Pd (OAc)$_2$, (±)-BINAP and 3-chloroaniline. The residue may be purified by column chromatography to provide compound 4.

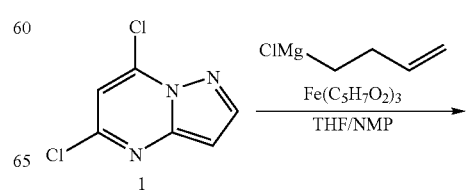

-continued

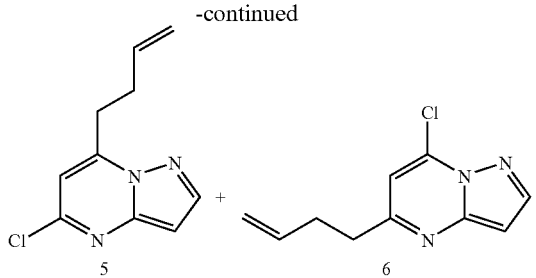

The above reaction is known (WO2005/63755 and WO2008/134035) and can be carried out, for example, by adding 3-butenylmagnesium chloride to a solution of 5,7-dichloropyrazolo[1,5-a]pyrimidine 1 and iron (III) acetylacetonate in THF/NMP. The residue may be purified by column chromatography to provide compounds 5 and 6.

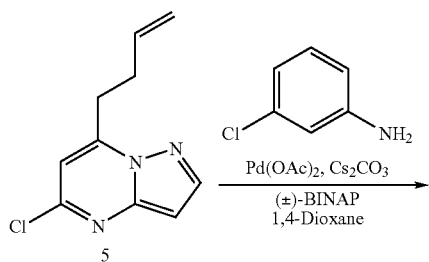

Compound 7 could be synthesized by heating 7-(but-3-enyl)-5-chloropyrazolo[1,5-a]pyrimidine 5 in 1,4 dioxane with cesium carbonate, Pd (OAc)$_2$, (±)-BINAP and 3-chloroaniline. The residue may be purified by column chromatography to provide compound 7. Other anilines can be used similarly to provide various substitution patterns on the phenyl ring.

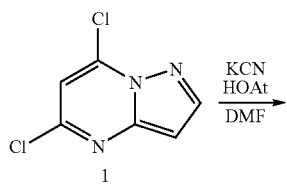

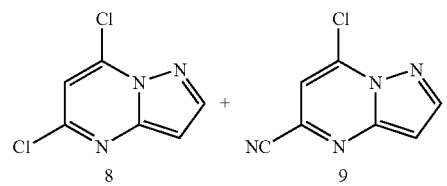

The above reaction is known (WO2008/63671) and can be carried out, for example, by adding HOAt and KCN to solution of 5,7-dichloropyrazolo[1,5-a]pyrimidine 1 in DMF followed by heating. The residue may be purified by column chromatography to provide compounds 8 and 9.

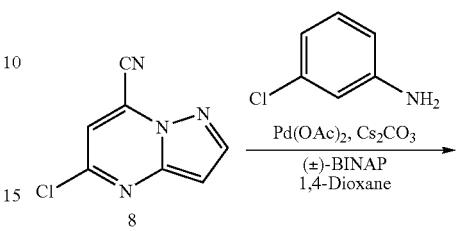

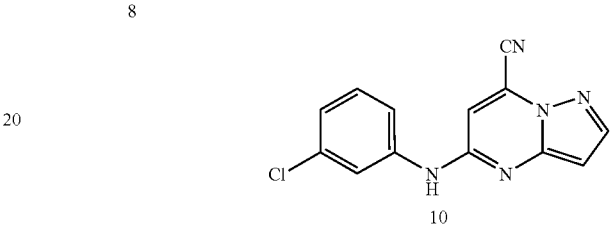

Compound 10 could be synthesized by heating 5-chloropyrazolo[1,5-a]pyrimidine-7-carbonitrile 8 in 1,4 dioxane with cesium carbonate, Pd (OAc)$_2$, (±)-BINAP and 3-chloroaniline. The residue may be purified by column chromatography to provide compound 10. Again, a variety of anilines can be used in this reaction to vary the substitution pattern on the phenyl ring.

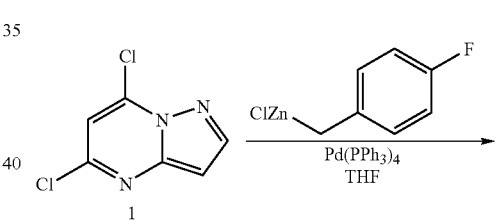

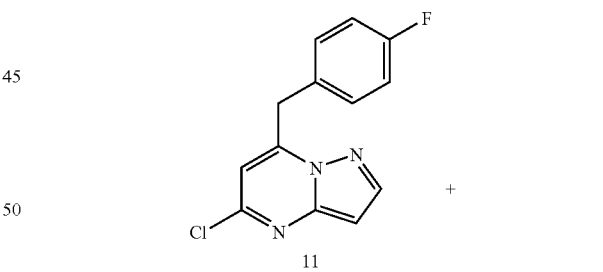

The above reaction is known (WO2008/63671) and can be carried out, for example, by adding 5,7-dichloropyrazolo[1,5-a]pyrimidine 1 and tetrakis(triphenylphosphine) palladium (0) to a solution of (4-fluorobenzyl) zinc chloride in THF and heating. The residue may be purified by column chromatography to provide compounds 11 and 12.

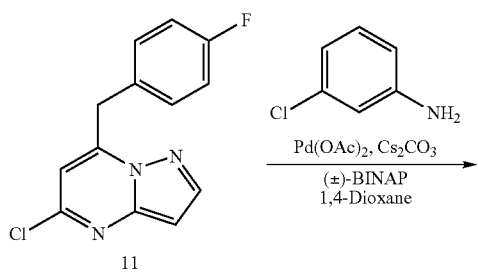

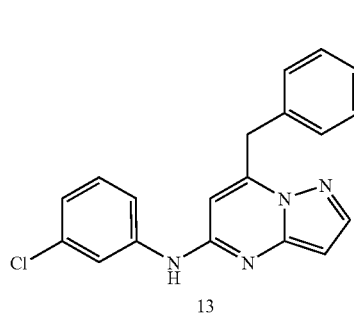

Compound 13 could be synthesized by heating 5-chloro-7-(4-fluorobenzyl)pyrazolo[1,5-a]pyrimidine 11 in 1,4 dioxane with cesium carbonate, Pd (OAc)₂, (±)-BINAP and 3-chloroaniline. The residue may be purified by column chromatography to provide compound 13.

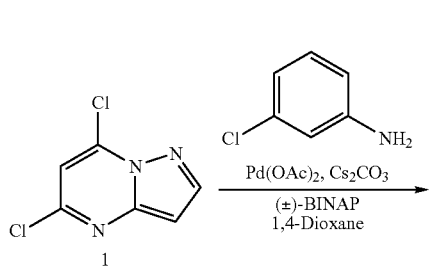

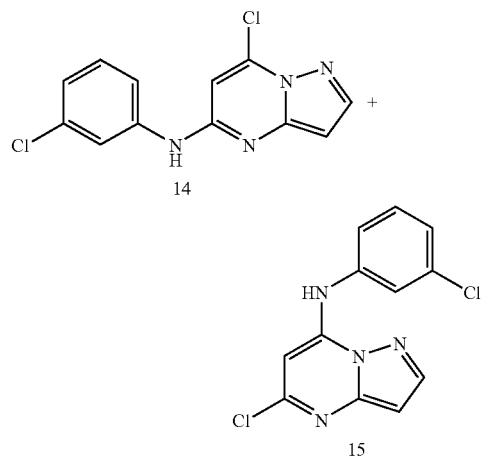

The above reaction is known (U.S. Pat. No. 6,194,410) and can be carried out, for example, by heating 5,7-dichloropyrazolo[1,5-a]pyrimidine 1 in 1,4 dioxane with cesium carbonate, Pd (OAc)₂, (±)-BINAP and 3-chloroaniline. The residue may be purified by column chromatography to provide compounds 14 and 15.

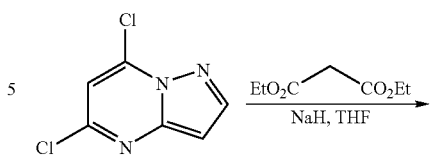

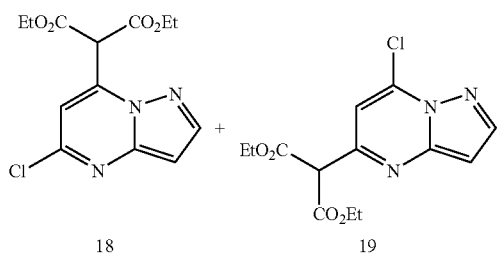

The above reaction is known (EP1354884) and can be carried out, for example, by adding diethyl malonate to a suspension of sodium hydride in THF followed by addition of 5,7-dichloropyrazolo[1,5-a]pyrimidine 1 and heating. The residue may be purified by column chromatography on silica to provide compounds 18 and 19.

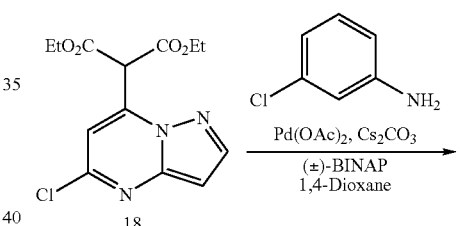

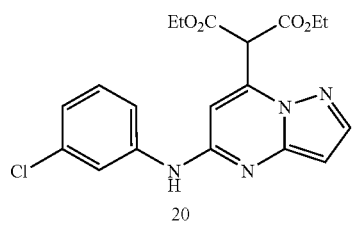

Compound 20 could be synthesized by heating diethyl 2-(5-chloropyrazolo[1,5-a]pyrimidin-7-yl)malonate 18 in 1,4 dioxane with cesium carbonate, Pd (OAc)₂, (±)-BINAP and 3-chloroaniline. The residue may be purified by column chromatography to provide compound 20.

General Preparation of Final Compounds

Compounds from the foregoing schemes are intermediates, useful for synthesis of the compounds of Formula I and Ia/Ib as described herein. Methods for adding the additional heterocyclic group to such compounds are known in the art; representative methods of general applicability are depicted here, and are also exemplified in the following Examples.

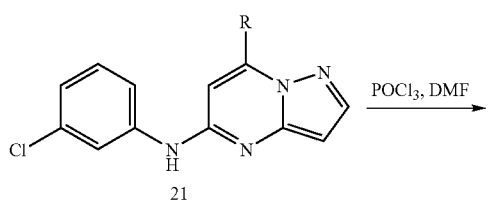

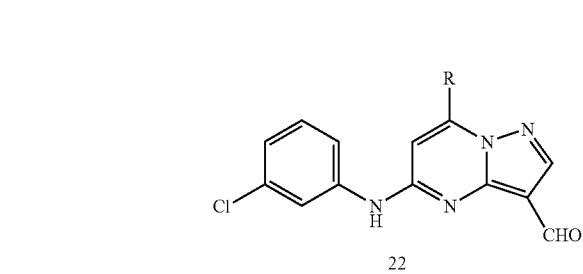

Compounds of structure 22 may be prepared using the Vilsmeier-Haack reaction by reacting pyrazolo[1,5-a]pyrimidines 21 with phosphorous oxychloride in DMF. After aqueous work up, the residue may be purified by column chromatography to provide aldehydes 22.

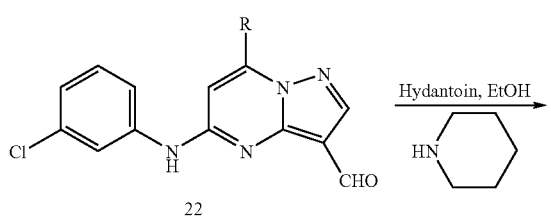

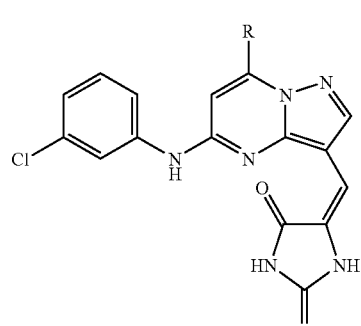

The resulting aldehydes (22) could be reacted with hydantoin in ethanol with a base, such as, piperidine to give the desired pyrazolo[1,5-a]pyrimidin-3-ylmethylene)imidazolidine-2,4-dione of structure 23. Additionally, the corresponding thiazolidine-2,4-dione and the Rhodanine derivatives of compounds 23 could be synthesized using the aforementioned methods.

The following examples illustrate and do not limit the invention. Where a mass spectral peak is identified, it corresponds to an experimental result matching the expected compound or a protonated form thereof, and is provided as proof that the desired compound was obtained.

EXAMPLE 1

Synthesis of 5-((5-(3-chlorophenylamino)pyrazolo[1,5-a]pyrimidin-3-yl)methylene)imidazolidine-2,4-dione

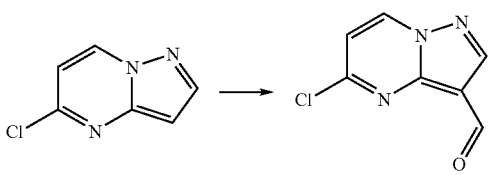 [SMILES: Clc1ccn2nccc2n1 ; O=Cc1cnn2ccc(Cl)nc12]

To 5-chloropyrazolo[1,5-a]pyrimidine (200 mg, 1.31 mmol) in 1.5 ml DMF was added POCl$_3$ (358 μL, 3.92 mmol). The reaction was stirred at room temperature overnight. The mixture was cooled to 0° C. in ice bath and the then neutralized with 6M NaOH. The solid formed was isolated by filtration and air dried to give 165 mg of 5-chloropyrazolo[1,5-a]pyrimidine-3-carbaldehyde as yellow solid (70% yield). LCMS (M+1=182)

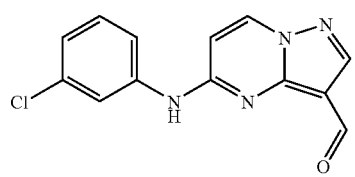

To 5-chloropyrazolo[1,5-a]pyrimidine-3-carbaldehyde (120 mg, 0.66 mmol) in 1.5 ml dioxane was added 3-chloroaniline (35 μL, 3.31 mmol). The mixture was heated in Microwave 10 minutes at 120° C. The solid formed was isolated by filtration and air dried to give 5-(3-chlorophenylamino)pyrazolo[1,5-a]pyrimidine-3-carbaldehyde as orange solid. LCMS (M+1=273)

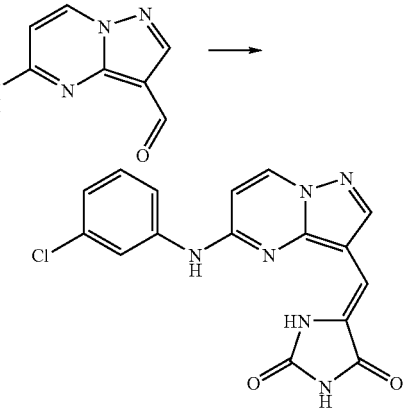

To 5-(3-chlorophenylamino)pyrazolo[1,5-a]pyrimidine-3-carbaldehyde (50 mg, 0.184 mmol) in 1 ml EtOH was added hydantoin (54 mg, 0.552 mmol) and piperidine (54 µL, 0.552 mmol). The mixture was heated in Microwave (200 W) for 60 minutes at 80° C. The solid formed was isolated by filtration and air dried to give 5-((5-(3-chlorophenylamino)pyrazolo[1,5-a]pyrimidin-3-yl)methylene)imidazolidine-2,4-dione. LCMS (M+1=355)

EXAMPLE 2

Synthesis of 5-((5-(3-chlorophenylamino)pyrazolo[1,5-a]pyrimidin-3-yl)methylene)thiazolidine-2,4-dione

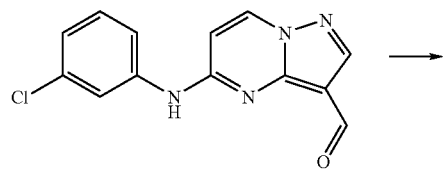

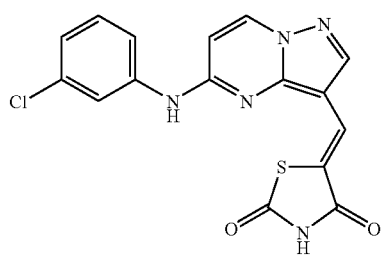

To 5-(3-chlorophenylamino)pyrazolo[1,5-a]pyrimidine-3-carbaldehyde (50 mg, 0.184 mmol) in 1 ml EtOH was added 2,4-thiazolidinedione (22 mg, 0.184 mmol) and piperidine (54 µL, 0.184 mmol). The mixture was heated in Microwave (200 W) for 60 minutes at 80° C. The solid formed was isolated by filtration and air dried to give 5-((5-(3-chlorophenylamino)pyrazolo[1,5-a]pyrimidin-3-yl)methylene)thiazolidine-2,4-dione. LCMS (M+1=372)

EXAMPLE 3

Synthesis of 5-((5-(3-chlorophenylamino)pyrazolo[1,5-a]pyrimidin-3-yl)methylene)-2-thioxothiazolidin-4-one

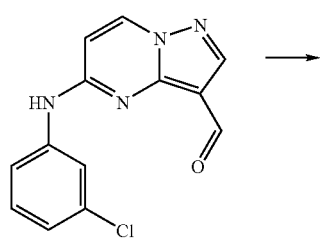

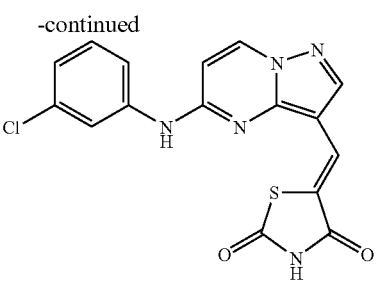

To 5-(3-chlorophenylamino)pyrazolo[1,5-a]pyrimidine-3-carbaldehyde (50 mg, 0.184 mmol) in 1 mL EtOH was added rhodanine (24 mg, 0.184 mmol) and piperidine (18 µL, 0.184 mmol). The mixture was heated in microwave (200 W) for 10 minutes at 80° C. The solid formed was isolated by filtration and air dried to give 5-((5-(3-chlorophenylamino)pyrazolo[1,5-a]pyrimidin-3-yl)methylene)-2-thioxothiazolidin-4-one. LCMS (M+1=388)

EXAMPLE 4

Synthesis of 5-((5-(3-chlorophenylamino)pyrazolo[1,5-a]pyrimidin-3-yl)methylene)-1-methylimidazolidine-2,4-dione

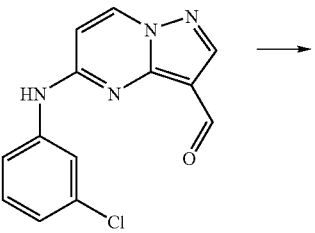

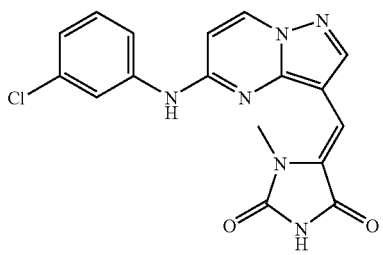

To 5-(3-chlorophenylamino)pyrazolo[1,5-a]pyrimidine-3-carbaldehyde (20 mg, 0.074 mmol) in 0.5 mL EtOH was added 1-methylimidazolidine-2,4-dione (8.4 mg, 0.074 mmol) and piperidine (7.5 µL, 0.074 mmol). The mixture was heated at 70° C. overnight. The solid formed was isolated by filtration and air dried to give 5-((5-(3-chlorophenylamino)pyrazolo[1,5-a]pyrimidin-3-yl)methylene)-1-methylimidazolidine-2,4-dione. LCMS (M+1=369)

EXAMPLE 5

Synthesis of methyl 3-(3-((4-oxo-2-thioxothiazolidin-5-ylidene)methyl)pyrazolo[1,5-a]pyrimidin-5-yl)benzoate

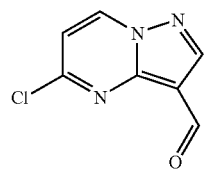

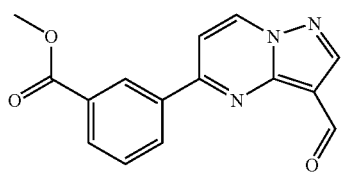

To 5-chloropyrazolo[1,5-a]pyrimidine-3-carbaldehyde (115 mg, 0.64 mmol) in dioxane/water (2850 μL/150 μL) was added 3-(methoxycarbonyl)phenylboronic acid (171 mg, 0.95 mmol), and cesium carbonate (623 mg, 1.91 mmol). The mixture was degassed under nitrogen for 10 minutes and then PdCl$_2$dppf (23 mg, 0.03 mmol) was added. The mixture was heated at 105° C. overnight. Water was added and the resulting solid was isolated by filtration. The solid was then dissolved in dichloromethane and washed with water, dried over Na$_2$SO$_4$ and passed through a plug of silica. The resulting solution was concentrated under vacuum to yield 125 mg of 3-(3-formylpyrazolo[1,5-a]pyrimidin-5-yl)benzoate as a yellow solid (70% yield). LCMS (M+1=282)

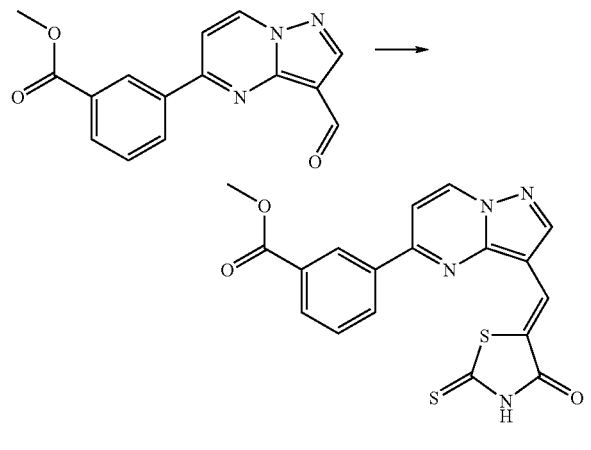

To 3-(3-formylpyrazolo[1,5-a]pyrimidin-5-yl)benzoate (40 mg, 0.14 mmol) in 0.5 mL EtOH was added rhodanine (19 mg, 0.14 mmol) and piperidine (14 μL, 0.14 mmol). The mixture was stirred at room temperature overnight for three nights. The solid formed was isolated by filtration and purified by preparative TLC (1% MeOH/DCM) to yield methyl 3-(3-((4-oxo-2-thioxothiazolidin-5-ylidene)methyl)pyrazolo[1,5-a]pyrimidin-5-yl)benzoate. LCMS (M+1=397)

EXAMPLE 6

Synthesis of methyl 3-(3-((2,4-dioxothiazolidin-5-ylidene)methyl)pyrazolo[1,5-a]pyrimidin-5-yl)benzoate

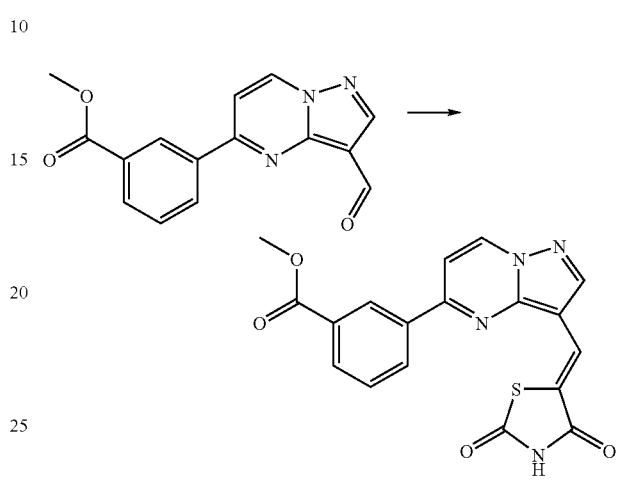

To 3-(3-formylpyrazolo[1,5-a]pyrimidin-5-yl)benzoate (27 mg, 0.096 mmol) in 0.5 mL EtOH was added 2,4-thiazolidinedione (11 mg, 0.096 mmol) and piperidine (9.5 μL, 0.096 mmol). The mixture was stirred at 50° C. overnight. The solid formed was isolated by filtration and air dried to yield 27 mg methyl 3-(3-((2,4-dioxothiazolidin-5-ylidene)methyl)pyrazolo[1,5-a]pyrimidin-5-yl)benzoate as an orange solid (74% yield). LCMS (M+1=381)

EXAMPLE 7

Synthesis of 3-(3-((2,4-dioxothiazolidin-5-ylidene)methyl)pyrazolo[1,5-a]pyrimidin-5-yl)benzoic acid

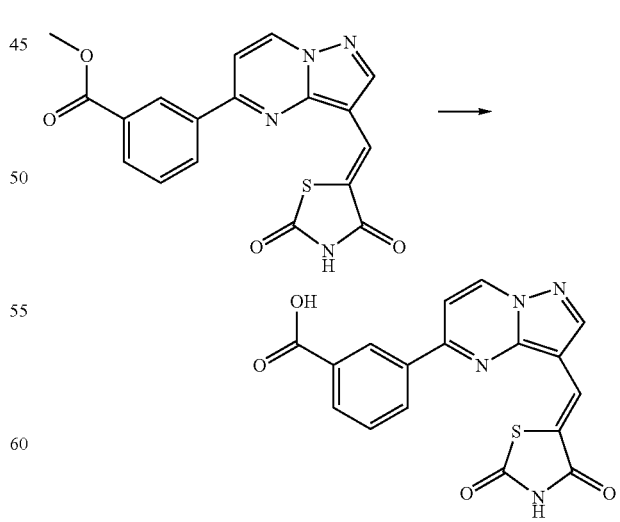

To methyl 3-(3-((2,4-dioxothiazolidin-5-ylidene)methyl)pyrazolo[1,5-a]pyrimidin-5-yl)benzoate (25 mg, 0.066 mmol) in EtOH was added 1 mL of 6M NaOH. The mixture was stirred at room temperature overnight. Solvent was removed under reduced pressure. Water was added and the mixture was neutralized with 1M HCl. The resulting solid was isolated by filtration and air dried to yield 3-(3-((2,4-dioxothiazolidin-5-ylidene)methyl)pyrazolo[1,5-a]pyrimidin-5-yl)benzoic acid. LCMS (M+1=367)

EXAMPLE 8

Synthesis of 5-((5-(3-(2-methyl-1H-imidazol-1-yl)phenylamino)pyrazolo[1,5-a]pyrimidin-3-yl)methylene)thiazolidine-2,4-dione

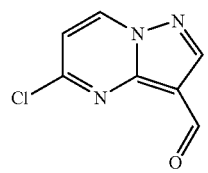

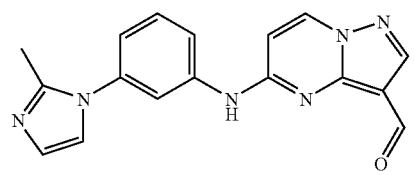

To 5-chloropyrazolo[1,5-a]pyrimidine-3-carbaldehyde (39 mg, 0.215 mmol) in dioxane was added 3-(2-methyl-1H-imidazol-1-yl)aniline (90 mg, 0.520 mmol). The mixture was heated in microwave (200 W) for 50 minutes at 120° C. The solid formed was isolated by filtration and air dried to yield 48 mg 5-(3-(2-methyl-1H-imidazol-1-yl)phenylamino)pyrazolo[1,5-a]pyrimidine-3-carbaldehyde (70% yield). LCMS (M+1=319)

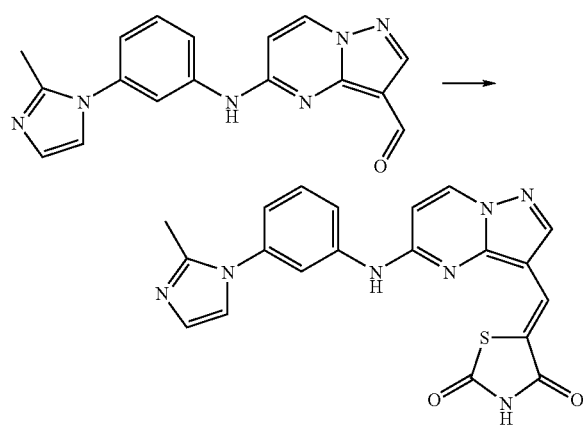

To 5-(3-(2-methyl-1H-imidazol-1-yl)phenylamino)pyrazolo[1,5-a]pyrimidine-3-carbaldehyde (48 mg, 0.151 mmol) in 0.5 mL EtOH was added 2,4-thiazolidinedione (18 mg, 0.151 mmol) and piperidine (15 μL, 0.151 mmol). The mixture was heated at 70° C. overnight. The solid formed was isolated by filtration and dissolved in DMF. Insolubilities were filtered off and the resulting filtrate purified by HPLC to yield 5-((5-(3-(2-methyl-1H-imidazol-1-yl)phenylamino)pyrazolo[1,5-a]pyrimidin-3-yl)methylene)thiazolidine-2,4-dione. LCMS (M+1=418)

EXAMPLE 9

Synthesis of 5-(5-((3-tert-butylphenylamino)pyrazolo[1,5-a]pyrimidin-3-yl)methylene)imidazolidine-2,4-dione

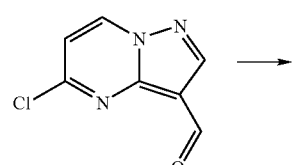

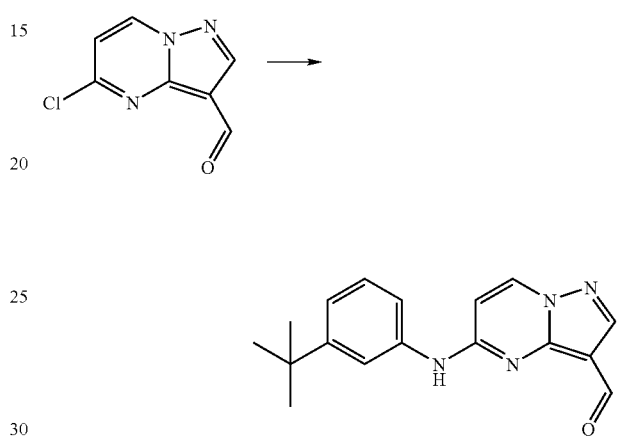

To 5-chloropyrazolo[1,5-a]pyrimidine-3-carbaldehyde (50 mg, 0.276 mmol) in dioxane was added 3-tert-butylaniline (206 mg, 1.381 mmol). The mixture was heated in microwave for 10 minutes at 120° C. The solid formed was isolated by filtration and air dried to yield 78 mg 5-(3-tert-butylphenylamino)pyrazolo[1,5-a]pyrimidine-3-carbaldehyde (96% yield). LCMS (M+1=295)

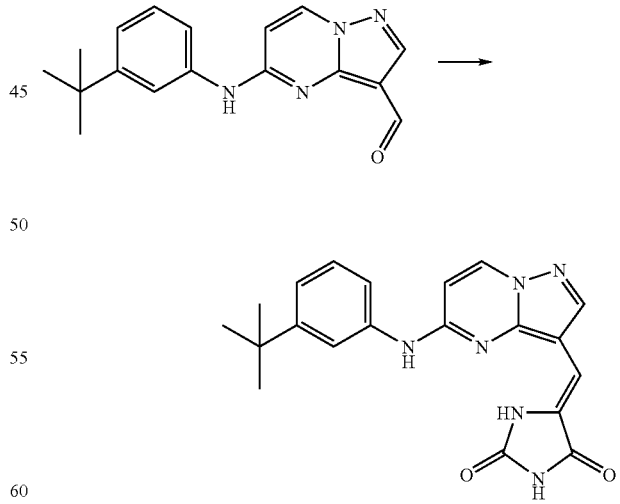

To 5-(3-tert-butylphenylamino)pyrazolo[1,5-a]pyrimidine-3-carbaldehyde (39 mg, 0.133 mmol) in EtOH was added hydantoin (28 mg, 0.280 mmol) and piperidine (13 μL, 0.133 mmol). The mixture was heated at 70° C. overnight. The solid formed was isolated by filtration and air dried to yield 5-((5-(3-tert-butylphenylamino)pyrazolo[1,5-a]pyrimidin-3-yl)methylene)imidazolidine-2,4-dione. LCMS (M+1=377)

EXAMPLE 10

Synthesis of 5-((5-(3-tert-butylphenylamino)pyrazolo[1,5-a]pyrimidin-3-yl)methylene)thiazolidine-2,4-dione

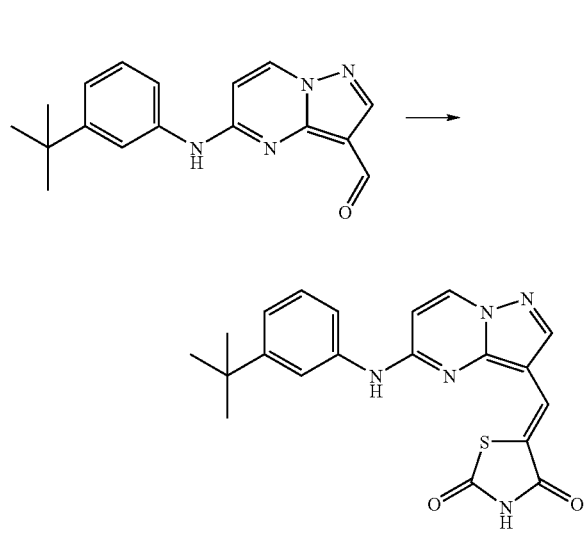 [SMILES: CC(C)(C)c1cccc(Nc2ccn3ncc(C=O)c3n2)c1 ; CC(C)(C)c1cccc(Nc2ccn3ncc(/C=C4\SC(=O)NC4=O)c3n2)c1]

To 5-(3-tert-butylphenylamino)pyrazolo[1,5-a]pyrimidine-3-carbaldehyde (39 mg, 0.133 mmol) in EtOH was added 2,4-thiazolidinedione (16 mg, 0.133 mmol) and piperidine (13 µL, 0.133 mmol). The mixture was heated at 70° C. The solid formed was isolated by filtration and air dried to yield 5-((5-(3-tert-butylphenylamino)pyrazolo[1,5-a]pyrimidin-3-yl)methylene)imidazolidine-2,4-dione. LCMS (M+1=394)

EXAMPLE 11

Synthesis of 5-((5-aminopyrazolo[1,5-a]pyrimidin-3-yl)methylene)imidazolidine-2,4-dione

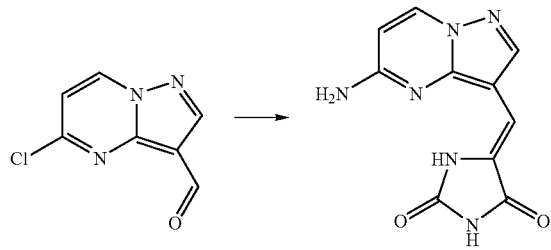 [SMILES: O=Cc1cnn2ccc(Cl)nc12 ; Nc1ccn2ncc(/C=C3\NC(=O)NC3=O)c2n1]

To 5-chloropyrazolo[1,5-a]pyrimidine-3-carbaldehyde (50 mg, 0.276 mmol) in EtOH was added hydantoin (38 mg, 0.380 mmol), DIEA (5 µL, 0.028 mmol), and ammonium acetate (88 mg, 1.143 mmol). The mixture was heated at 70° C. overnight. The solid formed was isolated by filtration and purified by HPLC to yield 5-((5-aminopyrazolo[1,5-a]pyrimidin-3-yl)methylene)imidazolidine-2,4-dione. LCMS (M+1=245)

EXAMPLE 12

Synthesis of 5-((5-aminopyrazolo[1,5-a]pyrimidin-3-yl)methylene)imidazolidine-2,4-dione

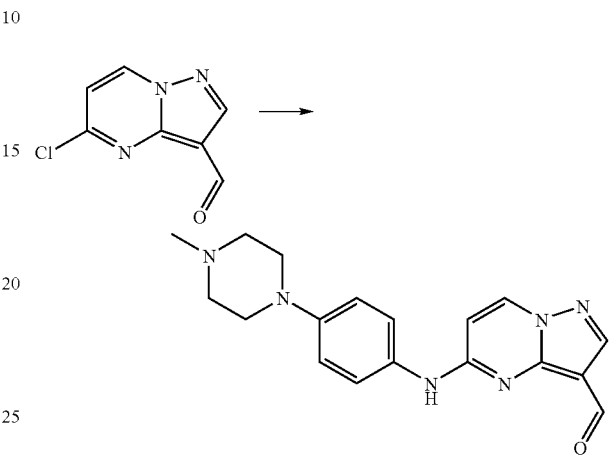

To 5-chloropyrazolo[1,5-a]pyrimidine-3-carbaldehyde (50 mg, 0.276 mmol) in dioxane was added 4-(4-methylpiperazin-1-yl)aniline (264 mg, 1.381 mmol). The mixture was heated in microwave for 20 minutes at 120° C. The solid formed was isolated by filtration to yield 5-(4-(4-methylpiperazin-1-yl)phenylamino)pyrazolo[1,5-a]pyrimidine-3-carbaldehyde. The residue was used in the next step without further purification. LCMS (M+1=337).

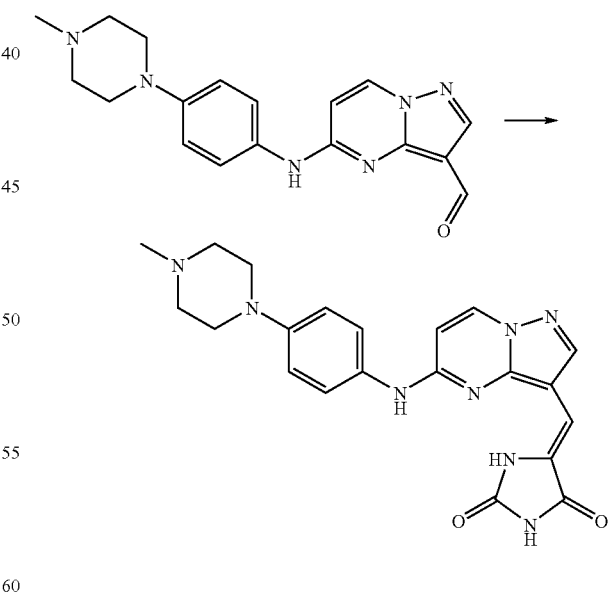

To 5-(4-(4-methylpiperazin-1-yl)phenylamino)pyrazolo[1,5-a]pyrimidine-3-carbaldehyde (56 mg, 0.167 mmol) in EtOH was added hydantoin (17 mg, 0.167 mmol) and piperidine (17 µL, 0.167 mmol). The mixture was heated at 70° C. Solvent was removed under reduced pressure and then the solid was redissolved in MeOH and sonicated. Insolubilities were filtered off and the filtrate was purified by HPLC to yield 5-((5-(4-(4-methylpiperazin-1-yl)phenylamino)pyrazolo[1,5-a]pyrimidin-3-yl)methylene)imidazolidine-2,4-dione. LCMS (M+1=419)

EXAMPLE 13

Synthesis of 5-((5-(3-((1H-imidazol-1-yl)methyl)phenylamino)pyrazolo[1,5-a]pyrimidin-3-yl)methylene)imidazolidine-2,4-dione

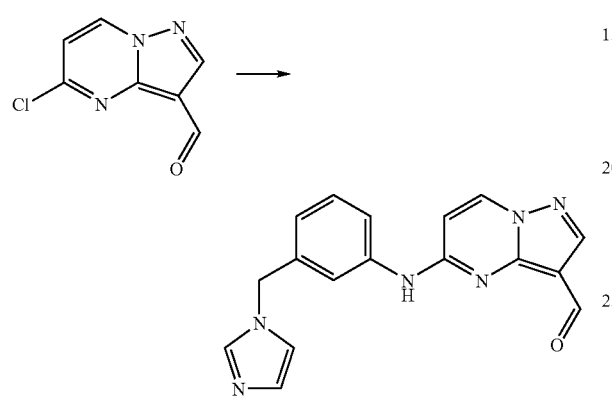

To 5-chloropyrazolo[1,5-a]pyrimidine-3-carbaldehyde (40 mg, 0.221 mmol) in dioxane was added 3-((1H-imidazol-1-yl)methyl)aniline (115 mg, 0.663 mmol). The mixture was heated in microwave for 120 minutes at 120° C. EtOAc was added to the mixture, and washed with water. The organic layer was then dried over $Na_2SO_4$ and solvent was removed under reduced pressure to yield 5-(3-((1H-imidazol-1-yl)methyl)phenylamino)pyrazolo[1,5-a]pyrimidine-3-carbaldehyde. The resulting solid was used in the next step without further purification. LCMS (M+1=319)

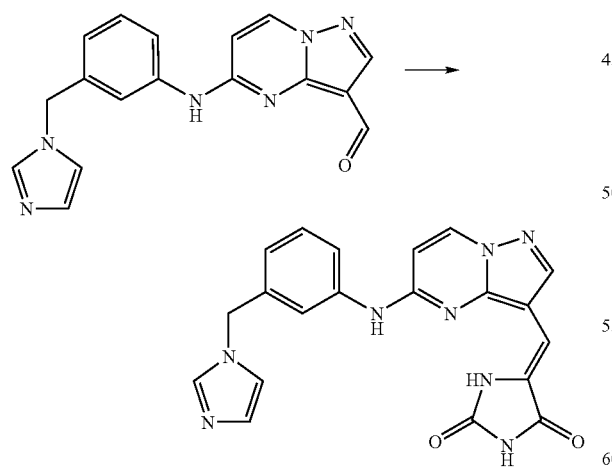

To 5-(3-((1H-imidazol-1-yl)methyl)phenylamino)pyrazolo[1,5-a]pyrimidine-3-carbaldehyde (74 mg, 0.233 mmol) in EtOH was added hydantoin (23 mg, 0.233 mmol) and piperidine (23 μL, 0.233 mmol). The mixture was heated at 70° C. for 48 hr and then purified by HPLC to yield 5-((5-(3-((1H-imidazol-1-yl)methyl)phenylamino)pyrazolo[1,5-a]pyrimidin-3-yl)methylene)imidazolidine-2,4-dione. LCMS (M+1=401)

EXAMPLE 14

Synthesis of 5-((5-(piperidin-1-yl)pyrazolo[1,5-a]pyrimidin-3-yl)methylene)imidazolidine-2,4-dione

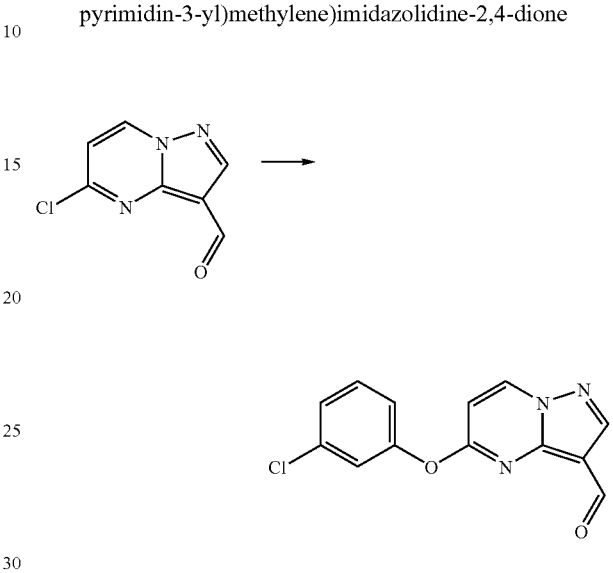

To 5-chloropyrazolo[1,5-a]pyrimidine-3-carbaldehyde (50 mg, 0.276 mmol) in DMF was added 3-chlorophenol (42 mg, 0.331 mmol) and $K_2CO_3$ (190 mg, 1.380 mmol). The mixture was heated at 70° C. for several hours. Water was added and the solid formed was isolated by filtration and air dried to yield 70 mg 5-(3-chlorophenoxy)pyrazolo[1,5-a]pyrimidine-3-carbaldehyde as an orange solid (93% yield). LCMS (M+1=274)

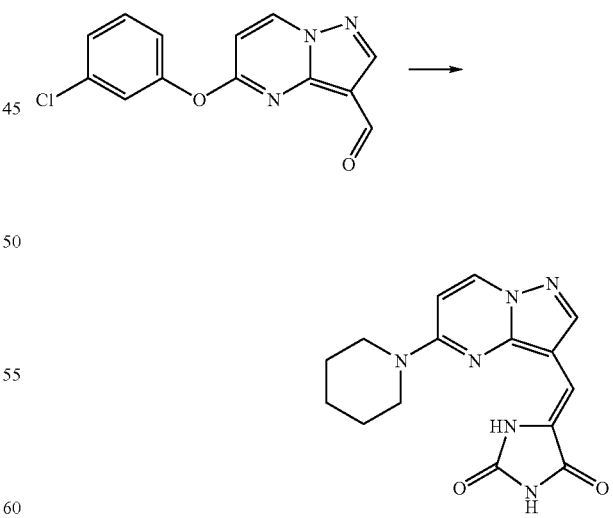

To 5-(3-chlorophenoxy)pyrazolo[1,5-a]pyrimidine-3-carbaldehyde (30 mg, 0.109 mmol) in DMF was added hydantoin (10.9 mg, 0.109 mmol) and piperidine (21.8 μL, 0.218 mmol). The mixture was heated at 70° C. Added water, and the solid formed was isolated by filtration to yield 5-((5-

(piperidin-1-yl)pyrazolo[1,5-a]pyrimidin-3-yl)methylene)imidazolidine-2,4-dione. LCMS (M+1=313)

(3-((diethylamino)methyl)phenylamino)pyrazolo[1,5-a]pyrimidin-3-yl)methylene)imidazolidine-2,4-dione. LCMS (M+1=406)

EXAMPLE 15

Synthesis of 5-((5-(3-((diethylamino)methyl)phenylamino)pyrazolo[1,5-a]pyrimidin-3-yl)methylene)imidazolidine-2,4-dione

EXAMPLE 16

Synthesis of 5-((5-(4-methyl-1,4-diazepan-1-yl)pyrazolo[1,5-a]pyrimidin-3-yl)methylene)imidazolidine-2,4-dione

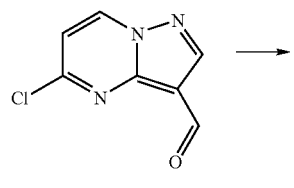

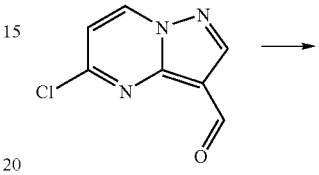

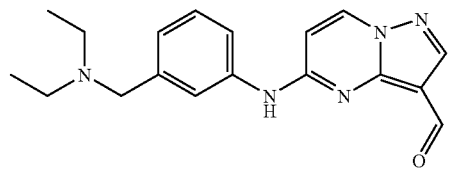

To 5-chloropyrazolo[1,5-a]pyrimidine-3-carbaldehyde (50 mg, 0.276 mmol) in dioxane was added 3-((diethylamino)methyl)aniline (148 mg, 0.829 mmol). The mixture was heated in microwave for 140 minutes at 120° C. Dichloromethane was added, and washed with water. The organic layer was dried over $Na_2SO_4$ and concentrated under reduced pressure. The resulting solution was prepared by TLC (10% MeOH/DCM) to yield 10 mg 5-(3-((diethylamino)methyl)phenylamino)pyrazolo[1,5-a]pyrimidine-3-carbaldehyde (11% yield). LCMS (M+1=324)

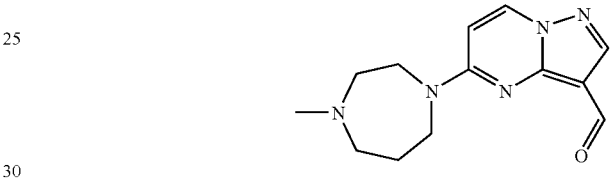

To 5-chloropyrazolo[1,5-a]pyrimidine-3-carbaldehyde (50 mg, 0.276 mmol) in NMP was added 1-methylhomopiperazine (103 μL, 0.829 mmol). The mixture was heated in microwave for 10 minutes at 140° C. Dichloromethane and water were added, and the product extracted in dichloromethane. The organic layer was then washed with water and dried over $Na_2SO_4$ and concentrated under reduced pressure to yield 5-(4-methyl-1,4-diazepan-1-yl)pyrazolo[1,5-a]pyrimidine-3-carbaldehyde. LCMS (M+1=260)

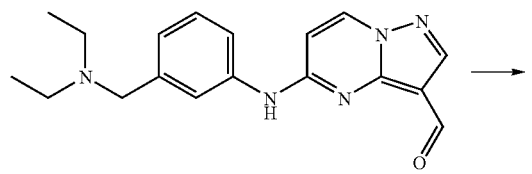

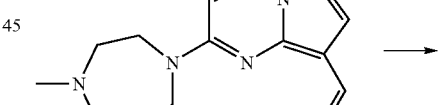

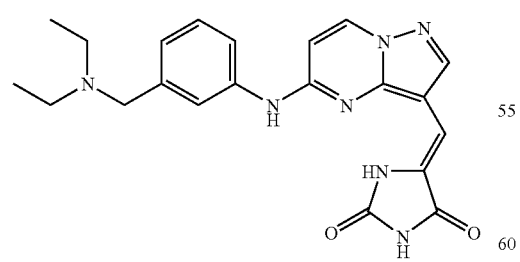

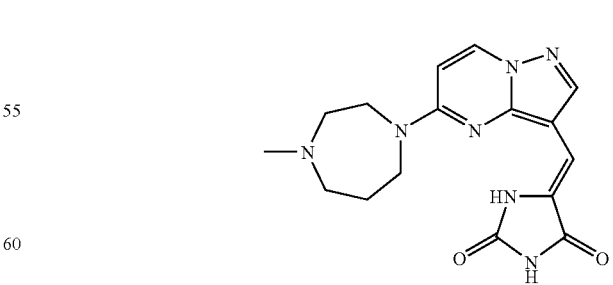

To 5-(3-((diethylamino)methyl)phenylamino)pyrazolo[1,5-a]pyrimidine-3-carbaldehyde (10 mg, 0.031 mmol) in EtOH was added hydantoin (3 mg, 0.031 mmol) and piperidine (3 μL, 0.031 mmol). The mixture was heated at 70° C. overnight. The product was purified by HPLC to yield 5-((5-

To 5-(4-methyl-1,4-diazepan-1-yl)pyrazolo[1,5-a]pyrimidine-3-carbaldehyde (36 mg, 0.138 mmol) in EtOH was added hydantoin (14 mg, 0.138 mmol) and piperidine (14 μL, 0.138 mmol). The mixture was heated at 70° C. and purified by HPLC to yield 5-(5-(4-methyl-1,4-diazepan-1-yl)pyrazolo[1,5-a]pyrimidin-3-yl)methylene)imidazolidine-2,4-dione. LCMS (M+1=342)

EXAMPLE 17

Synthesis of 5-((5-(4-methyl-1,4-diazepan-1-yl)pyrazolo[1,5-a]pyrimidin-3-yl)methylene)thiazolidine-2,4-dione

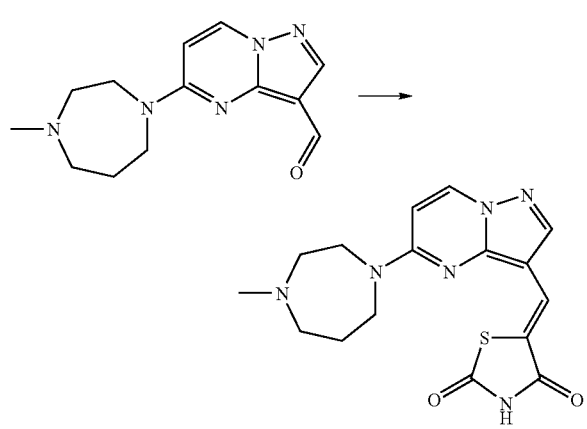

To 5-(4-methyl-1,4-diazepan-1-yl)pyrazolo[1,5-a]pyrimidine-3-carbaldehyde (36 mg, 0.138 mmol) in EtOH was added 2,4-thiazolidinedione (16 mg, 0.138 mmol) and piperidine (14 µL, 0.138 mmol). The mixture was heated at 70° C. and purified by HPLC to yield 5-((5-(4-methyl-1,4-diazepan-1-yl)pyrazolo[1,5-a]pyrimidin-3-yl)methylene)thiazolidine-2,4-dione. LCMS (M+1=359)

EXAMPLE 18

Synthesis of 5-((5-(3-(4-methylpiperazin-1-yl)phenylamino)pyrazolo[1,5-a]pyrimidin-3-yl)methylene)imidazolidine-2,4-dione

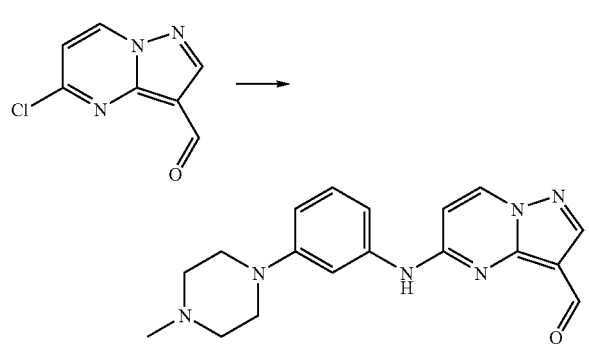

To 5-chloropyrazolo[1,5-a]pyrimidine-3-carbaldehyde (40 mg, 0.221 mmol) in dioxane was added 3-(4-methylpiperazin-1-yl)aniline (127 mg, 0.663 mmol). The mixture was heated in microwave at 120° C. Dichloromethane and water were added, and the product extracted in dichloromethane. The organic layer was then dried over $Na_2SO_4$ and concentrated under reduced pressure to yield 5-(3-(4-methylpiperazin-1-yl)phenylamino)pyrazolo[1,5-a]pyrimidine-3-carbaldehyde. LCMS (M+1=337)

EXAMPLE 19

Synthesis of 5-((5-(3-(4-methylpiperazin-1-yl)phenylamino)pyrazolo[1,5-a]pyrimidin-3-yl)methylene)imidazolidine-2,4-dione

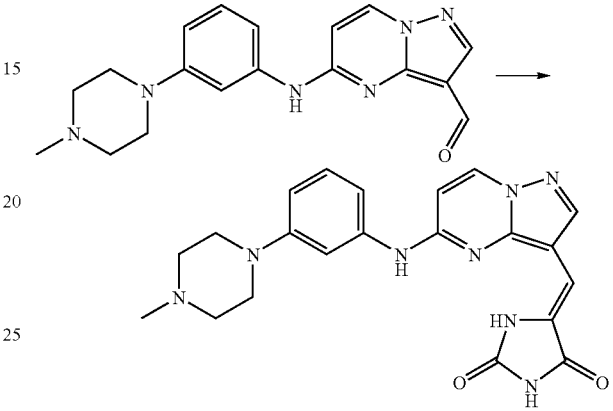

To 5-(3-(4-methylpiperazin-1-yl)phenylamino)pyrazolo[1,5-a]pyrimidine-3-carbaldehyde (74 mg, 0.221 mmol) in EtOH was added hydantoin (22 mg, 0.221 mmol) and piperidine (22 µL, 0.221 mmol). The mixture was heated at 70° C. The solid formed was filtered off and the filtrate was prepared by HPLC to yield 5-((5-(3-(4-methylpiperazin-1-yl)phenylamino)pyrazolo[1,5-a]pyrimidin-3-yl)methylene)imidazolidine-2,4-dione. LCMS (M+1=419)

EXAMPLE 20

Synthesis of 5-((5-(3-(2-morpholinoethoxy)phenylamino)pyrazolo[1,5-a]pyrimidin-3-yl)methylene)imidazolidine-2,4-dione

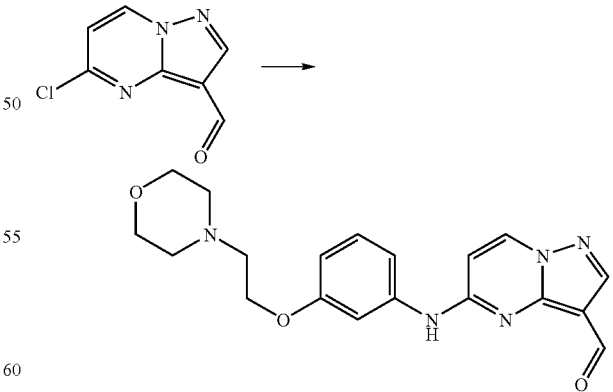

To 5-chloropyrazolo[1,5-a]pyrimidine-3-carbaldehyde (40 mg, 0.221 mmol) in dioxane was added 3-(2-morpholinoethoxy)aniline (147 mg, 0.663 mmol). The mixture was heated in microwave at 120° C. Dichloromethane was added, and washed with water. The organic layer was dried over Na$_2$SO$_4$ and concentrated under reduced pressure to yield 5-(3-(2-morpholinoethoxy)phenylamino)pyrazolo[1,5-a]pyrimidine-3-carbaldehyde. The solid was used in the next step without further purification. LCMS (M+1=368)

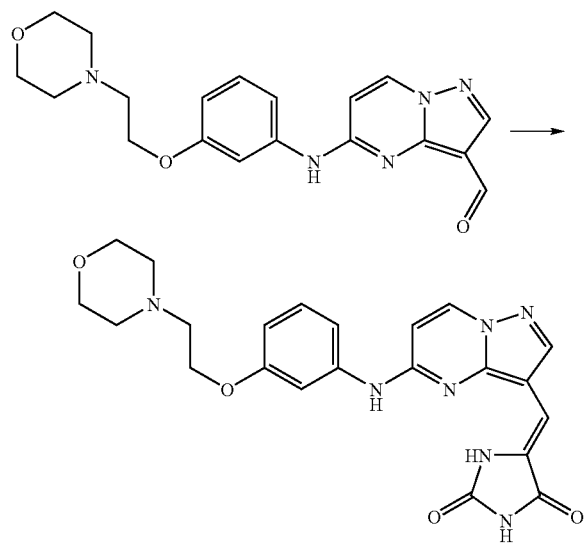

To 5-(3-(2-morpholinoethoxy)phenylamino)pyrazolo[1,5-a]pyrimidine-3-carbaldehyde (81 mg, 0.221 mmol) in EtOH was added hydantoin (27 mg, 0.270 mmol) and piperidine (22 µL, 0.221 mmol). The mixture was heated at 70° C. for 48 hr. The solution was then purified by HPLC to yield 5-((5-(3-(2-morpholinoethoxy)phenylamino)pyrazolo[1,5-a]pyrimidin-3-yl)methylene)imidazolidine-2,4-dione. LCMS (M+1=450)

EXAMPLE 21

Synthesis of 5-((5-(3-isopropoxyphenylamino)pyrazolo[1,5-a]pyrimidin-3-yl)methylene)imidazolidine-2,4-dione

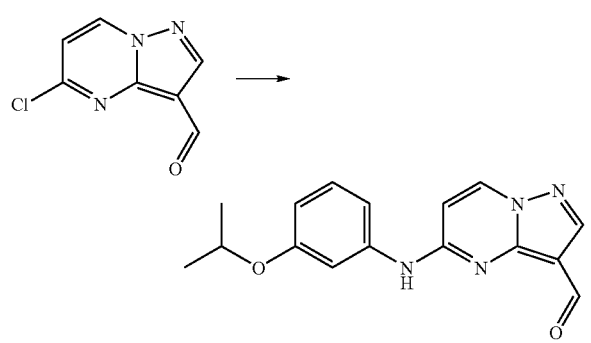

To 5-chloropyrazolo[1,5-a]pyrimidine-3-carbaldehyde (50 mg, 0.276 mmol) in dioxane was added 3-isopropoxyaniline (125 mg, 0.829 mmol). The mixture was heated in microwave for 20 minutes at 120° C. The solid produced was isolated by filtration and then purified by preparative TLC (2% MeOH/DCM) to yield 5-(3-isopropoxyphenylamino)pyrazolo[1,5-a]pyrimidine-3-carbaldehyde. LCMS (M+1=297)

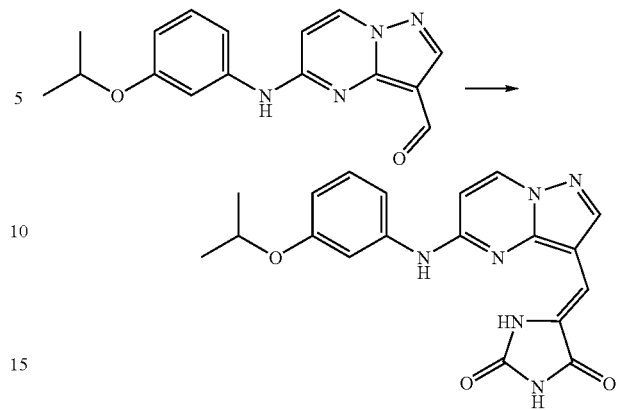

To 5-(3-isopropoxyphenylamino)pyrazolo[1,5-a]pyrimidine-3-carbaldehyde (80 mg, 0.270 mmol) in EtOH was added hydantoin (27 mg, 0.270 mmol) and piperidine (27 µL, 0.270 mmol). The mixture was heated at 70° C. for several hours. The solid produced was isolated by filtration to yield 5-((5-(3-isopropoxyphenylamino)pyrazolo[1,5-a]pyrimidin-3-yl)methylene)imidazolidine-2,4-dione. LCMS (M+1=379)

EXAMPLE 22

Synthesis of 5-((5-(isobutylamino)pyrazolo[1,5-a]pyrimidin-3-yl)methylene)imidazolidine-2,4-dione

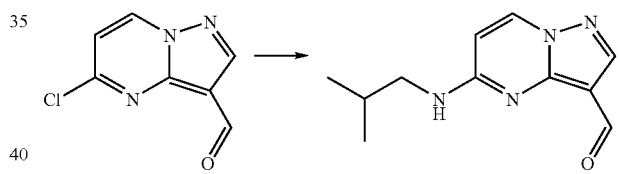

To 5-chloropyrazolo[1,5-a]pyrimidine-3-carbaldehyde (20 mg, 0.110 mmol) in acetonitrile was added 2-methylpropan-1-amine (22 µL, 0.221 mmol). The mixture was heated at 70° C. and produced the desired product, 5-(isobutylamino)pyrazolo[1,5-a]pyrimidine-3-carbaldehyde. LCMS (M+1=219)

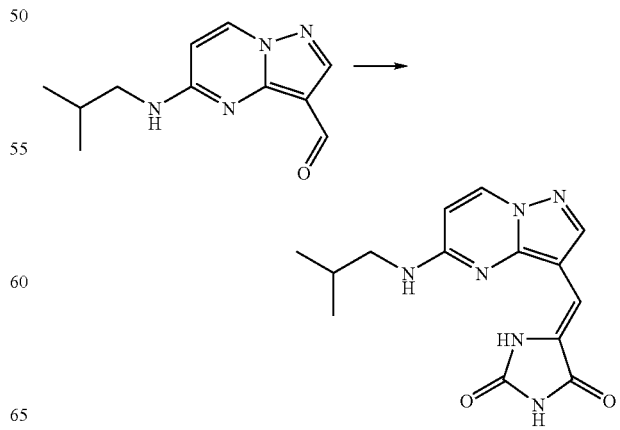

To 5-(isobutylamino)pyrazolo[1,5-a]pyrimidine-3-carbaldehyde (24 mg, 0.110 mmol) in acetonitrile was added hydantoin (11 mg, 0.110 mmol) and piperidine (11 μL, 0.110 mmol). The reaction was heated at 70° C. for 48 hr. The reaction was cooled to room temperature and the solid formed was isolated by filtration to yield 5-((5-(isobutylamino)pyrazolo[1,5-a]pyrimidin-3-yl)methylene)imidazolidine-2,4-dione. LCMS (M+1=301)

EXAMPLE 23

Synthesis of 5-((5-(4-(2-(dimethylamino)ethoxy)phenylamino)pyrazolo[1,5-a]pyrimidin-3-yl)methylene)imidazolidine-2,4-dione

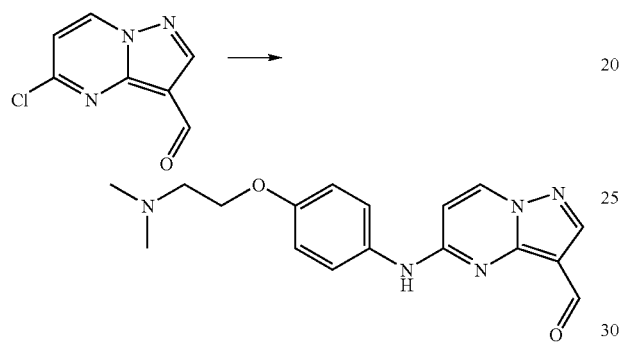

To 5-chloropyrazolo[1,5-a]pyrimidine-3-carbaldehyde (50 mg, 0.276 mmol) in dioxane was added 4-(2-(dimethylamino)ethoxy)aniline (149 mg, 0.829 mmol). The mixture was heated in microwave 100 minutes at 120° C. Water and dichloromethane were added, and the product was extracted into dichloromethane. The organic layer was dried over $Na_2SO_4$ and concentrated under reduced pressured to yield 5-(4-(2-(dimethylamino)ethoxy)phenylamino)pyrazolo[1,5-a]pyrimidine-3-carbaldehyde. LCMS (M+1=408)

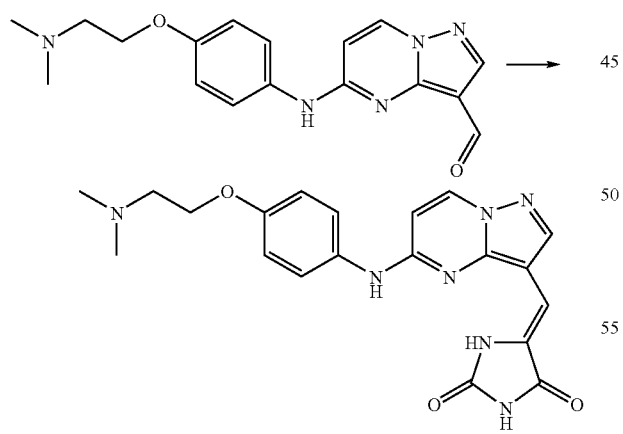

To 5-(4-(2-(dimethylamino)ethoxy)phenylamino)pyrazolo[1,5-a]pyrimidine-3-carbaldehyde (90 mg, 0.276 mmol) in EtOH was added hydantoin (28 mg, 0.276 mmol) and piperidine (28 μL, 0.276 mmol). The mixture was heated at 70° C. overnight three times. Solvent was removed under reduced pressure and MeOH was added. Insolubilities were filtered off, and the filtrate was purified by HPLC to yield 5-((5-(4-(2-(dimethylamino)ethoxy)phenylamino)pyrazolo[1,5-a]pyrimidin-3-yl)methylene)imidazolidine-2,4-dione. LCMS (M+1=408)

EXAMPLE 24

Synthesis of 5-((5-(isopropylamino)pyrazolo[1,5-a]pyrimidin-3-yl)methylene)imidazolidine-2,4-dione

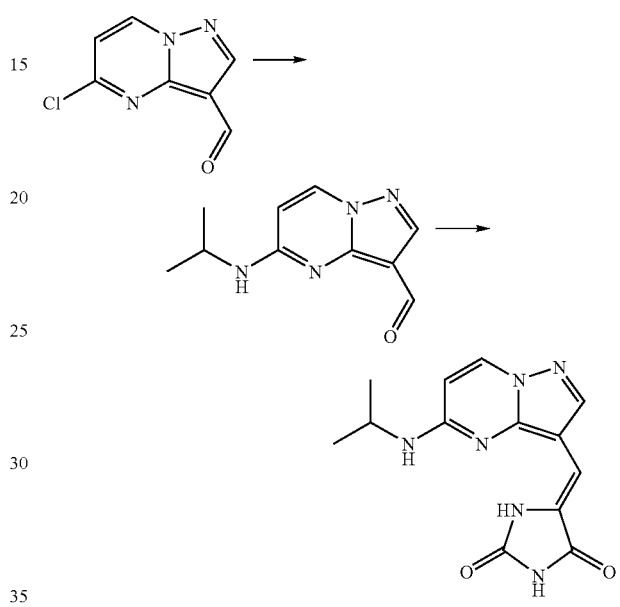

To 5-chloropyrazolo[1,5-a]pyrimidine-3-carbaldehyde (20 mg, 0.11 mmol) in acetonitrile was added isopropylamine (19 μL, 0.22 mmol). The mixture was heated at 70° C. The desired product, 5-(isopropylamino)pyrazolo[1,5-a]pyrimidine-3-carbaldehyde, formed in solution. LCMS (M+1=205)

To this solution was added hydantoin (22 mg, 0.22 mmol) and piperidine (22 μL, 0.22 mmol). The mixture was heated at 70° C. overnight two times. The solution was left to cool to room temperature, then the solid formed was isolated by filtration to yield 5-((5-(isopropylamino)pyrazolo[1,5-a]pyrimidin-3-yl)methylene)imidazolidine-2,4-dione. LCMS (M+1=287)

EXAMPLE 25

Synthesis of 5-((5-(2-fluoroethylamino)pyrazolo[1,5-a]pyrimidin-3-yl)methylene)imidazolidine-2,4-dione

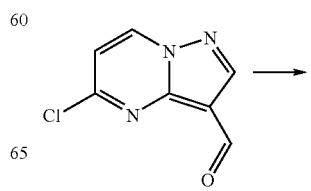

-continued

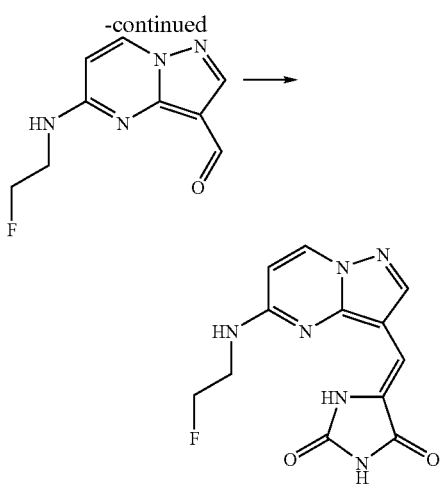

To 5-chloropyrazolo[1,5-a]pyrimidine-3-carbaldehyde (20 mg, 0.11 mmol) in ACN was added 2-fluoroethanamine hydrochloride (22 mg, 0.22 mmol). The mixture was heated at 70° C. The desired product, 5-(2-fluoroethylamino)pyrazolo[1,5-a]pyrimidine-3-carbaldehyde, formed in solution. LCMS (M+1=209)

To this solution was added hydantoin (22 mg, 0.22 mmol) and piperidine (22 µL, 0.22 mmol). The mixture was heated at 70° C. overnight two times. The solution was left to cool to room temperature, then the solid formed was isolated by filtration to yield 5-((5-(2-fluoroethylamino)pyrazolo[1,5-a]pyrimidin-3-yl)methylene)imidazolidine-2,4-dione. LCMS (M+1=291)

EXAMPLE 26

Synthesis of 5-((5-(3-chlorophenylamino)pyrazolo[1,5-a]pyrimidin-3-yl)methylene)imidazolidine-2,4-dione

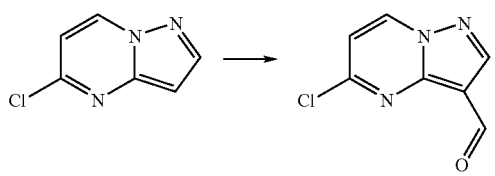 [SMILES: Clc1ccn2nccc2n1 ; O=Cc1cnn2ccc(Cl)nc12]

To 5-chloropyrazolo[1,5-a]pyrimidine (200 mg, 1.31 mmol) in 1.5 mL DMF was added POCl₃ (358 µL, 3.92 mmol). The reaction was stirred at room temperature overnight. The mixture was cooled to 0° C. in ice bath and then neutralized with 6M NaOH. The solid formed was isolated by filtration and air dried to give 165 mg of 5-chloropyrazolo[1,5-a]pyrimidine-3-carbaldehyde as yellow solid (70% yield). LCMS (M+1=182)

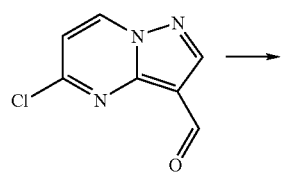

-continued

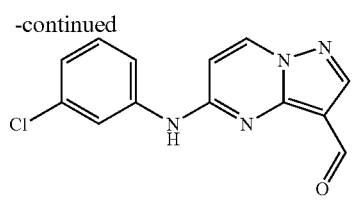

To 5-chloropyrazolo[1,5-a]pyrimidine-3-carbaldehyde (120 mg, 0.66 mmol) in 1.5 mL dioxane was added 3-chloroaniline (351 µL, 3.31 mmol). The mixture was heated in microwave 10 minutes at 120° C. The solid formed was isolated by filtration and air dried to give 5-(3-chlorophenylamino)pyrazolo[1,5-a]pyrimidine-3-carbaldehyde as orange solid. LCMS (M+1=273)

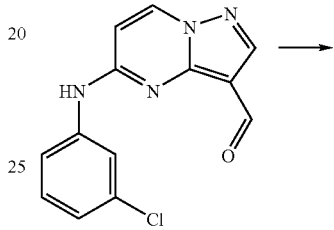

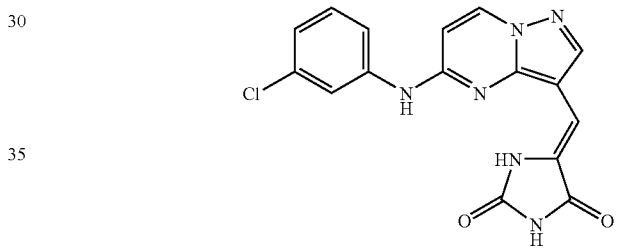

To 5-(3-chlorophenylamino)pyrazolo[1,5-a]pyrimidine-3-carbaldehyde (50 mg, 0.184 mmol) in 1 mL EtOH was added hydantoin (54 mg, 0.552 mmol) and piperidine (54 µL, 0.552 mmol). The mixture was heated in microwave for 60 minutes at 80° C. The solid formed was isolated by filtration and air dried to give 5-((5-(3-chlorophenylamino)pyrazolo[1,5-a]pyrimidin-3-yl)methylene)imidazolidine-2,4-dione. LCMS (M+1=355)

EXAMPLE 27

Synthesis of 5-((5-(3-chlorophenylamino)pyrazolo[1,5-a]pyrimidin-3-yl)methylene)thiazolidine-2,4-dione

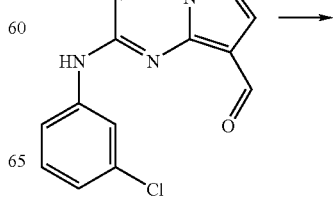

-continued

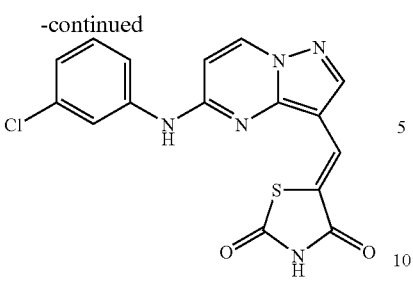

To 5-(3-chlorophenylamino)pyrazolo[1,5-a]pyrimidine-3-carbaldehyde (50 mg, 0.184 mmol) in 1 mL EtOH was added 2,4-thiazolidinedione (22 mg, 0.184 mmol) and piperidine (18 μL, 0.184 mmol). The mixture was heated in microwave for 20 minutes at 80° C. The solid formed was isolated by filtration and air dried to give 5-((5-(3-chlorophenylamino) pyrazolo[1,5-a]pyrimidin-3-yl)methylene)thiazolidine-2,4-dione. LCMS (M+1=372)

EXAMPLE 28

Synthesis of 5-((5-(2-fluorophenyl)pyrazolo[1,5-a]pyrimidin-3-yl)methylene)thiazolidine-2,4-dione

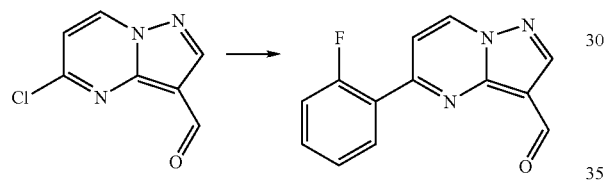

To 5-chloropyrazolo[1,5-a]pyrimidine-3-carbaldehyde (150 mg, 0.83 mmol) in 4 mL DMF/water (0.05%) was added 2-fluorophenylboronic acid (174 mg, 1.245 mmol) and cesium carbonate (812 mg, 2.49 mmol). The mixture was degassed under nitrogen during 10 minutes. PdCl2(dppf)2 (30.3 mg, 0.041 mmol) was then added. The mixture was heated in the microwave at 100° C. for 10 minutes. Water was added, the precipitate was isolated by filtration and air dried to give 5-(2-fluorophenyl)pyrazolo[1,5-a]pyrimidine-3-carbaldehyde. LCMS (M+1)=241

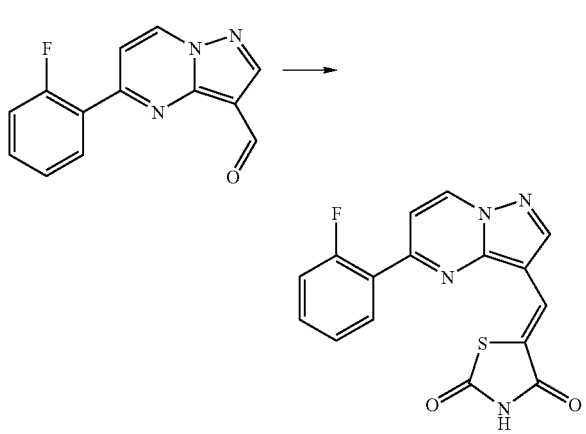

To 5-(2-fluorophenyl)pyrazolo[1,5-a]pyrimidine-3-carbaldehyde (33 mg, 0.137 mmol) in 3 mL ETOH was added thiazolidine-2,4-dione (16 mg, 0.137 mmol) and piperidine (14 μL). The mixture was stirred at R.T. overnight. The solid formed was isolated by filtration and washed with EtOH to give 5-((5-(2-fluorophenyl)pyrazolo[1,5-a]pyrimidin-3-yl) methylene)thiazolidine-2,4-dione.

EXAMPLE 29

Synthesis of (Z)-5-((5-(2-fluorophenyl)pyrazolo[1,5-a]pyrimidin-3-yl)methylene)-2-thioxothiazolidin-4-one

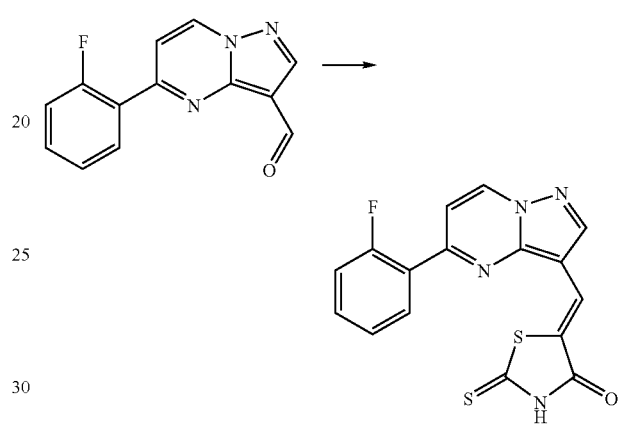

5-((5-(2-Fluorophenyl)pyrazolo[1,5-a]pyrimidin-3-yl) methylene)-2-thioxothiazolidin-4-one was prepared using the same procedure as for the synthesis of 5-((5-(2-fluorophenyl)pyrazolo[1,5-a]pyrimidin-3-yl)methylene)thiazolidine-2,4-dione using Rhodanine instead of thiazolidine-2,4-dione.

EXAMPLE 30

Synthesis of (Z)-5-((5-(2-fluorophenyl)pyrazolo[1,5-a]pyrimidin-3-yl)methylene)imidazolidine-2,4-dione

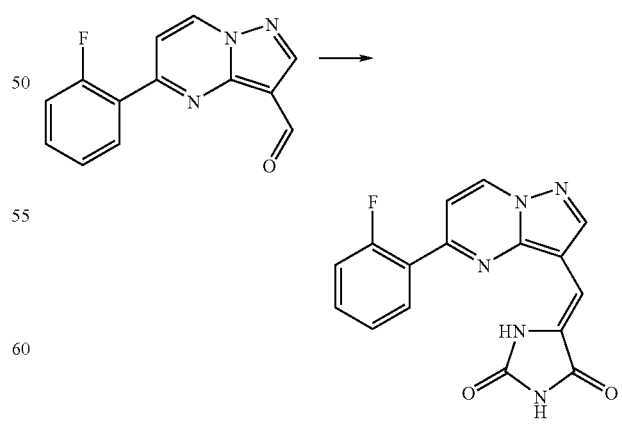

5-((5-(2-fluorophenyl)pyrazolo[1,5-a]pyrimidin-3-yl)methylene)imidazolidine-2,4-dione was prepared using the same procedure as for the synthesis of 5-((5-(2-fluorophenyl)

pyrazolo[1,5-a]pyrimidin-3-yl)methylene)thiazolidine-2,4-dione using hydantoin instead of thiazolidine-2,4-dione.

EXAMPLE 31

Synthesis of 5-((5-(4-chlorophenylamino)pyrazolo[1,5-a]pyrimidin-3-yl)methylene)imidazolidine-2,4-dione

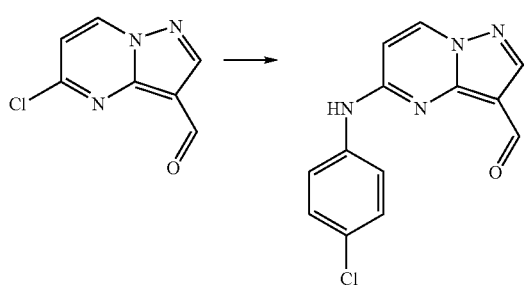 [SMILES: O=Cc1cnn2ccc(Cl)nc12 ; O=Cc1cnn2ccc(Nc3ccc(Cl)cc3)nc12]

To 5-chloropyrazolo[1,5-a]pyrimidine-3-carbaldehyde (120 mg, 0.633 mmol) in dioxane was added 3-chloroaniline (421 mg, 3.315 mmol). The mixture was heated in microwave for 20 minutes at 120° C. The solid formed was isolated by filtration and air dried to yield 5-(4-chlorophenylamino)pyrazolo[1,5-a]pyrimidine-3-carbaldehyde. LCMS (M+1=273)

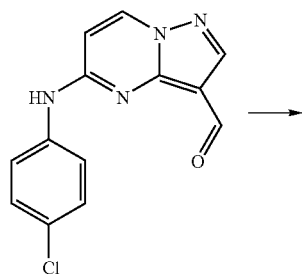

To 5-(4-chlorophenylamino)pyrazolo[1,5-a]pyrimidine-3-carbaldehyde (117 mg, 0.430 mmol) in EtOH was added hydantoin (43 mg, 0.430 mmol) and piperidine (43 μL, 0.430 mmol). The mixture was heated at 70° C. overnight. Solvent was removed under reduced pressure and the remaining solid was washed with EtOAc to yield 5-((5-(4-chlorophenylamino)pyrazolo[1,5-a]pyrimidin-3-yl)methylene)imidazolidine-2,4-dione. LCMS (M+1=355)

EXAMPLE 32

Synthesis of 5-((5-(4-chlorophenylamino)pyrazolo[1,5-a]pyrimidin-3-yl)methylene)thiazolidine-2,4-dione

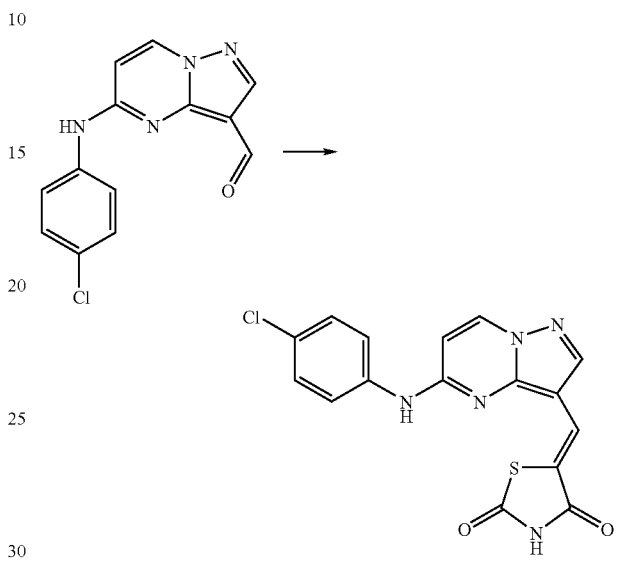

To 5-(4-chlorophenylamino)pyrazolo[1,5-a]pyrimidine-3-carbaldehyde (117 mg, 0.430 mmol) in EtOH was added thiazolidine-2,4-dione (50 mg, 0.430 mmol) and piperidine (43 μl, 0.430 mmol). The mixture was heated at 70° C. and the product formed quickly. The solid formed was isolated by filtration and air dried to yield 5-((5-(4-chlorophenylamino)pyrazolo[1,5-a]pyrimidin-3-yl)methylene)thiazolidine-2,4-dione. LCMS (M+1=372)

EXAMPLE 33

Synthesis of 5-((5-(3-(morpholinomethyl)phenylamino)pyrazolo[1,5-a]pyrimidin-3-yl)methylene)imidazolidine-2,4-dione

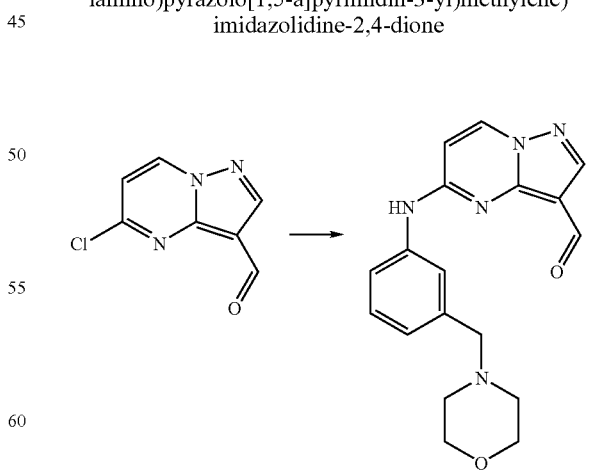

To 5-chloropyrazolo[1,5-a]pyrimidine-3-carbaldehyde (30 mg, 0.166 mmol) in DMF was added 3-(morpholinomethyl)aniline (233 mg, 1.213 mmol). The mixture was heated in microwave for 40 minutes at 140° C. Water was added and the solid formed was isolated by filtration to yield 5-(3-(morpholinomethyl)phenylamino)pyrazolo[1,5-a]pyrimidine-3-carbaldehyde. LCMS (M+1=338)

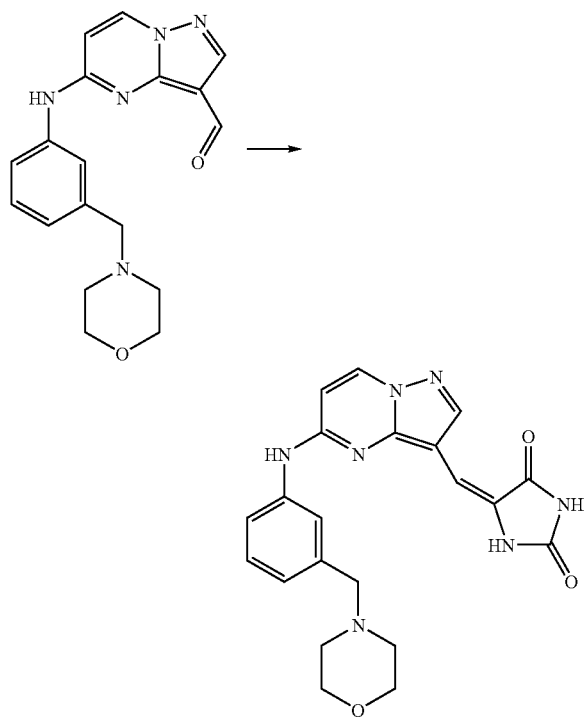

To 5-(3-(morpholinomethyl)phenylamino)pyrazolo[1,5-a]pyrimidine-3-carbaldehyde (56 mg, 0.166 mmol) in EtOH was added hydantoin (16.6 mg, 0.166 mmol) and piperidine (16.8 µL, 0.166 mmol). The mixture was heated at 70° C. overnight. The solid formed was filtered off and filtrated prepared by HPLC then TLC (1% MeOH/DCM) to yield 5-((5-(3-(morpholinomethyl)phenylamino)pyrazolo[1,5-a]pyrimidin-3-yl)methylene)imidazolidine-2,4-dione. LCMS (M+1=420)

EXAMPLE 34

Synthesis of 5-((5-(4-isopropoxyphenylamino)pyrazolo[1,5-a]pyrimidin-3-yl)methylene)imidazolidine-2,4-dione

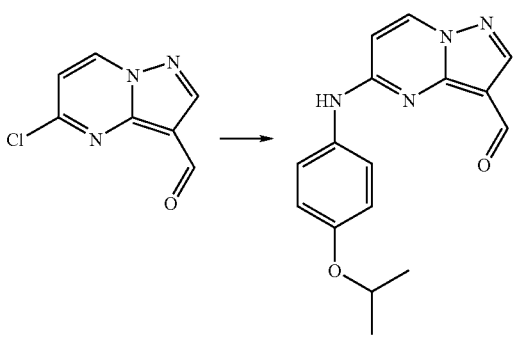 [SMILES: O=Cc1cnn2ccc(Cl)nc12 ; CC(C)Oc1ccc(Nc2ccn3ncc(C=O)c3n2)cc1]

To 5-chloropyrazolo[1,5-a]pyrimidine-3-carbaldehyde (30 mg, 0.166 mmol) in dioxane was added 4-isopropoxyaniline (125 mg, 0.829 mmol). The mixture was heated in microwave for 20 minutes at 120° C. The solid formed was isolated by filtration and air dried to yield 5-(4-isopropoxyphenylamino)pyrazolo[1,5-a]pyrimidine-3-carbaldehyde with impurities that will be removed in the final step. LCMS (M+1=297)

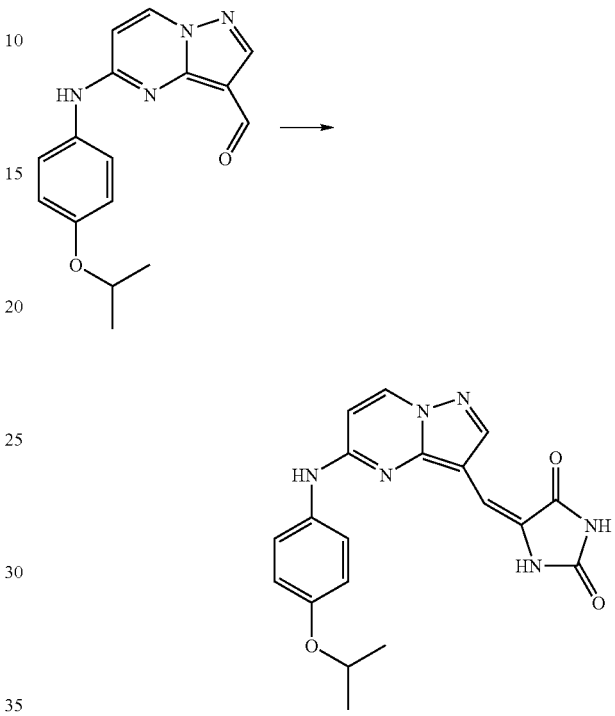

To 5-(4-isopropoxyphenylamino)pyrazolo[1,5-a]pyrimidine-3-carbaldehyde (70 mg, 0.236 mmol) in EtOH was added hydantoin (23.6 mg, 0.236 mmol) and piperidine (23.9 µL, 0.236 mmol). The mixture was heated at 70° C. overnight. The solid formed was isolated by filtration and air dried to yield 5-((5-(4-isopropoxyphenylamino)pyrazolo[1,5-a]pyrimidin-3-yl)methylene)imidazolidine-2,4-dione. LCMS (M+1=379)

EXAMPLE 35

Synthesis of 5-chloropyrazolo[1,5-a]pyrimidine-3-carbaldehyde

To 5-chloropyrazolo[1,5-a]pyrimidine (5.0 g, 32.5 mmol) in DMF was added POCl₃ (7.5 mL, 81.2 mmol). The mixture was stirred at room temperature overnight. Ice was added to quench POCl₃, then the mixture was neutralized with 1M NaOH. The resulting yellow precipitate was filtered and dried

EXAMPLE 36

Synthesis of 5-(3-formylpyrazolo[1,5-a]pyrimidin-5-yl)thiophene-2-carboxylic acid

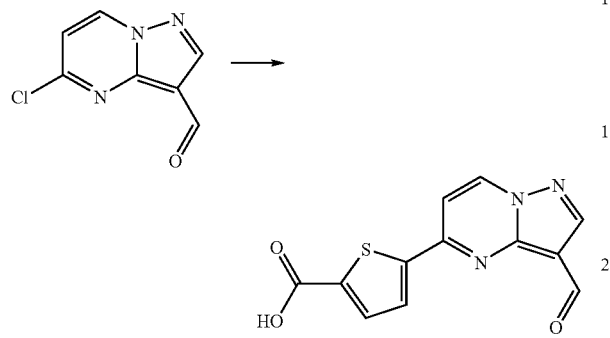

To 5-chloropyrazolo[1,5-a]pyrimidine-3-carbaldehyde (590 mg, 3.25 mmol) in DMF was added 5-Carboxythiophene-2-boronic acid (670 mg, 3.9 mmol), triethylamine (1.13 mL, 8.11 mmol) and dichloro-((bis-diphenylphosphino)ferrocenyl)palladium(II) dichloromethane adduct (120 mg, 0.16 mmol). The reaction mixture was degassed with nitrogen then heated at 100° C. for 2 hours. The mixture was cooled to room temperature, diluted with 1N HCl, and filtered. The collected solid was washed with 1N HCl and dried under vacuum. The desired product, 5-(3-formylpyrazolo[1,5-a]pyrimidin-5-yl)thiophene-2-carboxylic acid, was recovered in 22% yield and used for the next step without further purification. LCMS (M+1=274)

EXAMPLE 37

Synthesis of N-(cyclopropylmethyl)-5-(3-formylpyrazolo[1,5-a]pyrimidin-5-yl)thiophene-2-carboxamide

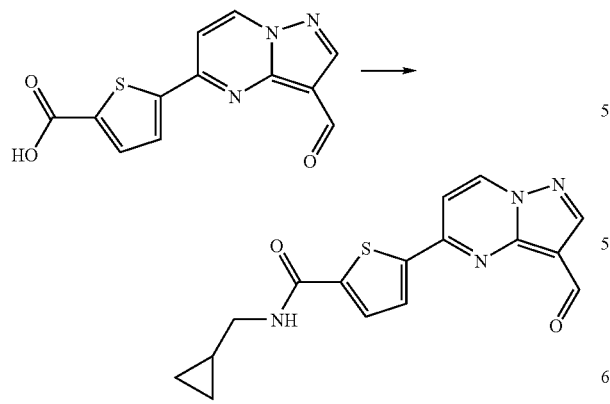

To the reaction flask, 5-(3-formylpyrazolo[1,5-a]pyrimidin-5-yl)thiophene-2-carboxylic acid (43 mg, 0.16 mmol) was added to DMF (1 mL) along with HOBt (25 mg, 0.16 mmol), triethylamine (22 uL, 0.16 mmol) and cyclopropylmethylamine (11 mg, 0.16 mmol). The reaction mixture was stirred at room temperature for 5 minutes then EDC (31 mg, 0.16 mmol) was added. The reaction was allowed to stir for an additional 2 hours then diluted with water and filtered. The recovered solid was washed with more water followed by ethanol. The product, N-(cyclopropylmethyl)-5-(3-formylpyrazolo[1,5-a]pyrimidin-5-yl)thiophene-2-carboxamide, was collected as a solid in 19% yield. LCMS (M+1=327)

EXAMPLE 38

Synthesis of N-(2-ethoxyethyl)-5-(3-formylpyrazolo[1,5-a]pyrimidin-5-yl)thiophene-2-carboxamide

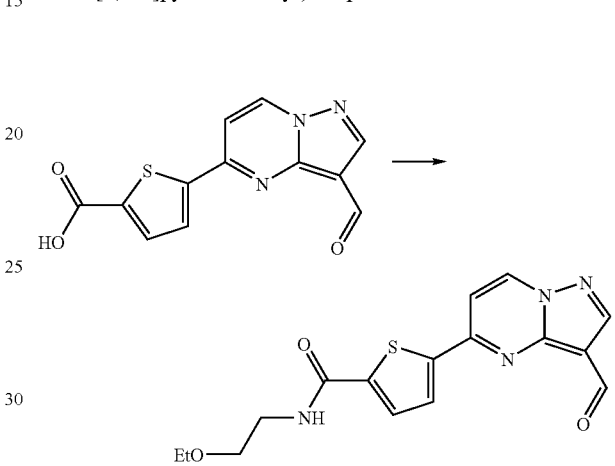

Following the procedure of Example 37, using 2-ethoxyethyl amine instead of cyclopropylmethyl amine, provided the target compound. LCMS (M+1=345)

EXAMPLE 39

Synthesis of 5-((3-formylpyrazolo[1,5-a]pyrimidin-5-yl)-N-(2-hydroxypropyl)thiophene-2-carboxamide

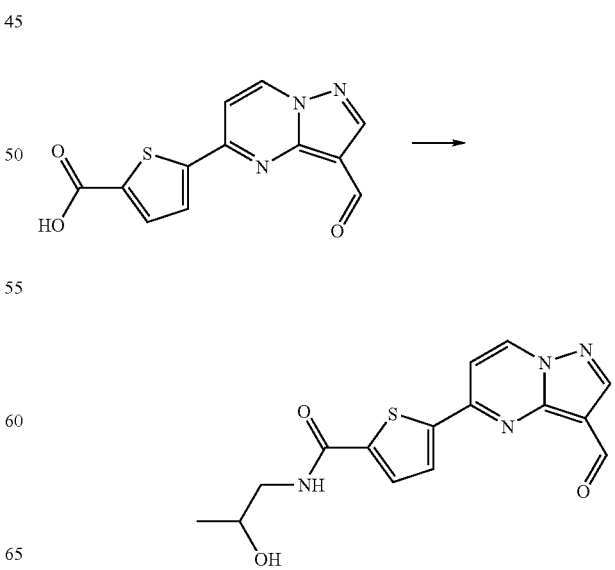

Following the procedure of Example 37, using 2-hydroxypropyl amine instead of cyclopropylmethyl amine, provided the target compound. LCMS (M+1=331)

EXAMPLE 40

Synthesis of N-(cyclopropylmethyl)-5-(3-((2,5-dioxoimidazolidin-4-ylidene)methyl)pyrazolo[1,5-a]pyrimidin-5-yl)thiophene-2-carboxamide

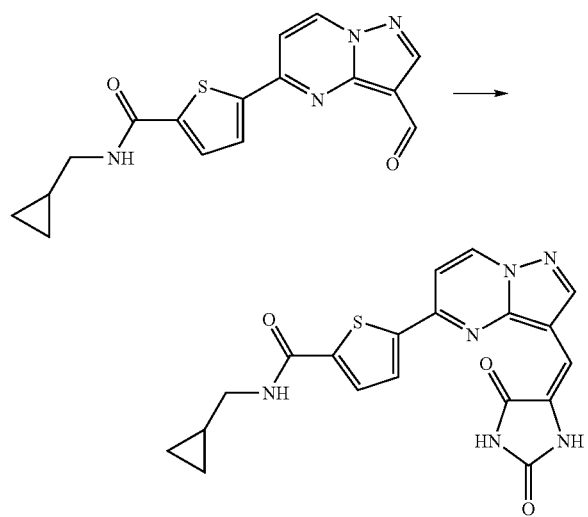

To the reaction flask, N-(cyclopropylmethyl)-5-(3-formylpyrazolo[1,5-a]pyrimidin-5-yl)thiophene-2-carboxamide (10 mg, 0.030 mmol) was added to ethanol (0.5 mL) along with hydantoin (3 mg, 0.03 mmol) and piperidine (3 uL, 0.03 mmol). The reaction was heated at 80° C. for 1 hour in the microwave then cooled to room temperature and diluted with water. The solid was collected by filtration, washed with water, 50% ethanol/water, and then 100% ethanol. The material was dried under vacuum overnight. The product, N-(cyclopropylmethyl)-5-(3-((2,5-dioxoimidazolidin-4-ylidene) methyl)pyrazolo[1,5-a]pyrimidin-5-yl)thiophene-2-carboxamide, was recovered as a solid in 29% yield. LCMS (M+1=409)

EXAMPLE 41

Synthesis of 5-(3-[((2,5-dioxoimidazolidin-4-ylidene]methyl)pyrazolo[1,5-a]pyrimidin-5-yl)-N-(2-ethoxyethyl)thiophene-2-carboxamide

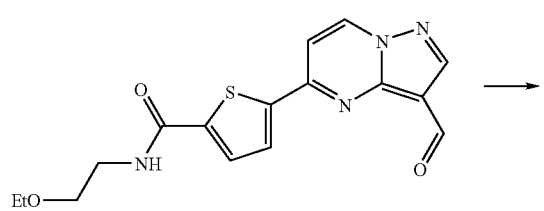

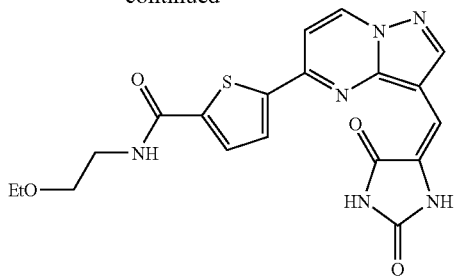

Using the procedure from Example 40 with the aldehydes produced in Example 38 provided the target compound. LCMS (M+1=427)

EXAMPLE 42

Synthesis of 5-(3-((2,5-dioxoimidazolidin-4-ylidene) methyl)pyrazolo[1,5-a]pyrimidin-5-yl)-N-(2-hydroxypropyl)thiophene-2-carboxamide

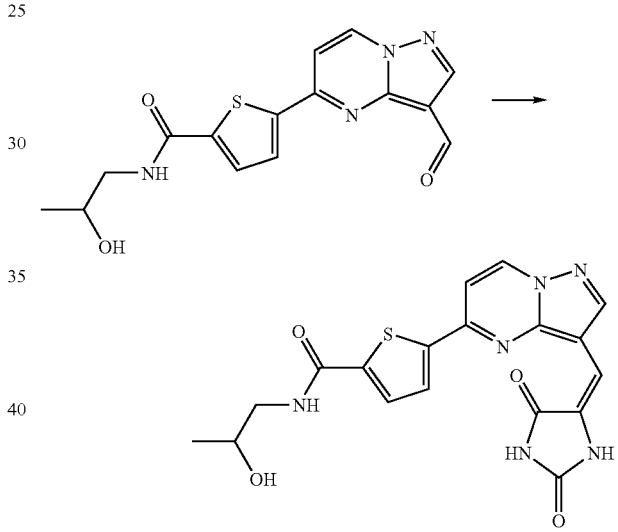

Using the procedure from Example 40 with the aldehydes produced in Example 39 provided the target compound. LCMS (M+1=413)

Biodata Test Methods

EXAMPLE 43

CK2 Assay Method

Modulatory activity of compounds described herein was assessed in vitro in cell-free CK2 assays by the following method.

Test compounds in aqueous solution were added at a volume of 10 microliters, to a reaction mixture comprising 10 microliters Assay Dilution Buffer (ADB; 20 mM MOPS, pH 7.2, 25 mM beta-glycerolphosphate, 5 mM EGTA, 1 mM sodium orthovanadate and 1 mM dithiothreitol), 10 microliters of substrate peptide (RRRDDDSDDD SEQ ID NO.: 4, dissolved in ADB at a concentration of 1 mM), 10 microliters of recombinant human CK2 (25 ng dissolved in ADB; Upstate). Reactions were initiated by the addition of 10 microliters of ATP Solution (90% 75 mM MgCl$_2$, 75 micromolar ATP dissolved in ADB; 10% [γ-$^{33}$P]ATP (stock 1 mCi/100 μl; 3000 Ci/mmol (Perkin Elmer) and maintained for 10 minutes at 30 degrees C. The reactions were quenched with 100 microliters of 0.75% phosphoric acid, then transferred to and filtered through a phosphocellulose filter plate (Millipore). After washing each well 5 times with 0.75% phosphoric acid, the plate was dried under vacuum for 5 min and, following the addition of 15 ul of scintillation fluid to each well, the residual radioactivity was measured using a Wallac luminescence counter.

EXAMPLE 44

PIM-1 Assay Method

The following procedure was used to assay the PIM-1 kinase activity of compounds of the invention. Other methods for assaying PIM-1 and other PIM kinases, as well as methods to assay for activity against the various kinases in FIG. 1, are known in the art.

In a final reaction volume of 50 ul, recombinant PIM-1 (1 ng) was incubated with 12 mM MOPS pH 7.0, 0.4 mM EDTA, glycerol 1%, brij 35 0.002%, 2- mercaptoethanol 0.02%, BSA 0.2 mg/ml, 100 uM KKRNRTLTK SEQ ID NO.: 5, 10 mM MgAcetate, 15 uM ATP, [γ-$^{33}$P-ATP] (specific activity approx. 500 cpm/μmol), DMSO 4% and test inhibitor compound at the required concentration. The reaction was initiated by the addition of the Magnesium ATP mixture. After 40 min incubation at 23° C., the reactions were quenched by the addition of 100 ul 0.75% Phosphoric acid, and the labeled peptide collected by filtration through a phosphocellulose filter plate. The plate was washed 4 times with 0.075% phosphoric acid (100 ul per well) and then, after the addition of scintillation fluid (20 ul per well), the counts were measured by a scintillation counter.

EXAMPLE 45

PIM-2 Assay Method

Test compounds dissolved and diluted in DMSO (2 μl) were added to a reaction mixture comprising 10 μl of 5× Reaction Buffer (40 mM MOPS pH 7.0, 5 mM EDTA), 10 μl of recombinant human PIM2 solution (4 ng PIM-2 dissolved in dilution buffer (20 mM MOPS pH 7.0; EDTA 1 mM; 5% Glycerol; 0.01% Brij 35; 0.1%; 0.1% 2-mercaptoethanol; 1 mg/ml BSA)) and 8 ul of water. Reactions were initiated by the addition of 10 ul of ATP Solution (49% (15 mM MgCl$_2$; 75 uM ATP) 1% ([γ-33P]ATP: Stock 1 mCi/100 μl; 3000 Ci/mmol (Perkin Elmer)) and 10 ul of substrate peptide solution (RSRSSYPAGT SEQ ID NO.: 6, dissolved in water at a concentration of 1 mM), Reactions were maintained for 10 min at 30° C. The reactions were quenched with 100 ul of 0.75% Phosphoric acid, then transferred to and filtered through a Phosphocellulose filter plate (Millipore, MSPH-N6B-50). After washing each well 4 times with 0.75% Phosphoric acid, scintillation fluid (20 uL) was added to each well and the residual radioactivity was measured using a Wallac luminescence counter.

EXAMPLE 46

Cell Proliferation Modulatory Activity

A representative cell-proliferation assay protocol using Alamar Blue dye (stored at 4° C., use 20 ul per well) is described hereafter.

96-well Plate Setup and Compound Treatment
a. Split and trypsinize cells.
b. Count cells using hemocytometer.
c. Plate 4,000-5,000 cells per well in 100 μl of medium and seed into a 96-well plate according to the following plate layout. Add cell culture medium only to wells B10 to B12. Wells B1 to B9 have cells but no compound added.

|   | 1 2 3 | 4 5 6 | 7 8 9 | 10 11 12 |         |
|---|-------|-------|-------|----------|---------|
| A |       | EMPTY |       |          |         |
| B | NO COMPOUND ADDED | | | Medium Only | |
| C | 10 nM | 100 nM | 1 uM | 10 uM | Control |
| D | 10 nM | 100 nM | 1 uM | 10 uM | Comp1 |
| E | 10 nM | 100 nM | 1 uM | 10 uM | Comp2 |
| F | 10 nM | 100 nM | 1 uM | 10 uM | Comp3 |
| G | 10 nM | 100 nM | 1 uM | 10 uM | Comp4 |
| H |       | EMPTY |       |          |         | d. Add 100 μl of 2× drug dilution to each well in a concentration shown in the plate layout above. At the same time, add 100 μl of media into the control wells (wells B10 to B12). Total volume is 200 μl/well.
e. Incubate four (4) days at 37° C., 5% CO$_2$ in a humidified incubator.
f. Add 20 μl Alamar Blue reagent to each well.
g. Incubate for four (4) hours at 37° C., 5% CO$_2$ in a humidified incubator.
h. Record fluorescence at an excitation wavelength of 544 nm and emission wavelength of 590 nm using a microplate reader.

In the assays, cells are cultured with a test compound for approximately four days, the dye is then added to the cells and fluorescence of non-reduced dye is detected after approximately four hours. Different types of cells can be utilized in the assays (e.g., HCT-116 human colorectal carcinoma cells, PC-3 human prostatic cancer cells, MDA-MB231 human breast cancer cells, K-562 human chronic myelogenous leukemia (CML) cells, MiaPaca human pancreatic carcinoma cells, MV-4 human acute myeloid leukemia cells, and BxPC3 human pancreatic adenocarcinoma cells).

Activity of compounds of Formula I in these in vitro and cellular assays are summarized in Table 1:

TABLE 1

Bioactivity Data for Compounds of Formula I.

| Structure | AB: MDAMB231 IC50 (µM) | AB: K-562 IC50 (µM) | AB: PC3 | AB: MiaPaCa IC50 (µM) | AB: MV-4-11 IC50 (µM) | CK2: IC50 (µM) | PIM1: IC50 (µM) | P21_BxPC3 IC50 (µM) | P21_MDAMB231 IC50 (µM) |
|---|---|---|---|---|---|---|---|---|---|
| (structure 1) | 8.663 | >10 | 3.912 | >10 | 0.011 | 0.013 | 0.021 | | |
| (structure 2) | >10 | 0.051 | >30 | >10 | | 0.08 | 0.091 | 5.68 | 3.16 |
| (structure 3) | >10 | >10 | >30 | >10 | >1 | 0.009 | 0.688 | | |

TABLE 1-continued

Bioactivity Data for Compounds of Formula I.

| Structure | AB: MDAMB231 IC50 (μM) | AB: K-562 IC50 (μM) | AB: PC3 | AB: MiaPaCa IC50 (μM) | AB: MV-4-11 IC50 (μM) | CK2: IC50 (μM) | PIM1: IC50 (μM) | P21_BxPC3 IC50 (μM) | P21_MDAMB231 IC50 (μM) |
|---|---|---|---|---|---|---|---|---|---|
| (pyrazolopyrimidine-chlorophenylamine-thioxothiazolidinone) | >10 | 0.153 | 0.842 | >10 | >3.e-002 | 0.006 | 0.018 | 2.66 | 0.3 |
| (pyrazolopyrimidine-chlorophenylamine-hydantoin) | 0.768 | 0.153 | 0.143 | 0.108 | >3.e-002 | 0.009 | 0.427 | 0.54 | 0.1 |
| (pyrazolopyrimidine-chlorophenylamine-thiazolidinedione) | 0.11 | 0.132 | 3.042 | 0.285 | 0.271 | 0.003 | 0.052 | 0.45 | 0.68 |
| (pyrazolopyridine-methylimidazolylphenylamine-thiazolidinedione) | >10 | >10 | | >10 | 5.376 | 0.022 | 0.004 | | |

TABLE 1-continued

Bioactivity Data for Compounds of Formula I.

| Structure | AB: MDAMB231 IC50 (µM) | AB: K-562 IC50 (µM) | AB: PC3 | AB: MiaPaCa IC50 (µM) | AB: MV-4-11 IC50 (µM) | CK2: IC50 (µM) | PIM1: IC50 (µM) | P21_BxPC3 IC50 (µM) | P21_MDAMB231 IC50 (µM) |
|---|---|---|---|---|---|---|---|---|---|
| [pyrazolopyridine-hydantoin with 3-(2-methylpropan-2-yl)phenylamino] | | | | | | 0.21 | 0.89 | | |
| [pyrazolopyridine-thiazolidinedione with 3-(2-methylpropan-2-yl)phenylamino] | | | | | | 0.079 | 0.107 | | |
| [aminopyrazolopyridine-hydantoin] | | | | | | >5 | 0.158 | | |

TABLE 1-continued

Bioactivity Data for Compounds of Formula I.

| Structure | AB: MDAMB231 IC50 (μM) | AB: K-562 IC50 (μM) | AB: PC3 | AB: MiaPaCa IC50 (μM) | AB: MV-4-11 IC50 (μM) | CK2: IC50 (μM) | PIM1: IC50 (μM) | P21_BxPC3 IC50 (μM) | P21_MDAMB231 IC50 (μM) |
|---|---|---|---|---|---|---|---|---|---|
| (structure 1) | | | | | | 0.057 | 0.537 | | |
| (structure 2) | | | | | | 0.12 | 0.061 | | |
| (structure 3) | | | | | | 0.145 | 0.431 | | |

TABLE 1-continued
Bioactivity Data for Compounds of Formula I.
| Structure | AB: MDAMB231 IC50 (μM) | AB: K-562 IC50 (μM) | AB: PC3 | AB: MiaPaCa IC50 (μM) | AB: MV-4-11 IC50 (μM) | CK2: IC50 (μM) | PIM1: IC50 (μM) | P21_BxPC3 IC50 (μM) | P21_MDAMB231 IC50 (μM) |
|---|---|---|---|---|---|---|---|---|---|
| 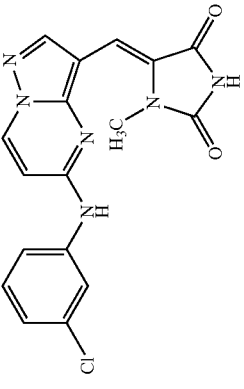 | | | | | | 0.375 | 0.239 | | |
| 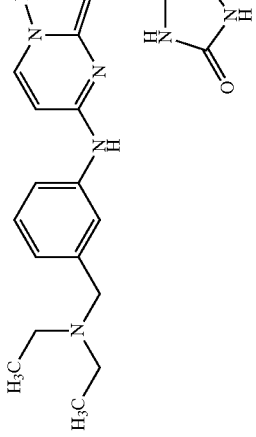 | | | | | | 0.46 | 0.373 | | |
| 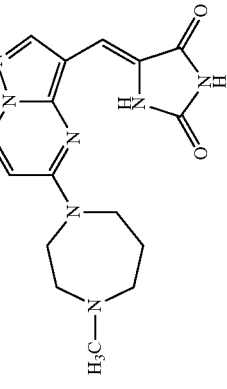 | | | | | | 1.969 | 3.531 | | |

TABLE 1-continued
Bioactivity Data for Compounds of Formula I.
| Structure | AB: MDAMB231 IC50 (µM) | AB: K-562 IC50 (µM) | AB: PC3 | AB: MiaPaCa IC50 (µM) | AB: MV-4-11 IC50 (µM) | CK2: IC50 (µM) | PIM1: IC50 (µM) | P21_BxPC3 IC50 (µM) | P21_MDAMB231 IC50 (µM) |
|---|---|---|---|---|---|---|---|---|---|
| 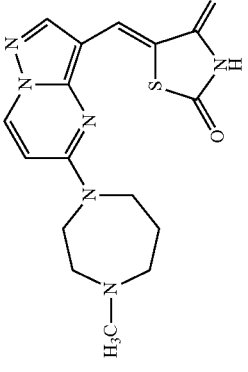 | | | | | | 0.13 | 0.126 | | |
| | | | | | | 0.247 | 0.518 | | |
| 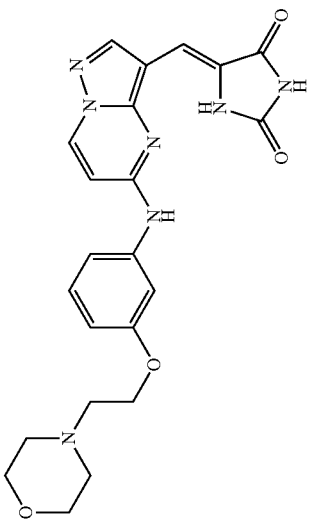 | | | | | | 0.303 | 1.25 | | |

TABLE 1-continued

Bioactivity Data for Compounds of Formula I.

| Structure | AB: MDAMB231 IC50 (μM) | AB: K-562 IC50 (μM) | AB: PC3 | AB: MiaPaCa IC50 (μM) | AB: MV-4-11 IC50 (μM) | CK2: IC50 (μM) | PIM1: IC50 (μM) | P21_BxPC3 IC50 (μM) | P21_MDAMB231 IC50 (μM) |
|---|---|---|---|---|---|---|---|---|---|
| | | | 9.709 | | | 0.023 | 1.042 | | |
| | | | 6.554 | | | 0.035 | 0.346 | | |
| | | | | | | 0.058 | 0.431 | | |

TABLE 1-continued

Bioactivity Data for Compounds of Formula I.

| Structure | AB: MDAMB231 IC50 (μM) | AB: K-562 IC50 (μM) | AB: PC3 | AB: MiaPaCa IC50 (μM) | AB: MV-4-11 IC50 (μM) | CK2: IC50 (μM) | PIM1: IC50 (μM) | P21_BxPC3 IC50 (μM) | P21_MDAMB231 IC50 (μM) |
|---|---|---|---|---|---|---|---|---|---|
| | | | | | | 0.574 | 1.571 | | |
| | | | >10 | | | 2.147 | 2.385 | | |
| | | | | | | 0.015 | 0.025 | | |

TABLE 1-continued
Bioactivity Data for Compounds of Formula I.
| Structure | AB: MDAMB231 IC50 (μM) | AB: K-562 IC50 (μM) | AB: PC3 | AB: MiaPaCa IC50 (μM) | AB: MV-4-11 IC50 (μM) | CK2: IC50 (μM) | PIM1: IC50 (μM) | P21_BxPC3 IC50 (μM) | P21_MDAMB231 IC50 (μM) |
|---|---|---|---|---|---|---|---|---|---|
| 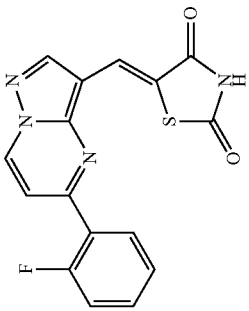 | | | >10 | | | 0.041 | 0.24 | | |
| 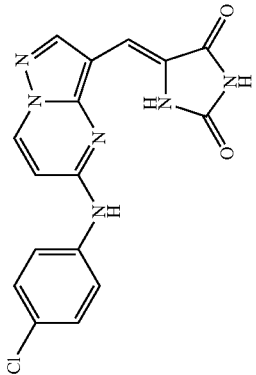 | | | | | | 0.179 | 3.012 | | |
| | | | | | | 0.02 | 0.194 | | |

TABLE 1-continued

Bioactivity Data for Compounds of Formula I.

| Structure | AB: MDAMB231 IC50 (μM) | AB: K-562 IC50 (μM) | AB: PC3 | AB: MiaPaCa IC50 (μM) | AB: MV-4-11 IC50 (μM) | CK2: IC50 (μM) | PIM1: IC50 (μM) | P21_BxPC3 IC50 (μM) | P21_MDAMB231 IC50 (μM) |
|---|---|---|---|---|---|---|---|---|---|
| | | | | | | 0.007 | | | |

TABLE 1-continued

Bioactivity Data for Compounds of Formula I.

| Structure | AB: MDAMB231 IC50 (μM) | AB: K-562 IC50 (μM) | AB: PC3 | AB: MiaPaCa IC50 (μM) | AB: MV-4-11 IC50 (μM) | CK2: IC50 (μM) | PIM1: IC50 (μM) | P21_BxPC3 IC50 (μM) | P21_MDAMB231 IC50 (μM) |
|---|---|---|---|---|---|---|---|---|---|
| [structure] | | | | | | <0.1 | [0.58 for PIM2 (5 μM ATP)] | | |
| [structure] | | | | | | <0.1 | [1.06 for PIM2 (5 μM ATP)] | | |
| [structure] | | | | | | <0.1 | [0.54 for PIM2 (5 μM ATP)] | | |

The invention claimed is:
1. A compound of Formula (I):

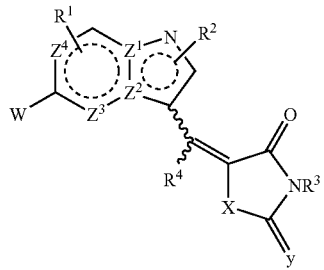

wherein the bicyclic ring system containing $Z^1$-$Z^4$ is aromatic;
$Z^1$ and $Z^3$ are N; $Z^2$ is C; and $Z^4$ is $CR^5$;
where $R^5$ can be H or $R^1$;
$R^1$ is H, halo, CN, optionally substituted C1-C4 alkyl, or optionally substituted C1-C4 alkoxy;
$R^2$ is H, halo, CN, or optionally substituted C1-C4 alkyl;
$R^3$ and $R^4$ are independently selected from H and optionally substituted C1-C10 alkyl;
X is $NR^6$, O, or S, where $R^6$ is H or an optionally substituted group selected from C1-C4 alkyl, C2-C4 alkenyl, and C2-C4 alkynyl;
Y is O or S or $NR^{10}$;
$R^{10}$ is selected from H, CN, optionally substituted C1-C4 alkyl, optionally substituted C2-C4 alkenyl, optionally substituted C2-C4 alkynyl, optionally substituted C1-C4 alkoxy, or —$NR^7R^8$, where $R^7$ and $R^8$ are independently selected from H, optionally substituted C1-C10 alkyl, optionally substituted aryl, optionally substituted arylalkyl, optionally substituted heteroaryl, and optionally substituted heteroarylalkyl, or $R^7$ and $R^8$ taken together with the N of —$NR^7R^8$ can form an optionally substituted 5-8 membered ring that optionally contains an additional heteroatom selected from N, O and S as a ring member;
W is optionally substituted aryl, optionally substituted heteroaryl, —$OR^7$, —$NR^7R^8$, or optionally substituted heterocyclyl,
wherein n is 0, 1 or 2,
each $R^7$ and $R^8$ are each independently selected from H, optionally substituted C1-C10 alkyl, optionally substituted aryl, optionally substituted arylalkyl, optionally substituted heteroaryl, and optionally substituted heteroarylalkyl;
wherein $R^7$ and $R^8$ in $NR^7R^8$ can be taken together along with N to form a 5-8 membered ring that can be optionally substituted, and can optionally contain an additional heteroatom selected from N, O and S as a ring member;
or a pharmaceutically acceptable salt thereof.
2. The compound of claim 1, wherein X is $NR^6$ or S.
3. The compound of claim 1, wherein $R^2$ is H, Me.
4. The compound of claim 1, wherein $R^3$ and $R^4$ are both H.
5. The compound of claim 1, wherein $R^1$ is H, Me, halo, OMe, or $CF_3$.
6. The compound of claim 1, wherein Y is O.
7. The compound of claim 1, wherein Y is S.
8. The compound of claim 1, wherein W is —NH-A, wherein A is optionally substituted phenyl.
9. The compound of claim 1, wherein W is optionally substituted aryl or optionally substituted heteroaryl.
10. The compound of claim 9, wherein W is optionally substituted phenyl or optionally substituted thienyl.

11. The compound of claim 1, which is a compound of Formula Ia or Formula Ib:
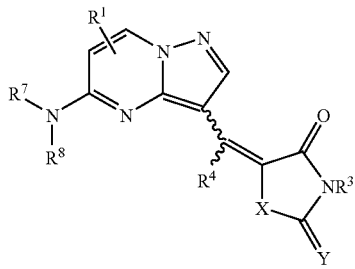
Ia
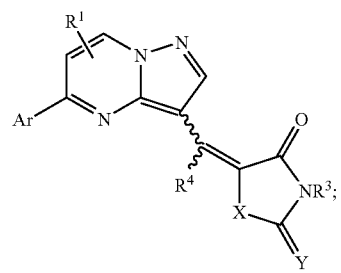
Ib
wherein $R^1$, $R^3$, $R^4$, $R^9$, $R^{10}$, X, and Y are as defined in claim 1,
and Ar is optionally substituted phenyl or optionally substituted thienyl.
12. The compound of claim 1, which is selected from the group consisting of
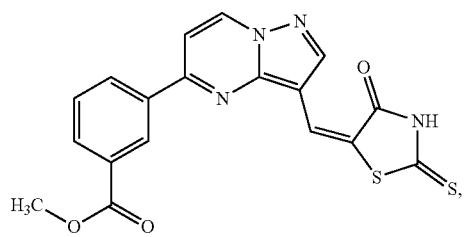
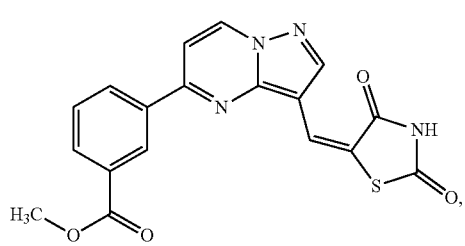
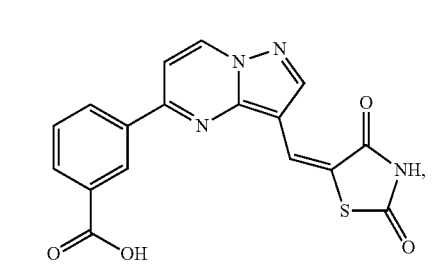
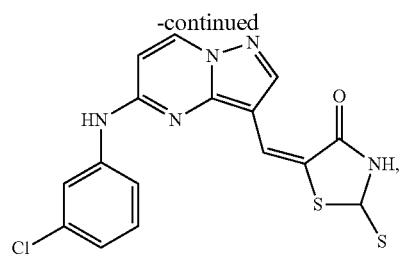
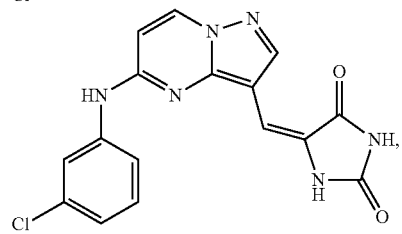
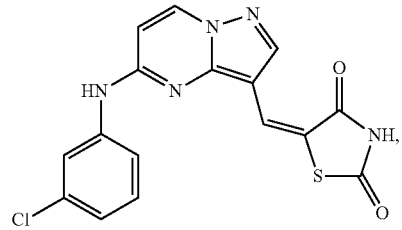
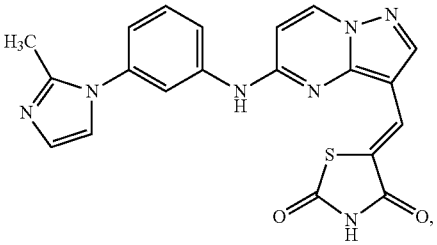
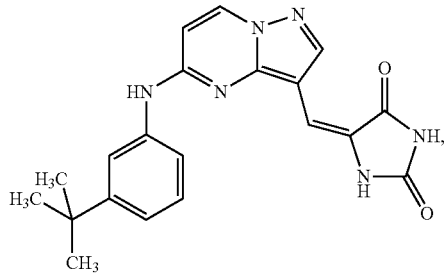
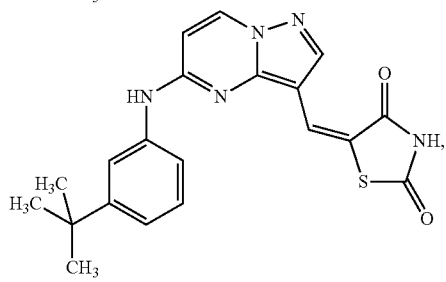

105
-continued
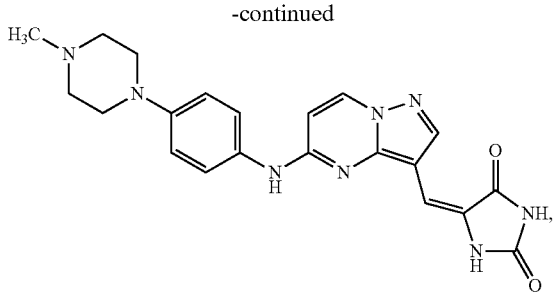
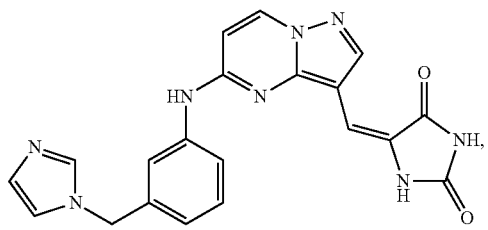
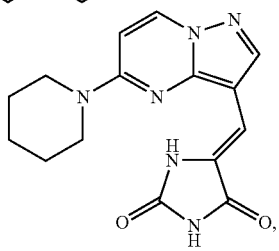
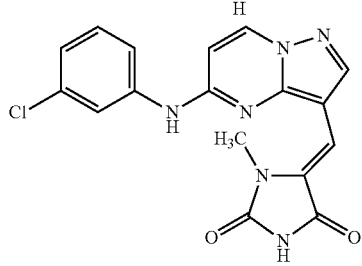
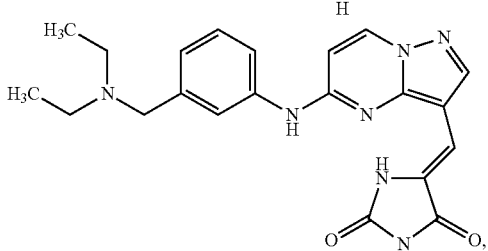
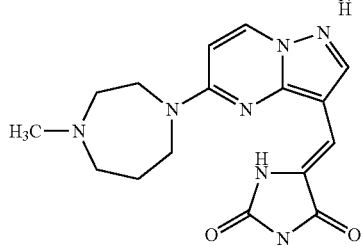
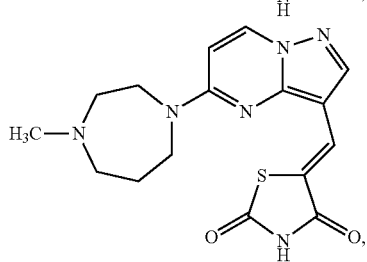
106
-continued
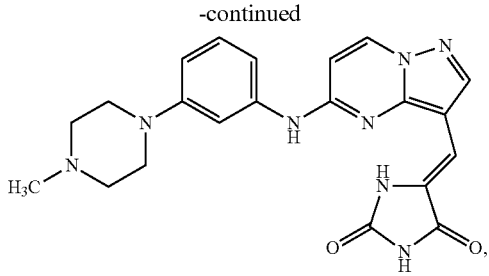
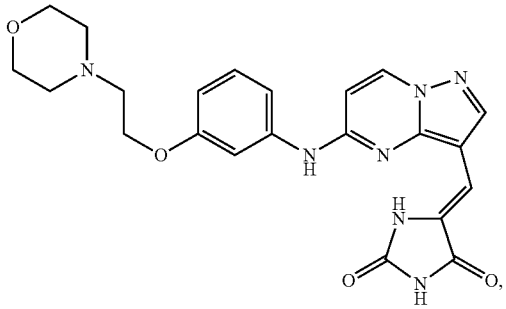
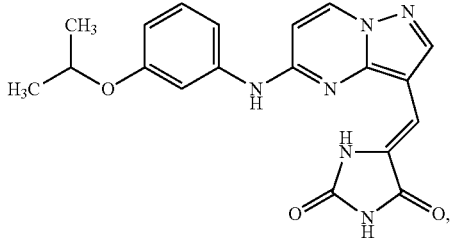
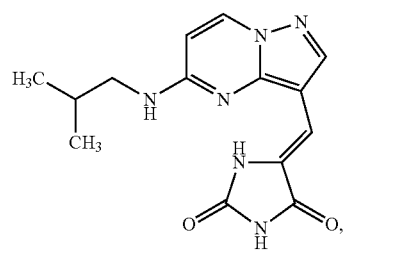
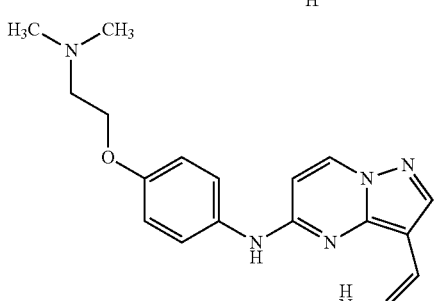
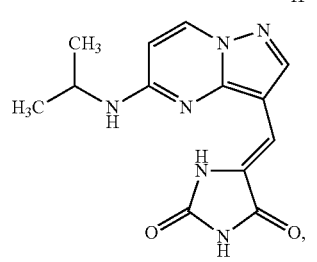

107
-continued
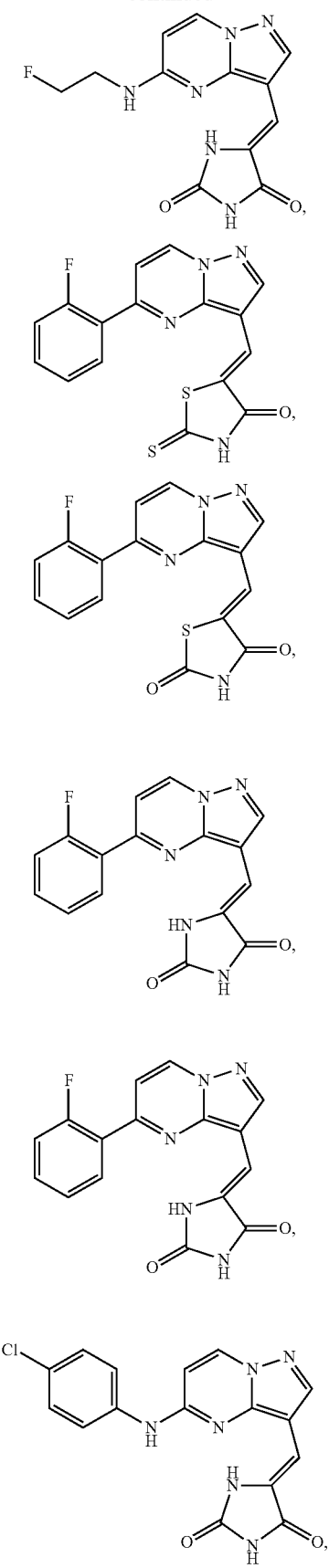
108
-continued
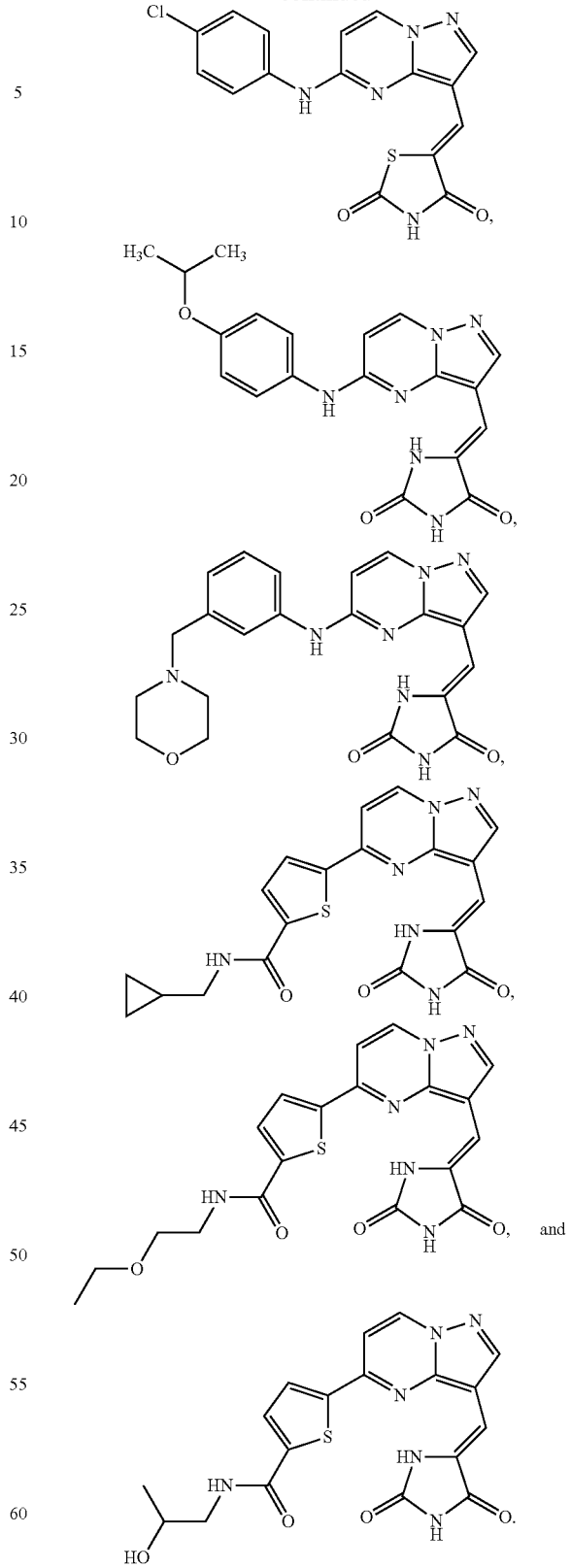
13. A pharmaceutical composition comprising the compound of claim 1, admixed with a pharmaceutically acceptable excipient.
* * * * *